United States Patent
Kim et al.

(10) Patent No.: US 9,309,197 B2
(45) Date of Patent: Apr. 12, 2016

(54) HETEROCYCLIC COMPOUND, ORGANIC LIGHT-EMITTING DIODE COMPRISING THE HETEROCYCLIC COMPOUND, AND FLAT PANEL DISPLAY DEVICE COMPRISING THE ORGANIC LIGHT-EMITTING DIODE

(75) Inventors: Young-Kook Kim, Yongin (KR); Seok-Hwan Hwang, Yongin (KR); Hye-Jin Jung, Yongin (KR); Jin-O Lim, Yongin (KR); Sang-Hyun Han, Yongin (KR); Se-Jin Cho, Yongin (KR); Jong-Hyuk Lee, Yongin (KR)

(73) Assignee: Samsung Display Co., Ltd., Giheung-Gu, Yongin-si, Gyeonggi-Do (KR)

( * ) Notice: Subject to any disclaimer, the term of this patent is extended or adjusted under 35 U.S.C. 154(b) by 609 days.

(21) Appl. No.: 13/399,108

(22) Filed: Feb. 17, 2012

(65) Prior Publication Data

US 2013/0087768 A1 Apr. 11, 2013

(30) Foreign Application Priority Data

Oct. 10, 2011 (KR) ........................ 10-2011-0103057

(51) Int. Cl.
*H01L 51/54* (2006.01)
*C09K 11/06* (2006.01)
(Continued)

(52) U.S. Cl.
CPC ............ *C07D 209/86* (2013.01); *C07D 401/10* (2013.01); *C07D 403/10* (2013.01); *C07D 405/04* (2013.01); *C07D 409/04* (2013.01); *C07D 413/10* (2013.01); *C07D 471/04* (2013.01); *C07D 491/04* (2013.01); *C07D 495/04* (2013.01); *C07F 7/0812* (2013.01); *C09K 11/06* (2013.01); *H01L 51/0072* (2013.01); *H05B 33/14* (2013.01); *C09K 2211/1007* (2013.01); *C09K 2211/1011* (2013.01); *C09K 2211/1014* (2013.01); *C09K 2211/1029* (2013.01); *C09K 2211/1044* (2013.01); *C09K 2211/1048* (2013.01); *C09K2211/1059* (2013.01); *C09K 2211/1088* (2013.01); *C09K 2211/1092* (2013.01)

(58) Field of Classification Search
None
See application file for complete search history.

(56) References Cited

U.S. PATENT DOCUMENTS 6,465,115 B2 10/2002 Shi et al.
6,596,415 B2 7/2003 Shi et al.
(Continued)

FOREIGN PATENT DOCUMENTS

JP 2010-45281 A 2/2010
KR 10-2010-0105099 A 9/2010
(Continued)

OTHER PUBLICATIONS

Korean Office Action dated Dec. 18, 2012 issued by KIPO for the corresponding Korean Patent application 10-2011-0103057 with Request for Entry of the Accompanying Office Action.
(Continued)

*Primary Examiner* — Andrew K Bohaty
(74) *Attorney, Agent, or Firm* — Robert E. Bushnell, Esq.

(57) ABSTRACT

A heterocyclic compound represented by Formula 1 below, an organic light-emitting diode including the same, and a flat panel display device including the organic light-emitting diode:

[Formula 1]

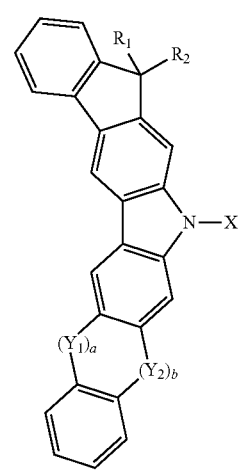

where X is *—Ar$_1$ or

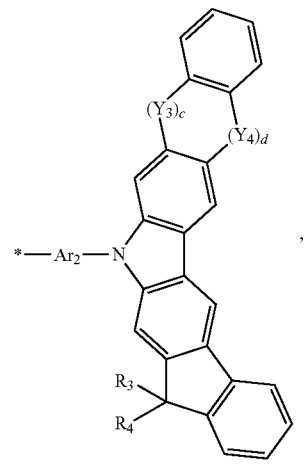

wherein Ar$_1$, Ar$_2$, R$_1$, R$_2$, R$_3$, R$_4$, Y$_1$, Y$_2$, Y$_3$, Y$_4$, a, b, c, and d are as defined in the specification.

24 Claims, 1 Drawing Sheet

(51) Int. Cl.

| | | |
|---|---|---|
| C07D 209/86 | (2006.01) | |
| C07D 401/10 | (2006.01) | |
| C07D 403/10 | (2006.01) | |
| C07D 405/04 | (2006.01) | |
| C07D 409/04 | (2006.01) | |
| C07D 413/10 | (2006.01) | |
| C07D 471/04 | (2006.01) | |
| C07D 491/04 | (2006.01) | |
| C07D 495/04 | (2006.01) | |
| C07F 7/08 | (2006.01) | |
| H01L 51/00 | (2006.01) | |
| H05B 33/14 | (2006.01) | |

(56) References Cited

U.S. PATENT DOCUMENTS

2003/0067266 A1* 4/2003 Kim et al. ............... 313/504
2009/0309488 A1  12/2009 Kato et al.
2011/0266533 A1* 11/2011 Buesing et al. ............ 257/40
2012/0068170 A1*  3/2012 Pflumm et al. ............ 257/40

FOREIGN PATENT DOCUMENTS

| KR | 10-2011-0009920 A | 1/2011 |
| KR | 10-2011-0018340 A | 2/2011 |
| KR | 10-2012-0065214 A | 6/2012 |
| KR | 1020120065214 A | 6/2012 |
| WO | 2009148015 A1 | 12/2009 |
| WO | WO 2010083871 A1 * | 7/2010 |
| WO | 2010136109 A1 | 12/2010 |
| WO | 2012013271 A1 | 2/2012 |

OTHER PUBLICATIONS

European Search Report issued by European Patent Office on Oct. 5, 2012 in the examination of the EP Application No. 12181193.9.

* cited by examiner

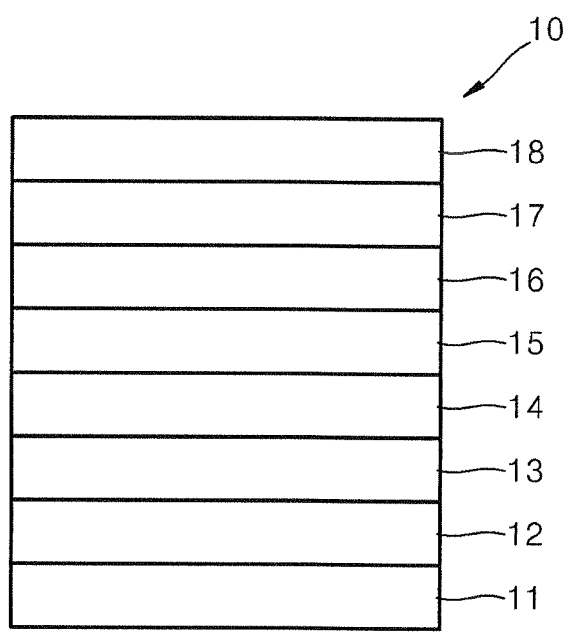

HETEROCYCLIC COMPOUND, ORGANIC LIGHT-EMITTING DIODE COMPRISING THE HETEROCYCLIC COMPOUND, AND FLAT PANEL DISPLAY DEVICE COMPRISING THE ORGANIC LIGHT-EMITTING DIODE

CROSS-REFERENCE TO RELATED PATENT APPLICATION

This application claims the benefit of Korean Patent Application No. 10-2011-0103057; filed on Oct. 10, 2011, in the Korean Intellectual Property Office, the disclosure of which is incorporated herein in its entirety by reference.

BACKGROUND OF THE INVENTION

1. Field of the Invention

The present invention relates to a heterocyclic compound, an organic light-emitting diode including the heterocyclic compound, and a flat panel display device including the organic light-emitting diode.

2. Description of the Related Art

Organic light-emitting diodes (OLEDs), which are self-emitting devices, have advantages such as a wide viewing angle, excellent contrast, quick response, high brightness, excellent driving voltage characteristics, and can provide multicolored images. Thus, OLEDs have drawing attention.

A general organic light-emitting diode has a structure including a substrate, and an anode, a hole transport layer (HTL), an emission layer (EML), an electron transport layer (ETL), and a cathode which are sequentially stacked on the substrate. In this regard, the HTL, the EML, and the ETL are organic thin films formed of organic compounds. When a voltage is applied between the anode and the cathode, holes injected from the anode move to the EML via the HTL, and electrons injected from the cathode move to the EML via the ETL. The holes and electrons recombine in the EML to generate excitons. When the excitons drop from an excited state to a ground state, light is emitted. In this regard, emission occurring when singlet excitons drop from an excited state to a ground state refers to "fluorescence", and emission occurring when triplet excitons drop from an excited state to a ground state refers to "phosphorescence". Since a probability of excited singlet exciton is 25% in the fluorescence, the light emitting efficiency is limited. However, 75% of excited triplet excitons and 25% of excited singlet excitons can be used in the phosphorescence, and thus internal quantum efficiency increases up to 100%.

U.S. Pat. Nos. 6,596,415 and 6,465,115 disclose an organic light-emitting diode using 4,4'-N,N-dicarbazole-biphenyl (CBP) as a host of an emission layer. CBP is a widly known host material of a phosphorescent emitting material, and an organic light-emitting diode with high emission efficiency of green and red colors and using phosphorescence is well known in the art. The organic light-emitting diode includes Ir(ppy)$_3$, as a phosphorescent dye having a heavy element such as Ir and Pt with high spin-orbital coupling at its center, PtOEP, as a dopant, and CBP, as a host, so that light is efficiently emitted in a triplet state (phosphorescence). Recently, an iridium (III) complex has been known as a phosphorescent dopant material, and (acac)Ir(btp)$_2$, Ir(ppy)$_3$ and Firpic, and the like are well known in the art for RGB emission. In addition, an organic light-emitting diode including CBP as a host material of a phosphorescence emitting material, and BCP and Balq in a hole blocking layer is reported, and a high performance organic light-emitting diode using a BAlq derivative as a host is disclosed. However, the organic light-emitting diode has a short lifespan of 150 hours or less. This is because, CBP has a low glass transition temperature Tg of 110° C. or less, is easily crystallized, and has low thermal stability. Thus, CBP deforms during a high-temperature deposition.

International Publication No. WO2009/148015 discloses an organic light-emitting diode including a polycyclic compound as a host material. The polycyclic compound has a π-conjugated heteroacene backbone crosslinked with carbon atoms, nitrogen atoms, oxygen atom, or sulfur atoms, and is prepared by a synthesis of a halogen compound. An organic light-emitting diode including the polycyclic compound has high light emittin efficiency and long lifespan. However, these organic light-emitting diodes have sufficient electrical stability, and thus cannot be commercialized.

SUMMARY

The present invention provides a heterocyclic compound, an organic light-emitting diode including an organic layer that includes the heterocyclic compound, and a flat panel display device including the organic light-emitting diode.

According to an aspect of the present invention, there is provided a heterocyclic compound represented by Formula 1 below:

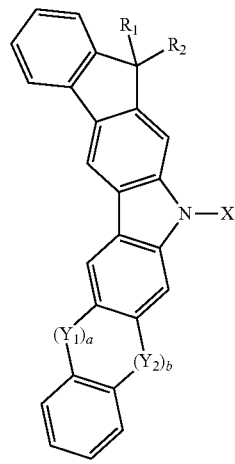

Formula 1 wherein X is *—Ar$_1$ or

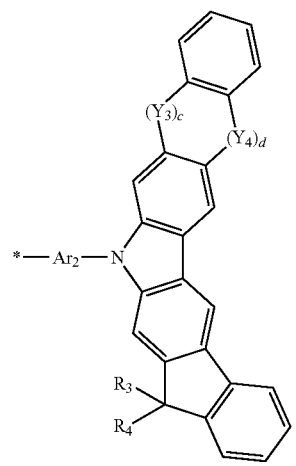

where * indicates a binding site;

wherein $Ar_1$ is a substituted or unsubstituted $C_5$-$C_{60}$ aryl group, a substituted or unsubstituted $C_5$-$C_{60}$ aryloxy group, a substituted or unsubstituted $C_5$-$C_{60}$ arylthio group, a substituted or unsubstituted $C_2$-$C_{60}$ heteroaryl group, or a substituted or unsubstituted $C_2$-$C_{60}$ polycyclic condensed group; $Ar_2$ is a substituted or unsubstituted $C_5$-$C_{60}$ arylene group, a substituted or unsubstituted $C_5$-$C_{60}$ aryleneoxy group, a substituted or unsubstituted $C_5$-$C_{60}$ arylenethio group, a substituted or unsubstituted $C_2$-$C_{60}$ heteroarylene group, or a substituted or unsubstituted $C_2$-$C_{60}$ polycyclic condensed group; $Y_1, Y_2, Y_3$ and $Y_4$ are each independently $CR_5R_6$, $NR_7$, O, or S; a, b, c and d are each independently an integer of 0 or 1, wherein a+b=1 and c+d=1; and $R_1, R_2, R_3, R_4, R_5, R_6$ and $R_7$ are each independently a hydrogen atom, a deuterium, a tritium, a halogen atom, a hydroxyl group, a cyano group, a nitro group, a carboxyl group, a silyl group, a substituted or unsubstituted $C_1$-$C_{50}$ alkyl group, a substituted or unsubstituted $C_2$-$C_{50}$ alkenyl group, a substituted or unsubstituted $C_2$-$C_{50}$ alkynyl group, a substituted or unsubstituted $C_1$-$C_{50}$ alkoxy group, a substituted or unsubstituted $C_3$-$C_{50}$ cycloalkyl group, a substituted or unsubstituted $C_3$-$C_{50}$ cycloalkenyl group, a substituted or unsubstituted $C_5$-$C_{60}$ aryl group, a substituted or unsubstituted $C_5$-$C_{60}$ aryloxy group, a substituted or unsubstituted $C_5$-$C_{60}$ arylthio group, a substituted or unsubstituted $C_2$-$C_{60}$ heteroaryl group, a substituted or unsubstituted $C_2$-$C_{60}$ polycyclic condensed group, or $N(Q_1)(Q_2)$, and $Q_1$ and $Q_2$ are each independently a hydrogen atom, a deuterium, a tritium, a halogen atom, a hydroxyl group, a cyano group, a nitro group, a carboxyl group, a silyl group, a substituted or unsubstituted $C_1$-$C_{50}$ alkyl group, a substituted or unsubstituted $C_2$-$C_{50}$ alkenyl group, a substituted or unsubstituted $C_2$-$C_{50}$ alkynyl group, a substituted or unsubstituted alkoxy group, a substituted or unsubstituted $C_3$-$C_{50}$ cycloalkyl group, a substituted or unsubstituted $C_3$-$C_{50}$ cycloalkenyl group, a substituted or unsubstituted $C_5$-$C_{60}$ aryl group, a substituted or unsubstituted $C_5$-$C_{60}$ aryloxy group, a substituted or unsubstituted $C_5$-$C_{60}$ arylthio group, a substituted or unsubstituted $C_2$-$C_{60}$ heteroaryl group, and a substituted or unsubstituted $C_2$-$C_{60}$ polycyclic condensed group, wherein at least two of $R_1, R_2, R_3, R_4, R_5, R_6$, and $R_7$ which are adjacent to each other bind to each other to form a saturated or unsaturated ring.

According to another aspect of the present invention, there is provided an organic light-emitting diode including a first electrode; a second electrode disposed opposite to the first electrode; an organic layer interposed between the first electrode and the second electrode, wherein the organic layer includes a heterocyclic compound according to any one of claims 1 to 13 as a single material or a mixture of different materials.

According to another aspect of the present invention, there is provided a flat panel display device including a transistor including a source, a drain, a gate, and an active layer and the above organic light-emitting diode, wherein one of the source and the drain is electrically connected to the first electrode of the organic light-emitting diode.

BRIEF DESCRIPTION OF THE DRAWINGS

The above and other features and advantages of the present invention will become more apparent by describing in detail exemplary embodiments thereof with reference to the attached drawing in which:

FIG. 1 is a schematic cross-sectional view of an organic light-emitting diode according to an embodiment of the present invention.

DETAILED DESCRIPTION

Hereinafter, exemplary embodiments of the present invention will be described in detail with reference to the accompanying drawing.

As used herein, the term "and/or" includes any and all combinations of one or more of the associated listed items. Expressions such as "at least one of," when preceding a list of elements, modify the entire list of elements and do not modify the individual elements of the list.

According to an embodiment of the present invention, there is provided a heterocyclic compound represented by Formula 1 below.

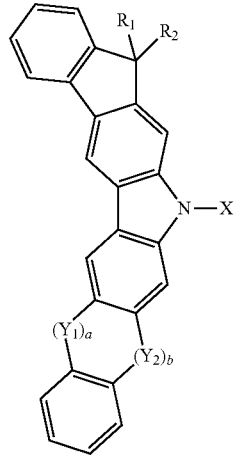

Formula 1

In Formula 1, X is *—$Ar_1$ or

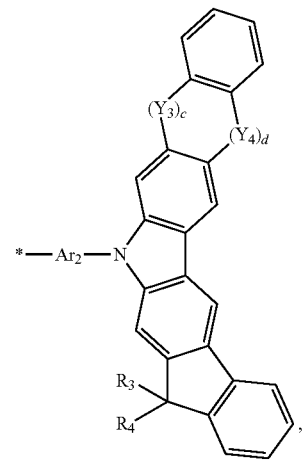

wherein $Ar_1$ is a substituted or unsubstituted $C_5$-$C_{60}$ aryl group, a substituted or unsubstituted $C_5$-$C_{60}$ aryloxy group, a substituted or unsubstituted $C_5$-$C_{60}$ arylthio group, a substituted or unsubstituted $C_2$-$C_{60}$ heteroaryl group, or a substituted or unsubstituted $C_2$-$C_{60}$ polycyclic condensed group;

$Ar_2$ is a substituted or unsubstituted $C_5$-$C_{60}$ arylene group, a substituted or unsubstituted $C_5$-$C_{60}$ aryleneoxy group, a substituted or unsubstituted $C_5$-$C_{60}$ arylenethio group, a substituted or unsubstituted $C_2$-$C_{60}$ heteroarylene group, and a substituted or unsubstituted bivalent $C_2$-$C_{60}$ polycyclic condensed group; and \* indicates a binding site.

In Formula 1, $Y_1$, $Y_2$, $Y_3$ and $Y_4$ are each independently $CR_5R_6$, $NR_7$, O, or S, and a, b, c and d are each independently an integer of 0 or 1, wherein a+b=1 and c+d=1. $R_5$, $R_6$, and $R_7$ will be described in detail later. The expression "a, b, c, and d are each independently an integer of 0 or 1, wherein a+b=1 and c+d=1" indicates that one of a and b is 1, and the other is 0, and one of c and d is 1, and the other is 0. For example, a is 1 and b is 0, or a is 0 and b is 1, and c is 1 and d is 0, or c is 0 and d is 1.

In Formula 1, $R_1$, $R_2$, $R_3$, $R_4$, $R_5$, $R_6$ and $R_7$ are each independently a hydrogen atom, a deuterium, a tritium, a halogen atom, a hydroxyl group, a cyano group, a nitro group, a carboxyl group, a silyl group, a substituted or unsubstituted $C_1$-$C_{50}$ alkyl group, a substituted or unsubstituted $C_2$-$C_{50}$ alkenyl group, a substituted or unsubstituted $C_2$-$C_{50}$ alkynyl group, a substituted or unsubstituted $C_1$-$C_{50}$ alkoxy group, a substituted or unsubstituted $C_3$-$C_{50}$ cycloalkyl group, a substituted or unsubstituted $C_3$-$C_{50}$ cycloalkenyl group, a substituted or unsubstituted $C_5$-$C_{60}$ aryl group, a substituted or unsubstituted $C_5$-$C_{60}$ aryloxy group, a substituted or unsubstituted $C_5$-$C_{60}$ arylthio group, a substituted or unsubstituted $C_2$-$C_{60}$ heteroaryl group, a substituted or unsubstituted $C_2$-$C_{60}$ polycyclic condensed group, or $N(Q_1)(Q_2)$. In this regard, $Q_1$ to $Q_2$ are each independently a hydrogen atom, a deuterium, a tritium, a halogen atom, a hydroxyl group, a silyl group, a cyano group, a nitro group, a carboxyl group, a substituted or unsubstituted $C_1$-$C_{50}$ alkyl group, a substituted or unsubstituted $C_2$-$C_{50}$ alkenyl group, a substituted or unsubstituted $C_2$-$C_{50}$ alkynyl group, a substituted or unsubstituted $C_1$-$C_{50}$ alkoxy group, a substituted or unsubstituted $C_3$-$C_{50}$ cycloalkyl group, a substituted or unsubstituted $C_3$-$C_{50}$ cycloalkenyl group, a substituted or unsubstituted $C_5$-$C_{60}$ aryl group, a substituted or unsubstituted $C_5$-$C_{60}$ aryloxy group, a substituted or unsubstituted $C_5$-$C_{60}$ arylthio group, or a substituted or unsubstituted $C_2$-$C_{60}$ heteroaryl group, or a substituted or unsubstituted $C_2$-$C_{60}$ polycyclic condensed group. At least two of $R_1$, $R_2$, $R_3$, $R_4$, $R_5$, $R_6$ and $R_7$, which are adjacent to each other, may form a saturated or unsaturated ring.

The heterocyclic compound represented by Formula 1 has high glass transition temperature Tg or high melting point since the heterocyclic backbone is introduced into molecules thereof. Thus, an organic light-emitting diode including the heterocyclic compound represented by Formula 1 is resistant against Joule's heat generated in the organic layer, Joule's heat generated between the organic layers, or Joule's heat generated between the organic layer and a metal electrode during the emission, and thermal resistant thereof increases under high temperature. In addition, the heterocyclic compound represented by Formula 1 has a fluorene group, resulting in having high glass transition temperature Tg and not crystallized.

In an organic light-emitting diode, the heterocyclic compound represented by Formula 1 has high electrical stability, high charge transporting capabilities, and excellent emitting capabilities. Thus, the heterocyclic compound may be efficiently used in fluorescent or phosphorescent devices emitting all colors, for example, red, green, and white colors, and may be used as an electron injecting material or an electron transporting material.

In the heterocyclic compound of Formula 1, X may be $Ar_1$, wherein $Ar_1$ may be a substituted or unsubstituted phenyl group, a substituted or unsubstituted biphenyl group, a substituted or unsubstituted pentalenyl, a substituted or unsubstituted indenyl group, a substituted or unsubstituted naphthyl group, a substituted or unsubstituted azulenyl group, a substituted or unsubstituted heptalenyl group, a substituted or unsubstituted indacenyl group, a substituted or unsubstituted acenaphtyl group, a substituted or unsubstituted fluorenyl group, a substituted or unsubstituted spiro-fluorenyl group, a substituted or unsubstituted phenalenyl group, a substituted or unsubstituted phenanthrenyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted imidazolyl group, a substituted or unsubstituted benzoimidazolyl group, a substituted or unsubstituted phenylbenzoimidazolyl group, a substituted or unsubstituted pyrazolyl group, a substituted or unsubstituted pyridinyl group, a substituted or unsubstituted phenylpyridinyl group, a substituted or unsubstituted phenylimidazopyridinyl group, a substituted or unsubstituted pyrazinyl group, a substituted or unsubstituted pyrimidinyl group, a substituted or unsubstituted phenylimidazopyrimidinyl group, a substituted or unsubstituted pyridazinyl group, a substituted or unsubstituted indolyl group, a substituted or unsubstituted isoindolyl group, a substituted or unsubstituted indazolyl group, a substituted or unsubstituted purinyl group, a substituted or unsubstituted quinolinyl group, a substituted or unsubstituted benzoquinolinyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted cinnolinyl group, a substituted or unsubstituted carbazolyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted furanyl group, a substituted or unsubstituted benzofuranyl group, a substituted or unsubstituted dibenzofuranyl group, a substituted or unsubstituted thiophenyl group, a substituted or unsubstituted benzo[b]thiophenyl group, a substituted or unsubstituted dibenzothiophenyl, a substituted or unsubstituted thiazolyl group, a substituted or unsubstituted isothiazolyl group, a substituted or unsubstituted benzothiazolyl group, a substituted or unsubstituted oxazolyl group, a substituted or unsubstituted isoxazolyl group, a substituted or unsubstituted benzooxazolyl group, a substituted or unsubstituted triazolyl group, a substituted or unsubstituted phenyltriazolyl group, a substituted or unsubstituted tetrazolyl group, a substituted or unsubstituted oxadiazolyl group, a substituted or unsubstituted phenyloxadiazolyl group, a substituted or unsubstituted triazinyl group, a substituted or unsubstituted phenyltriazinyl group, a substituted or unsubstituted diphenylethynyl group, a substituted or unsubstituted phenylethynylfluorenyl group, or a substituted or unsubstituted phenylethynylnaphthyl group, but is not limited thereto.

In particular, $Ar_1$ may be a substituted or unsubstituted phenyl group, a substituted or unsubstituted biphenyl group, a substituted or unsubstituted naphthyl group, a substituted or unsubstituted fluorenyl group, a substituted or unsubstituted phenanthrenyl group, a substituted or unsubstituted anthryl group, a substituted or unsubstituted triphenylrenyl group, a substituted or unsubstituted pyrenyl group, a substituted or unsubstituted imidazolyl group, a substituted or unsubstituted benzoimidazolyl group, a substituted or unsubstituted phenylbenzoimidazolyl group, a substituted or unsubstituted pyridinyl group, a substituted or unsubstituted phenylpyridinyl group, a substituted or unsubstituted phenylimidazopyridinyl group, a substituted or unsubstituted pyrimidinyl group, a substituted or unsubstituted phenylimidazopyrimidinyl group, a substituted or unsubstituted carbazolyl group, a substituted or unsubstituted furanyl group, a substituted or unsubstituted benzofuranyl group, a substituted or unsubstituted dibenzofuranyl group, a substituted or unsubstituted thiophenyl group, a substituted or unsubstituted benzo[b]thiophenyl group, a substituted or unsubstituted dibenzothiophenyl group, a substituted or unsubstituted triazolyl group, a substituted or unsubstituted phenyltriazolyl group, a substituted or unsubstituted oxadiazolyl group, a substituted or unsubstituted phenyloxadiazolyl group, a substituted or unsubstituted triazinyl group, a substituted or unsubstituted phenyltriazinyl group, a diphenylethynyl group, a phenylethynylfluorenyl group, or a phenylethynylnaphthyl group.

For example, $Ar_1$ may be one of the groups represented by Formulae 4A to 4X below:

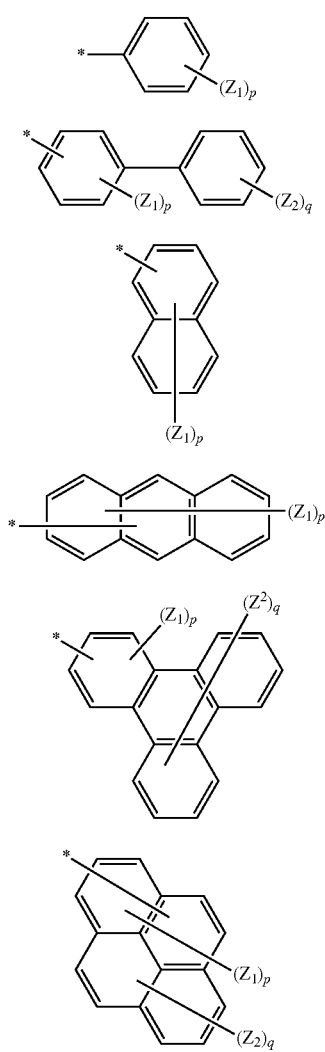

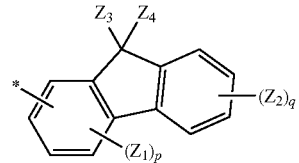

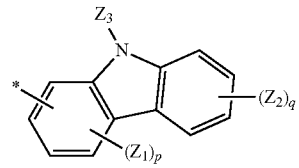

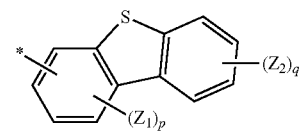

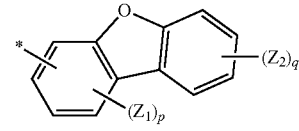

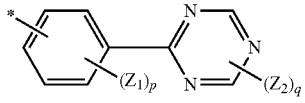

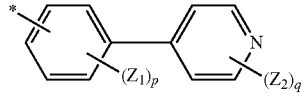

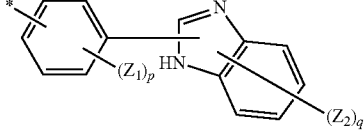

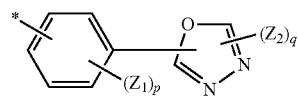

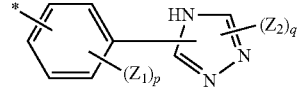

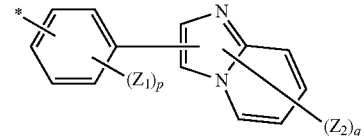

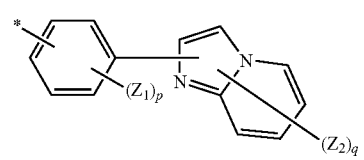

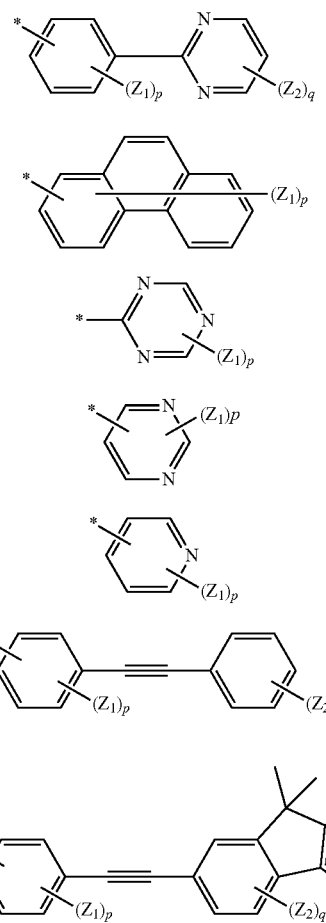

where * indicates a biding site.

Here, $Z_1$, $Z_2$ and $Z_3$ may be each independently a hydrogen atom, a deuterium, a tritium, a halogen atom, a hydroxyl group, a cyano group, a nitro group, a carboxylic group, a silyl group, a substituted or unsubstituted $C_1$-$C_{50}$ alkyl group, a substituted or unsubstituted $C_2$-$C_{50}$ alkenyl group, a substituted or unsubstituted $C_2$-$C_{50}$ alkynyl group, a substituted or unsubstituted $C_1$-$C_{50}$ alkoxy group, a substituted or unsubstituted $C_3$-$C_{50}$ cycloalkyl group, a substituted or unsubstituted $C_3$-$C_{50}$ cycloalkenyl group, a substituted or unsubstituted $C_5$-$C_{60}$ aryl group, a substituted or unsubstituted $C_5$-$C_{60}$ aryloxy group, a substituted or unsubstituted $C_5$-$C_{60}$ arylthio group, a substituted or unsubstituted $C_2$-$C_{60}$ heteroaryl group, a substituted or unsubstituted $C_2$-$C_{60}$ polycyclic condensed group, $N(Q_{11})(Q_{12})$, or $Si(Q_{13})(Q_{14})(Q_{15})$, and p, q, and r may be each independently an integer from 1 to 5. $Q_{11}$ to $Q_{15}$ may be each independently a hydrogen atom, a deuterium, a tritium, a halogen atom, a hydroxyl group, a cyano group, a nitro group, a carboxyl group, a substituted or unsubstituted $C_1$-$C_{50}$ alkyl group, a substituted or unsubstituted $C_2$-$C_{50}$ alkenyl group, a substituted or unsubstituted $C_2$-$C_{50}$ alkynyl group, a substituted or unsubstituted $C_1$-$C_{50}$ alkoxy group, a substituted or unsubstituted $C_3$-$C_{50}$ cycloalkyl group, a substituted or unsubstituted $C_3$-$C_{50}$ cycloalkenyl group, a substituted or unsubstituted $C_5$-$C_{60}$ aryl group, a substituted or unsubstituted $C_5$-$C_{60}$ aryloxy group, a substituted or unsubstituted $C_5$-$C_{60}$ arylthio group, a substituted or unsubstituted $C_2$-$C_{60}$ heteroaryl group, or a substituted or unsubstituted $C_2$-$C_{60}$ polycyclic condensed group.

In the heterocyclic compound represented by Formula 1, X may be

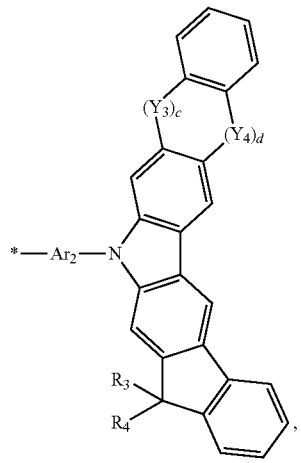

wherein $Ar_2$ may be a substituted or unsubstituted phenylene group, a substituted or unsubstituted biphenylene group, a substituted or unsubstituted pentalenylene group, a substituted or unsubstituted indenylene group, a substituted or unsubstituted naphtylene group, a substituted or unsubstituted fluorenylene group, a substituted or unsubstituted spirofluorenyl group, a substituted or unsubstituted phenalenylene group, a substituted or unsubstituted phenanthrenylene group, a substituted or unsubstituted anthrylene group, a substituted or unsubstituted fluoranthenylene group, a substituted or unsubstituted triphenylenylene group, a substituted or unsubstituted pyrenylene group, a substituted or unsubstituted chrysenylene group, a substituted or unsubstituted carbazolylene group, and a substituted or unsubstituted diphenylethynylene group, but is not limited thereto.

For example, $Ar_2$ may be one of the groups represented by Formulae 5A to 5E below:

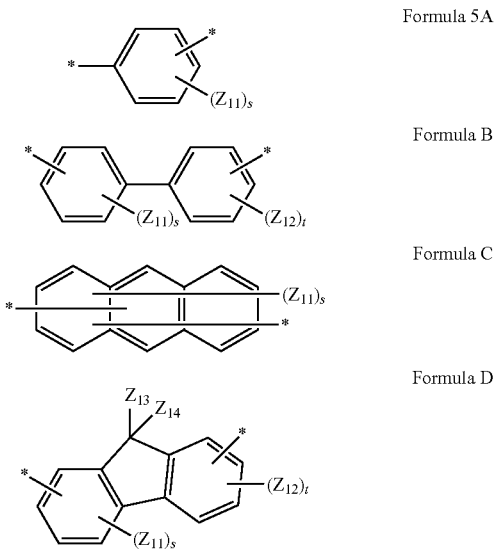

-continued

Formula E

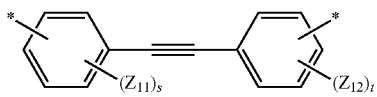

where * indicates a biding site.

Here, $Z_{11}$, $Z_{12}$ and $Z_{13}$ may be each independently a hydrogen atom, a deuterium, a tritium, a halogen atom, a hydroxyl group, a cyano group, a nitro group, a carboxylic group, a silyl group, a substituted or unsubstituted $C_1$-$C_{50}$ alkyl group, a substituted or unsubstituted $C_2$-$C_{50}$ alkenyl group, a substituted or unsubstituted $C_2$-$C_{50}$ alkynyl group, a substituted or unsubstituted $C_1$-$C_{50}$ alkoxy group, a substituted or unsubstituted $C_3$-$C_{50}$ cycloalkyl group, a substituted or unsubstituted $C_3$-$C_{50}$ cycloalkenyl group, a substituted or unsubstituted $C_5$-$C_{60}$ aryl group, a substituted or unsubstituted $C_5$-$C_{60}$ aryloxy group, a substituted or unsubstituted $C_5$-$C_{60}$ arylthio group, a substituted or unsubstituted $C_2$-$C_{60}$ heteroaryl group, a substituted or unsubstituted $C_2$-$C_{60}$ polycyclic condensed group, $N(Q_{11})(Q_{12})$, or $Si(Q_{13})(Q_{14})(Q_{15})$, and p, q, and r may be each independently an integer from 1 to 4. $Q_{11}$ to $Q_{15}$ may be each independently a hydrogen atom, a deuterium, a tritium, a halogen atom, a hydroxyl group, a cyano group, a nitro group, a carboxyl group, a silyl group, a substituted or unsubstituted $C_1$-$C_{50}$ alkyl group, a substituted or unsubstituted $C_2$-$C_{50}$ alkenyl group, a substituted or unsubstituted $C_2$-$C_{50}$ alkynyl group, a substituted or unsubstituted $C_1$-$C_{50}$ alkoxy group, a substituted or unsubstituted $C_3$-$C_{50}$ cycloalkyl group, a substituted or unsubstituted $C_3$-$C_{50}$ cycloalkenyl group, a substituted or unsubstituted $C_5$-$C_{60}$ aryl group, a substituted or unsubstituted $C_5$-$C_{60}$ aryloxy group, a substituted or unsubstituted $C_5$-$C_{60}$ arylthio group, a substituted or unsubstituted $C_2$-$C_{60}$ heteroaryl group, or a substituted or unsubstituted $C_2$-$C_{60}$ polycyclic condensed group.

In the heterocyclic compound represented by Formula 1, $R_1$, $R_2$, $R_3$ and $R_4$ may be each independently a hydrogen atom, a deuterium, a tritium, a halogen atom, a hydroxyl group, a cyano group, a nitro group, a carboxyl group, a silyl group, a substituted or unsubstituted $C_1$-$C_{50}$ alkyl group, and a substituted or unsubstituted $C_5$-$C_{60}$ aryl group, and $Y_1$, $Y_2$, $Y_3$ and $Y_4$ may be each independently $CR_5R_6$, $NR_7$, O, or S. In this regard, $R_5$, $R_6$ and $R_7$ may be each independently a hydrogen atom, a deuterium, a tritium, a halogen atom, a hydroxyl group, a cyano group, a nitro group, a carboxyl group, a silyl group, a substituted or unsubstituted $C_1$-$C_{50}$ alkyl group, or a substituted or unsubstituted $C_5$-$C_{60}$ aryl group.

In the heterocyclic compound represented by Formula 1, $R_1$, $R_2$, $R_3$ and $R_4$ may be each independently a substituted or unsubstituted methyl group, a substituted or unsubstituted ethyl group, a substituted or unsubstituted propyl group, or a substituted or unsubstituted butyl group, and $Y_1$, $Y_2$, $Y_3$ and $Y_4$ may be each independently $CR_5R_6$, $NR_7$, O, or S. Here, $R_5$ and $R_6$ may be each independently a substituted or unsubstituted methyl group, a substituted or unsubstituted ethyl group, a substituted or unsubstituted propyl group, or a substituted or unsubstituted butyl group, and $R_7$ may be a unsubstituted phenyl group, a substituted or unsubstituted biphenyl group, a substituted or unsubstituted naphthyl group, or a substituted or unsubstituted fluorenyl group.

The heterocyclic compound of Formula 1 may be represented by Formula 6 below.

Formula 6

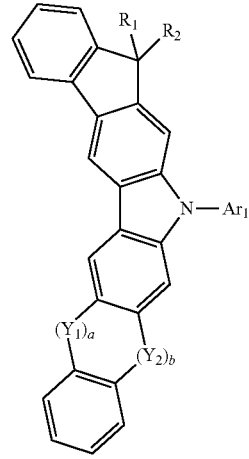

In Formula 6, $Ar_1$ may be a substituted or unsubstituted phenyl group, a substituted or unsubstituted biphenyl group, a substituted or unsubstituted naphthyl group, a substituted or unsubstituted fluorenyl group, a substituted or unsubstituted phenanthrenyl group, a substituted or unsubstituted anthryl group, a substituted or unsubstituted triphenylrenyl group, a substituted or unsubstituted pyrenyl group, a substituted or unsubstituted imidazolyl group, a substituted or unsubstituted benzoimidazolyl group, a substituted or unsubstituted phenylbenzoimidazolyl group, a substituted or unsubstituted pyridinyl group, a substituted or unsubstituted phenylpyridinyl group, a substituted or unsubstituted phenylimidazopyridinyl group, a substituted or unsubstituted pyrimidinyl group, a substituted or unsubstituted phenylimidazopyrimidinyl group, a substituted or unsubstituted carbazolyl group, a substituted or unsubstituted furanyl group, a substituted or unsubstituted benzofuranyl group, a substituted or unsubstituted dibenzofuranyl group, a substituted or unsubstituted thiophenyl group, a substituted or unsubstituted benzo[b]thiophenyl group, a substituted or unsubstituted dibenzothiophenyl group, a substituted or unsubstituted triazolyl group, a substituted or unsubstituted phenyltriazolyl group, a substituted or unsubstituted oxadiazolyl group, a substituted or unsubstituted phenyloxadiazolyl group, a substituted or unsubstituted triazinyl group, a substituted or unsubstituted phenyltriazinyl group, a diphenylethynyl group, a phenylethynylfluorenyl group, or a phenylethynylnaphthyl group; $R_1$ and $R_2$ may be each independently a substituted or unsubstituted methyl group, a substituted or unsubstituted ethyl group, a substituted or unsubstituted propyl group, or a substituted or unsubstituted butyl group; $Y_1$ and $Y_2$ may be each independently $CR_5R_6$, $NR_7$, O, or S; and a and b may be each independently an integer of 0 or 1, wherein a+b=1. Here, $R_5$ and $R_6$ may be each independently a substituted or unsubstituted methyl group, a substituted or unsubstituted ethyl group, a substituted or unsubstituted propyl group, or a substituted or unsubstituted butyl group, and $R_7$ may be a unsubstituted phenyl group, a substituted or unsubstituted biphenyl group, a substituted or unsubstituted naphthyl group, or a substituted or unsubstituted fluorenyl group.

The heterocyclic compound of Formula 1 may be represented by Formula 7 below.

Formula 7
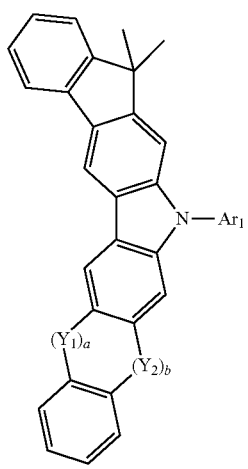
In Formula 7, Ar$_1$ may be one of the groups represented by Formulae 4A to 4X:
Formula 4A
Formula 4B
Formula 4C
Formula 4D
Formula 4E
Formula 4F
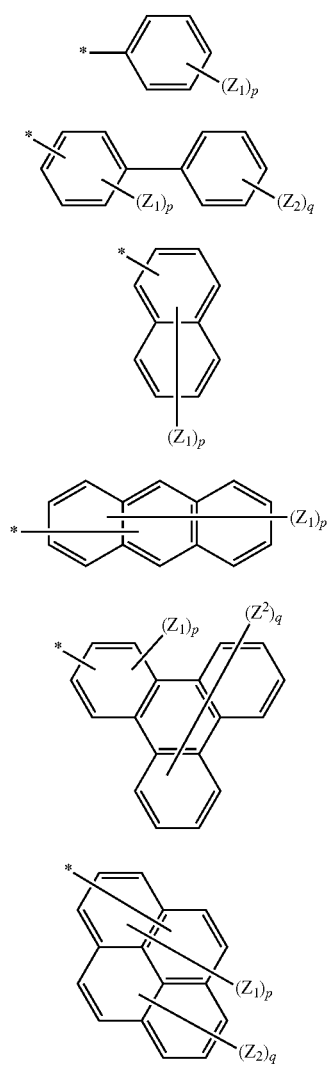
Formula 4G
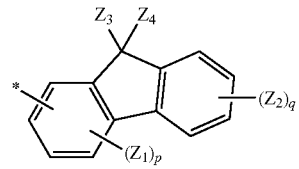
Formula 4H
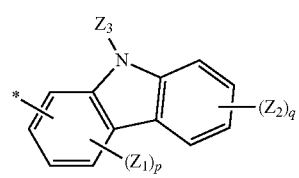
Formula 4I
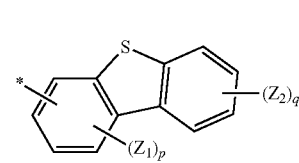
Formula 4J
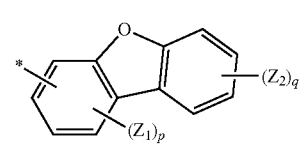
Formula 4K
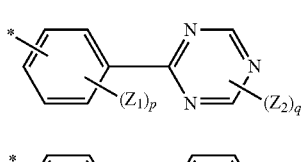
Formula 4L
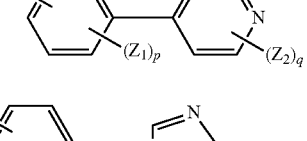
Formula 4M
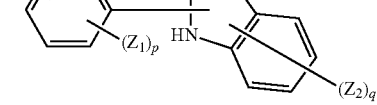
Formula 4N
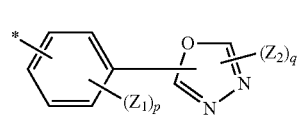
Formula 4O
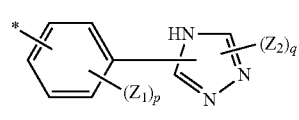
Formula 4P
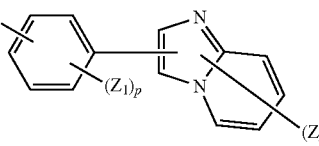
Formula 4Q
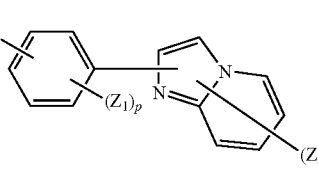

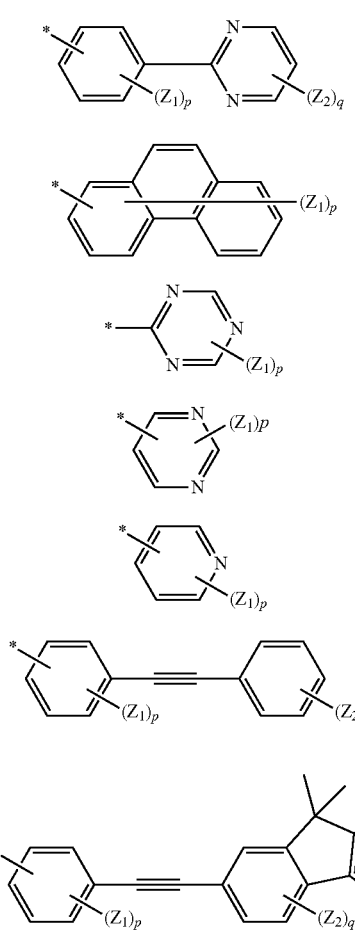

Formula 4R

Formula 4S

Formula 4T

Formula 4U

Formula 4V

Formula 4W

Formula 4X where * indicates a biding site.

$Y_1$ and $Y_2$ may be each independently $CR_5R_6$, $NR_7$, O, or S, and a and b may be each independently an integer of 0 or 1, wherein a+b=1.

In Formulae 4A to 4X, $Z_1$, $Z_2$ and $Z_3$ may be each independently a hydrogen atom, a deuterium, a tritium, a halogen atom, a hydroxyl group, a cyano group, a nitro group, a carboxylic group, a silyl group, a substituted or unsubstituted $C_1$-$C_{50}$ alkyl group, a substituted or unsubstituted $C_2$-$C_{50}$ alkenyl group, a substituted or unsubstituted $C_2$-$C_{50}$ alkynyl group, a substituted or unsubstituted $C_1$-$C_{50}$ alkoxy group, a substituted or unsubstituted $C_3$-$C_{50}$ cycloalkyl group, a substituted or unsubstituted $C_3$-$C_{50}$ cycloalkenyl group, a substituted or unsubstituted $C_5$-$C_{60}$ aryl group, a substituted or unsubstituted $C_5$-$C_{60}$ aryloxy group, a substituted or unsubstituted $C_5$-$C_{60}$ arylthio group, a substituted or unsubstituted $C_2$-$C_{60}$ heteroaryl group, a substituted or unsubstituted $C_2$-$C_{60}$ polycyclic condensed group, $N(Q_{11})(Q_{12})$, or $Si(Q_{13})(Q_{14})(Q_{15})$, and p, q, and r may be each independently an integer from 1 to 5. $Q_{11}$ to $Q_{15}$ are each independently a hydrogen atom, a deuterium, a tritium, a halogen atom, a hydroxyl group, a cyano group, a nitro group, a carboxyl group, a substituted or unsubstituted $C_1$-$C_{50}$ alkyl group, a substituted or unsubstituted $C_2$-$C_{50}$ alkenyl group, a substituted or unsubstituted $C_2$-$C_{50}$ alkynyl group, a substituted or unsubstituted $C_1$-$C_{50}$ alkoxy group, a substituted or unsubstituted $C_3$-$C_{50}$ cycloalkyl group, a substituted or unsubstituted $C_3$-$C_{50}$ cycloalkenyl group, a substituted or unsubstituted $C_5$-$C_{60}$ aryl group, a substituted or unsubstituted $C_5$-$C_{60}$ aryloxy group, a substituted or unsubstituted $C_5$-$C_{60}$ arylthio group, a substituted or unsubstituted $C_2$-$C_{60}$ heteroaryl group, or a substituted or unsubstituted $C_2$-$C_{60}$ polycyclic condensed group. Here, $R_5$ and $R_6$ may be each independently a substituted or unsubstituted methyl group, a substituted or unsubstituted ethyl group, a substituted or unsubstituted propyl group, or a substituted or unsubstituted butyl group, and $R_7$ may be a unsubstituted phenyl group, a substituted or unsubstituted biphenyl group, a substituted or unsubstituted naphthyl group, or a substituted or unsubstituted fluorenyl group.

The heterocyclic compound of Formula 1 may be represented by Formula 8 below.

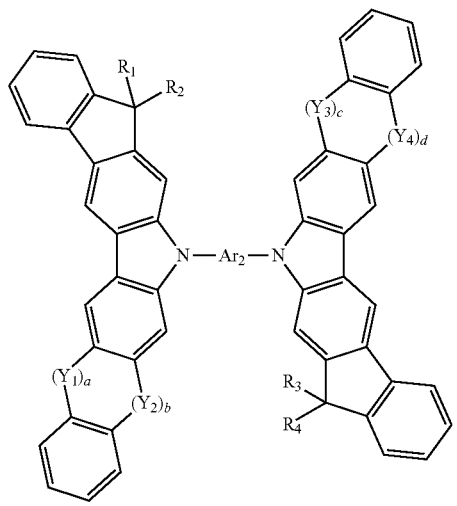

Formula 8

In Formula 8, $Ar_2$ may be a substituted or unsubstituted phenylene group, a substituted or unsubstituted biphenylene group, a substituted or unsubstituted pentarenylene group, a substituted or unsubstituted indenylene group, a substituted or unsubstituted naphthylene group, a substituted or unsubstituted fluorenylene group, a substituted or unsubstituted spiro-fluorenyl group, a substituted or unsubstituted phenalenyl group, a substituted or unsubstituted phenanthrenyl group, a substituted or unsubstituted anthrylene group, a substituted or unsubstituted fluorantenylene group, a substituted or unsubstituted triphenylenylene group, a substituted or unsubstituted pyrenylene group, a substituted or unsubstituted chrycenylene group, a substituted or unsubstituted carbazolylene group, and a substituted or unsubstituted diphenylethynylene group, $R_1$, $R_2$, $R_3$ and $R_4$ may be each independently a substituted or unsubstituted methyl group, a substituted or unsubstituted ethyl group, a substituted or unsubstituted propyl group, or a substituted or unsubstituted butyl group, $Y_1$, $Y_2$, $Y_3$ and $Y_4$ may be each independently $CR_5R_6$, $NR_7$, O, or S, and a, b, c and d may be each independently an integer of 0 or 1, wherein a+b=1 and c+d=1.

Here, $R_5$ and $R_6$ may be each independently a substituted or unsubstituted methyl group, a substituted or unsubstituted ethyl group, a substituted or unsubstituted propyl group, or a substituted or unsubstituted butyl group, and $R_7$ may be a unsubstituted phenyl group, a substituted or unsubstituted biphenyl group, a substituted or unsubstituted naphthyl group, or a substituted or unsubstituted fluorenyl group.

The heterocyclic compound of Formula 1 may be represented by Formula 9 below.

Formula 9

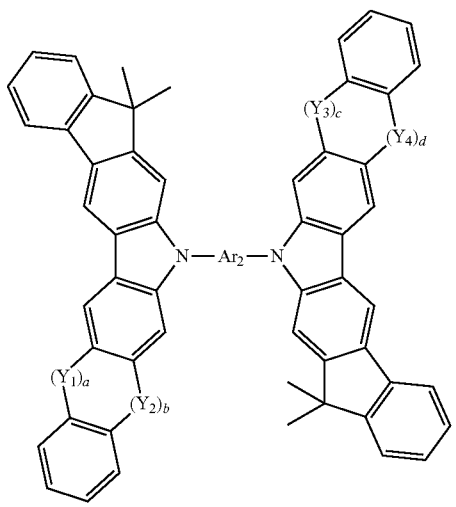

In Formula 9, Ar$_2$ may be one of the groups represented by Formulae 5A to 4X:

Formula 5A

*—⟨Z$_{11}$⟩$_s$—*

Formula 5B

*—⟨Z$_{11}$⟩$_s$—⟨Z$_{12}$⟩$_t$—*

Formula 5C

*—(naphthalene with (Z$_{11}$)$_s$)—*

Formula 5D

*—⟨Z$_{11}$⟩$_s$—C(Z$_{13}$)(Z$_{14}$)—⟨Z$_{12}$⟩$_t$—*

Formula 5E

*—⟨Z$_{11}$⟩$_s$—C≡C—⟨Z$_{12}$⟩$_t$—*

Y$_1$, Y$_2$, Y$_3$, and Y$_4$ are each independently CR$_5$R$_6$, NR$_7$, O, or S, and a, b, c and d are each independently an integer of 0 or 1, wherein a+b=1 and c+d=1.

In Formulae 5A to 5E, Z$_{11}$, Z$_{12}$ and Z$_{13}$ may be each independently a hydrogen atom, a deuterium, a tritium, a halogen atom, a hydroxyl group, a cyano group, a nitro group, a carboxylic group, a silyl group, a substituted or unsubstituted C$_1$-C$_{50}$ alkyl group, a substituted or unsubstituted C$_2$-C$_{50}$ alkenyl group, a substituted or unsubstituted C$_2$-C$_{50}$ alkynyl group, a substituted or unsubstituted C$_1$-C$_{50}$ alkoxy group, a substituted or unsubstituted C$_3$-C$_{50}$ cycloalkyl group, a substituted or unsubstituted C$_3$-C$_{50}$ cycloalkenyl group, a substituted or unsubstituted C$_5$-C$_{60}$ aryl group, a substituted or unsubstituted C$_5$-C$_{60}$ aryloxy group, a substituted or unsubstituted C$_5$-C$_{60}$ arylthio group, a substituted or unsubstituted C$_2$-C$_{60}$ heteroaryl group, a substituted or unsubstituted C$_2$-C$_{60}$ polycyclic condensed group, N(Q$_{11}$)(Q$_{12}$), or Si(Q$_{13}$)(Q$_{14}$)(Q$_{15}$), and p, q, and r may be each independently an integer from 1 to 4. Q$_{11}$ to Q$_{15}$ are each independently a hydrogen atom, a deuterium, a tritium, a halogen atom, a hydroxyl group, a cyano group, a nitro group, a carboxyl group, a silyl group, a substituted or unsubstituted C$_1$-C$_{50}$ alkyl group, a substituted or unsubstituted C$_2$-C$_{50}$ alkenyl group, a substituted or unsubstituted C$_2$-C$_{50}$ alkynyl group, a substituted or unsubstituted C$_1$-C$_{50}$ alkoxy group, a substituted or unsubstituted C$_3$-C$_{50}$ cycloalkyl group, a substituted or unsubstituted C$_3$-C$_{50}$ cycloalkenyl group, a substituted or unsubstituted C$_5$-C$_{60}$ aryl group, a substituted or unsubstituted C$_5$-C$_{60}$ aryloxy group, a substituted or unsubstituted C$_5$-C$_{60}$ arylthio group, a substituted or unsubstituted C$_2$-C$_{60}$ heteroaryl group, or a substituted or unsubstituted C$_2$-C$_{60}$ polycyclic condensed group. Here, R$_5$ and R$_6$ may be each independently a substituted or unsubstituted methyl group, a substituted or unsubstituted ethyl group, a substituted or unsubstituted propyl group, or a substituted or unsubstituted butyl group, and R$_7$ may be a unsubstituted phenyl group, a substituted or unsubstituted biphenyl group, a substituted or unsubstituted naphthyl group, or a substituted or unsubstituted fluorenyl group.

The heterocyclic compound represented by Formula 1 may be any one of Compounds 1 to 83 below, but is not limited thereto.

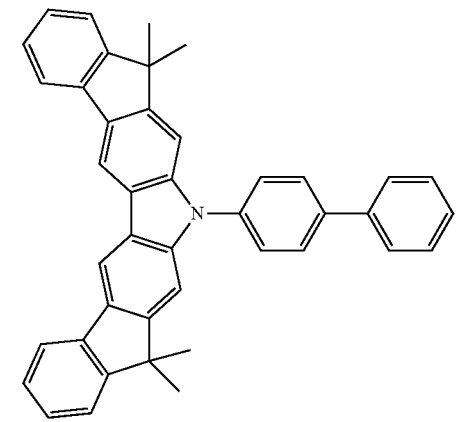

1

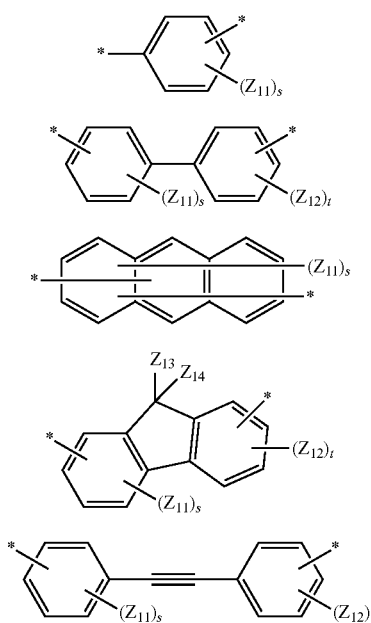

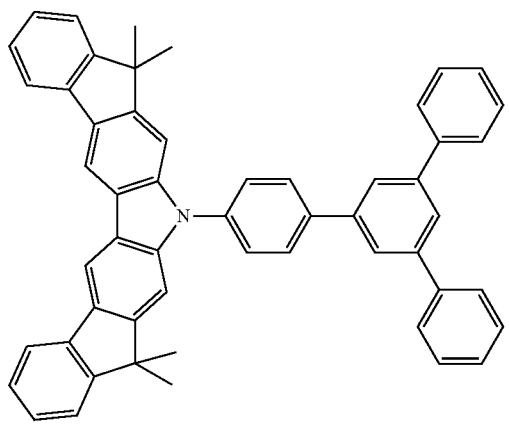

2

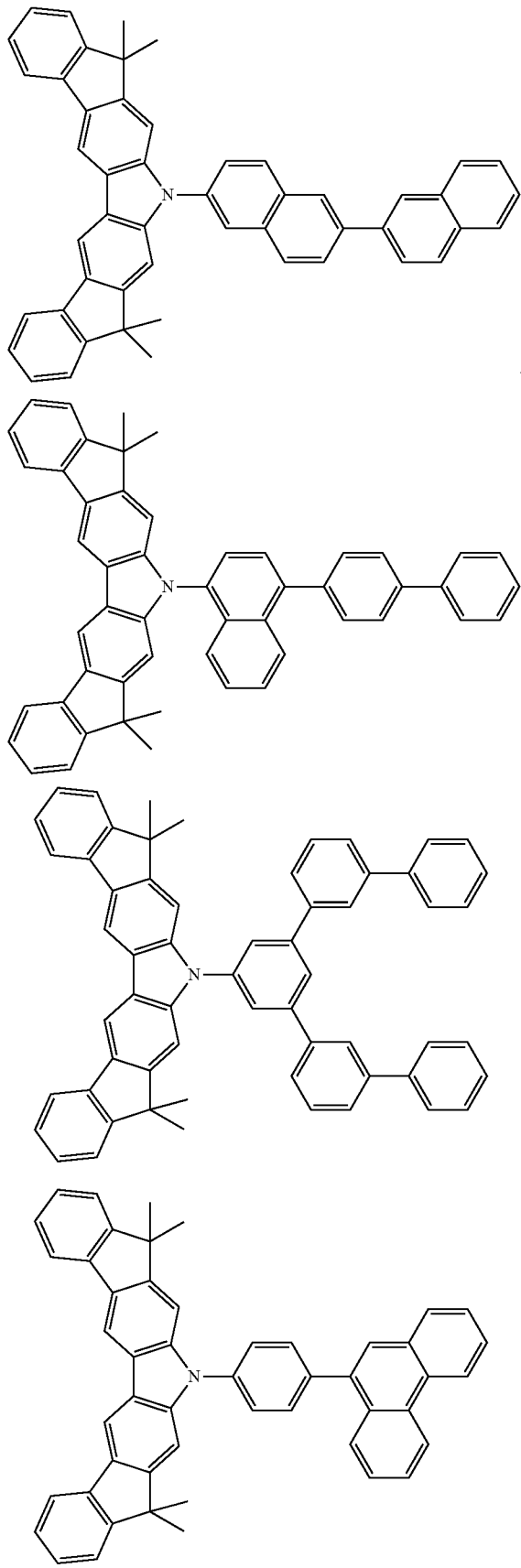
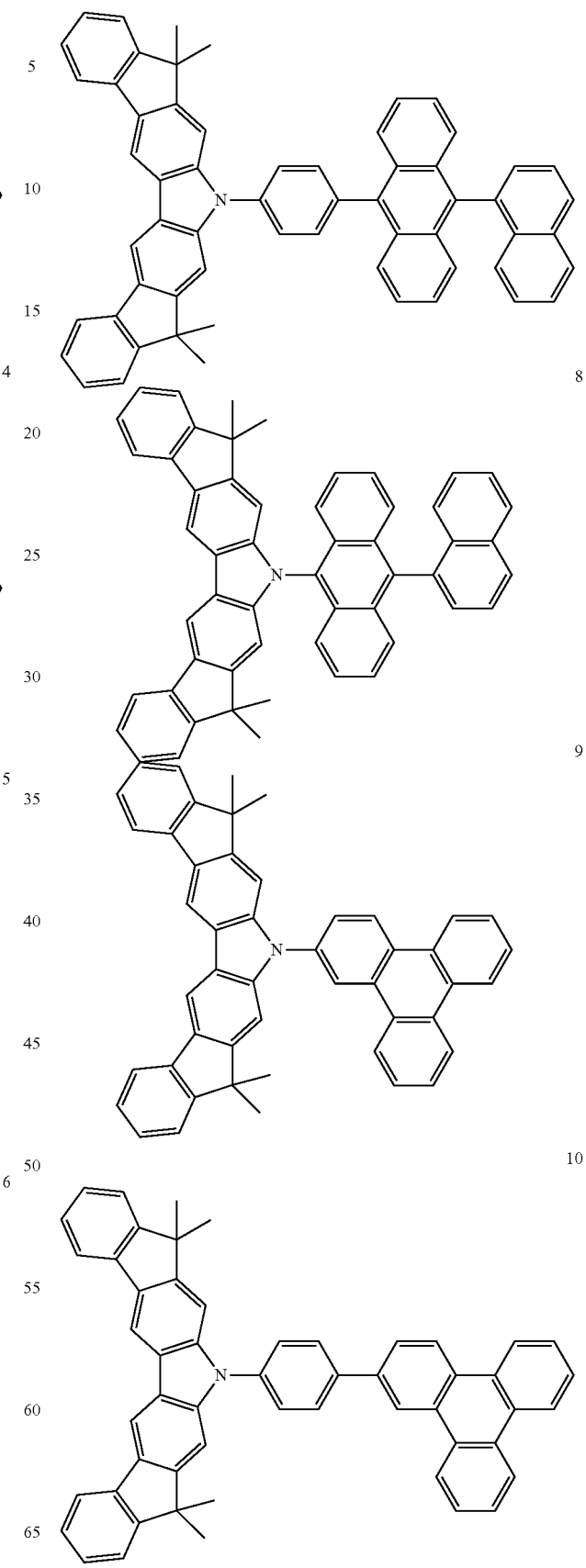

11
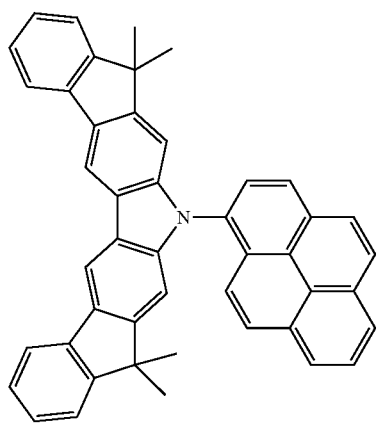
12
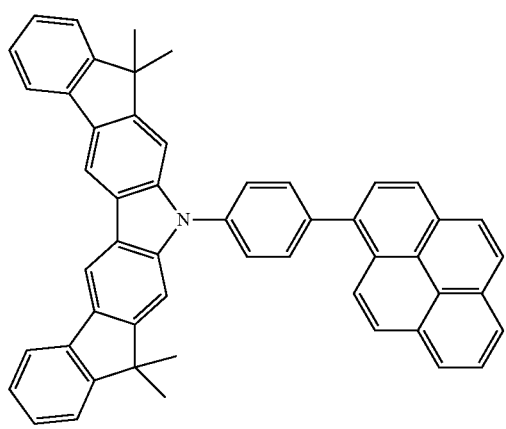
13
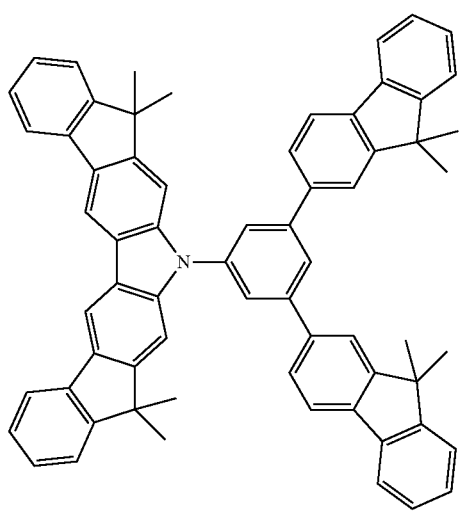
14
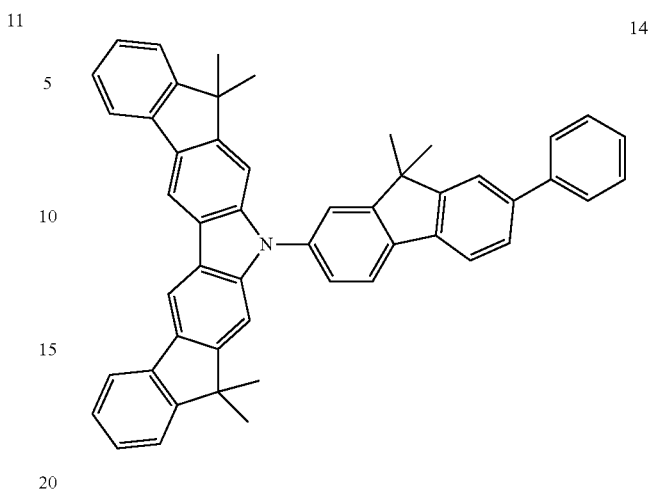
15
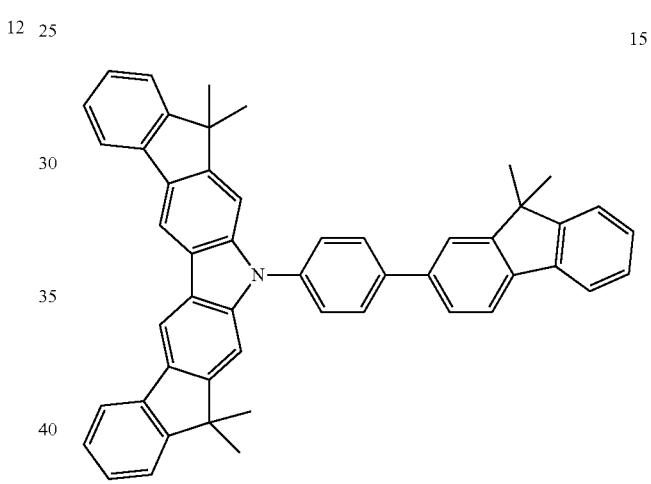
16
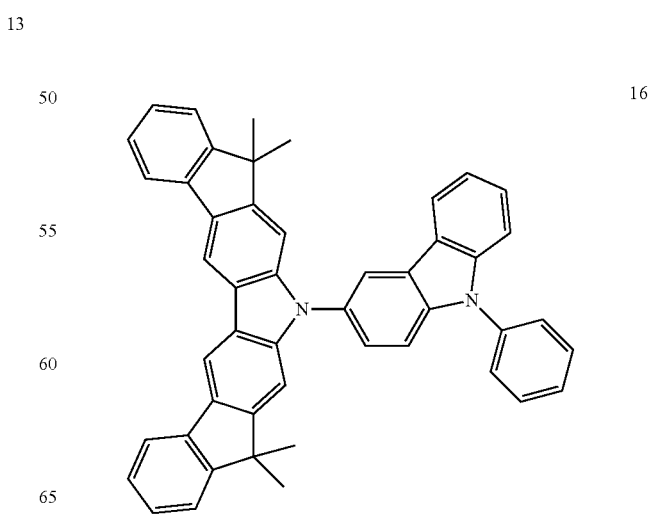

17
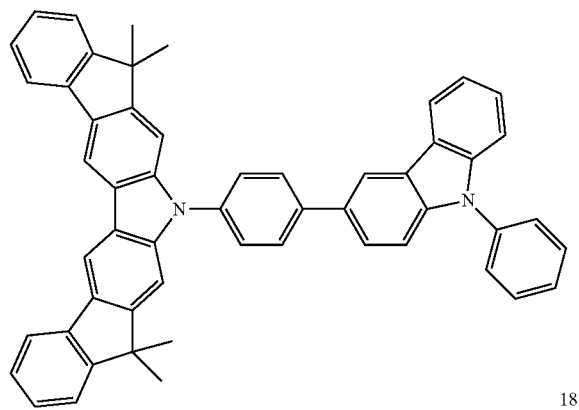
18
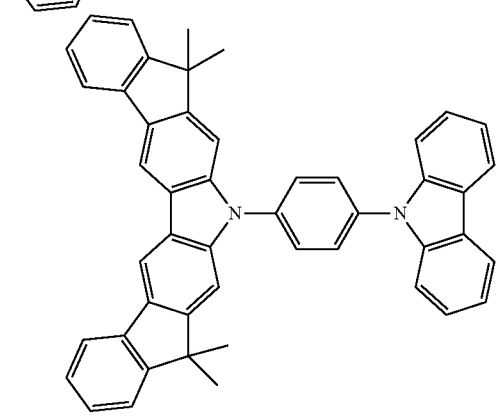
19
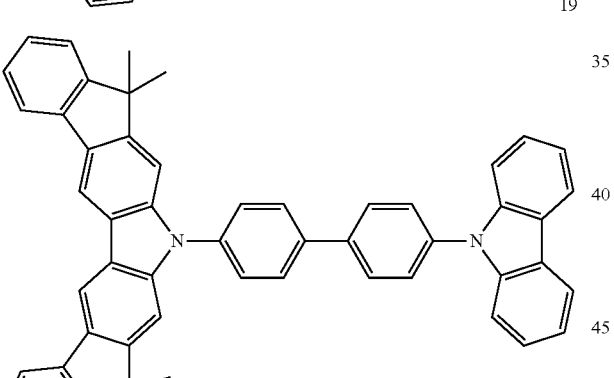
20
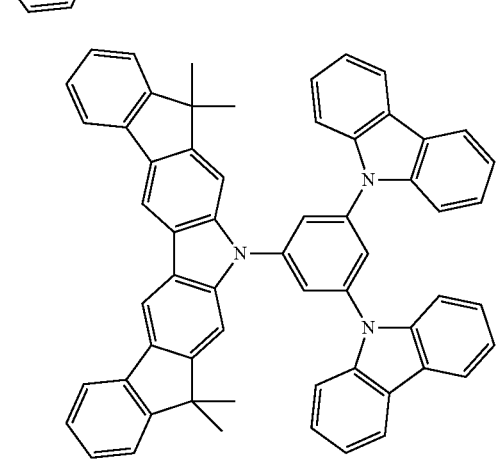
21
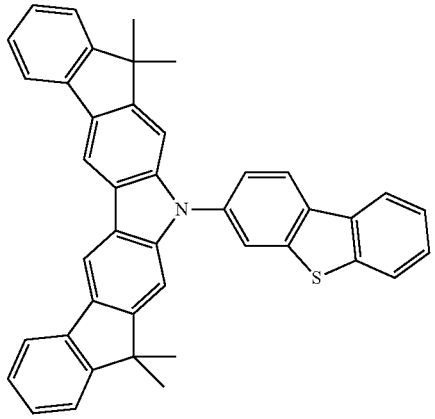
22
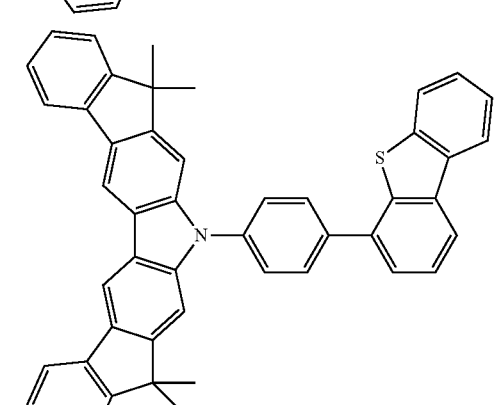
23
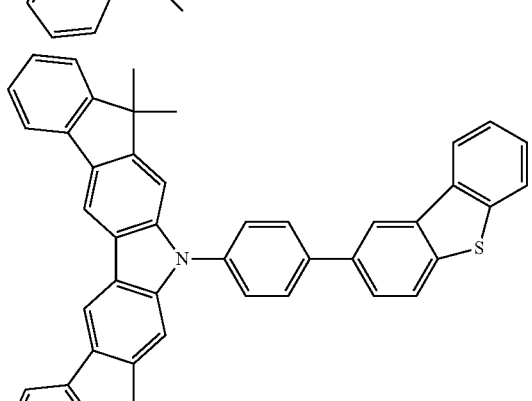
24
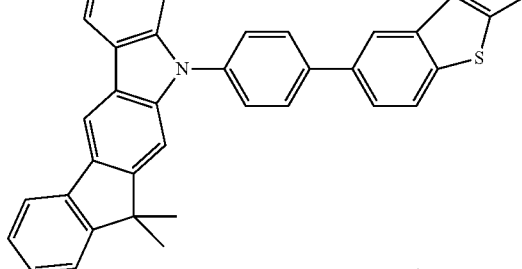

25
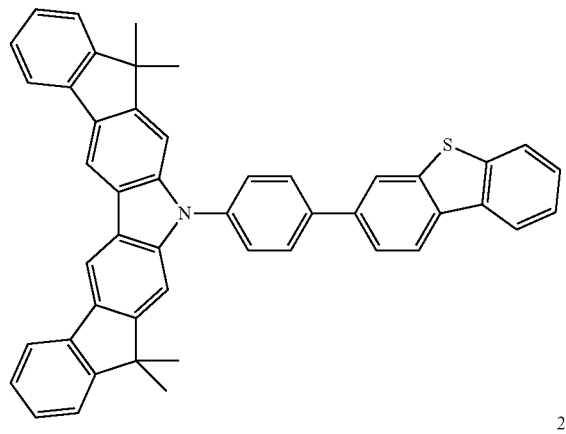
26
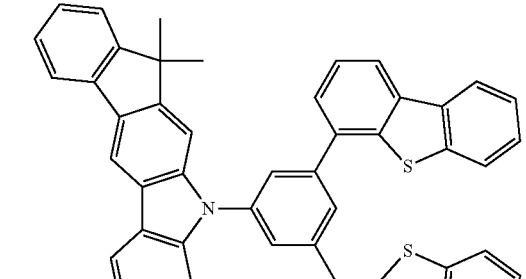
27
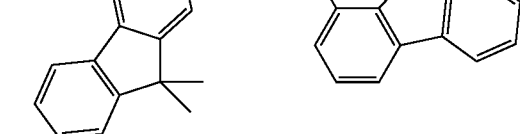
28
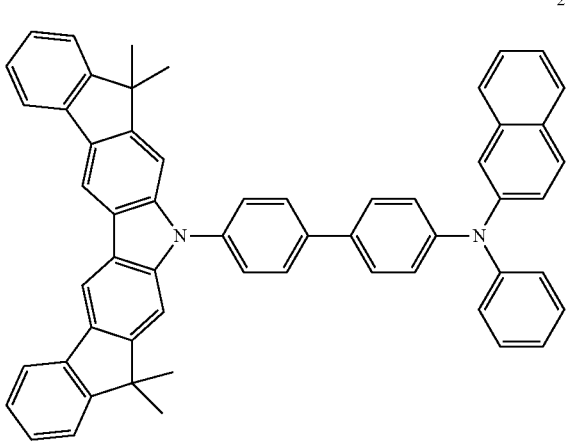
29
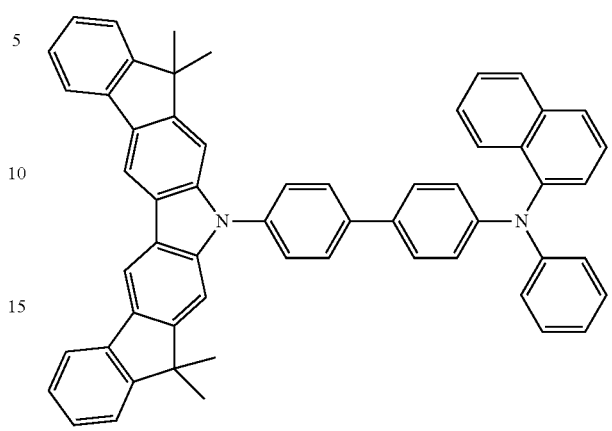
30
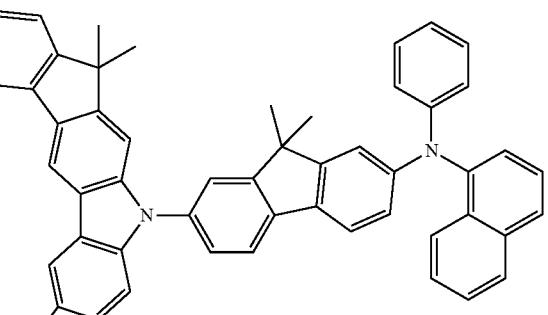
31
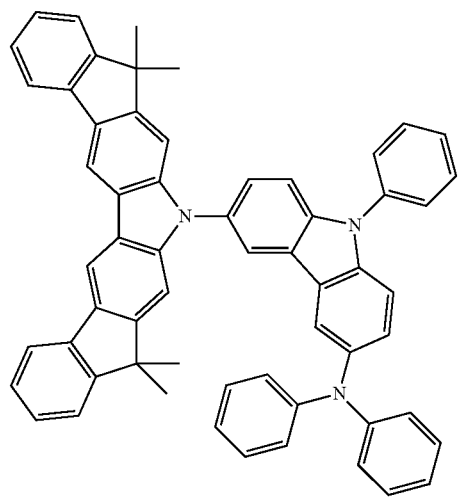

32
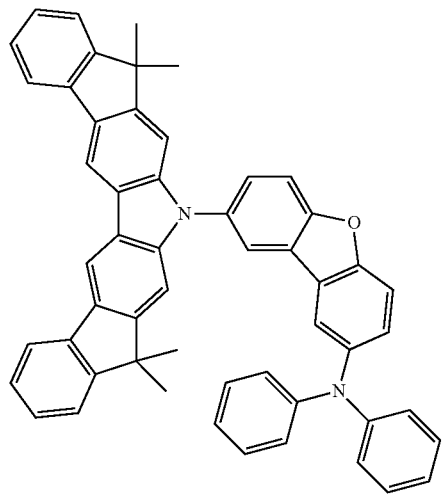
33
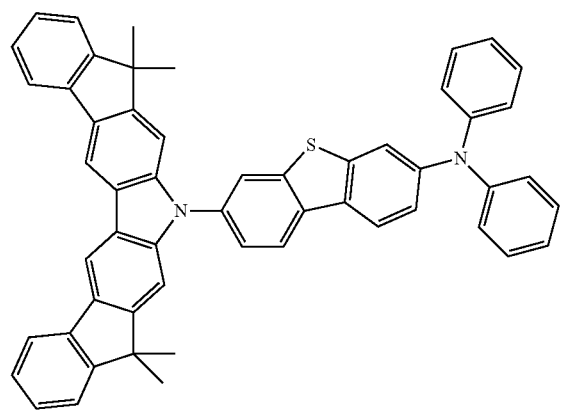
34
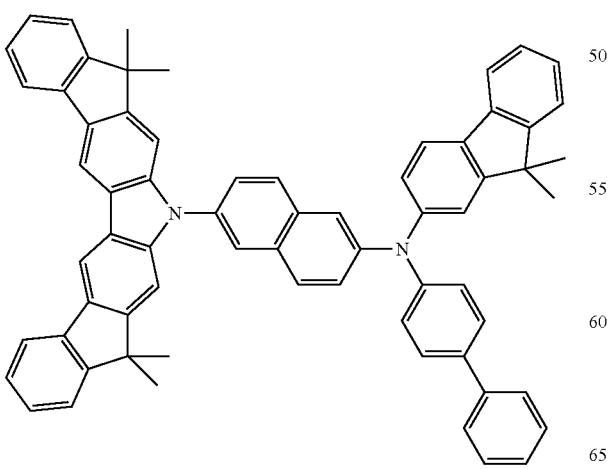
35
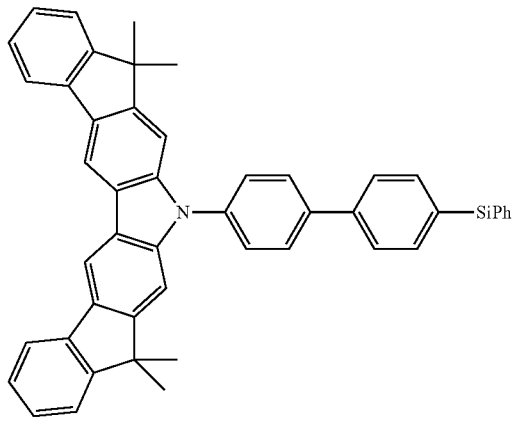
36
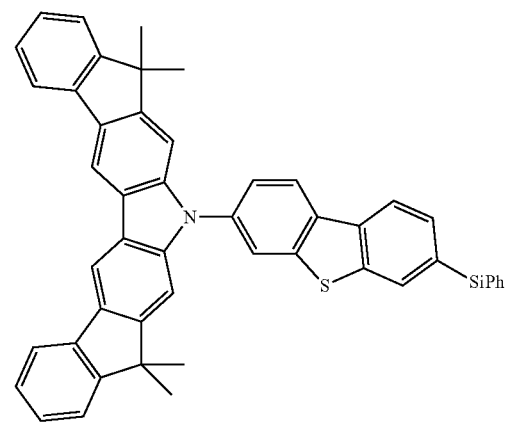
37
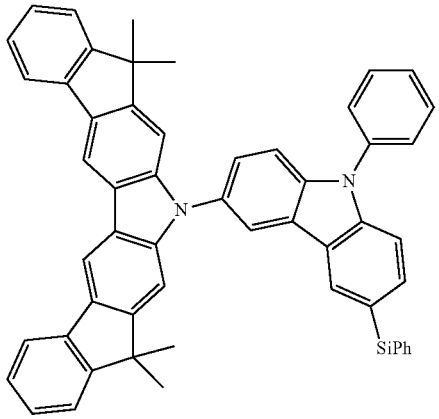

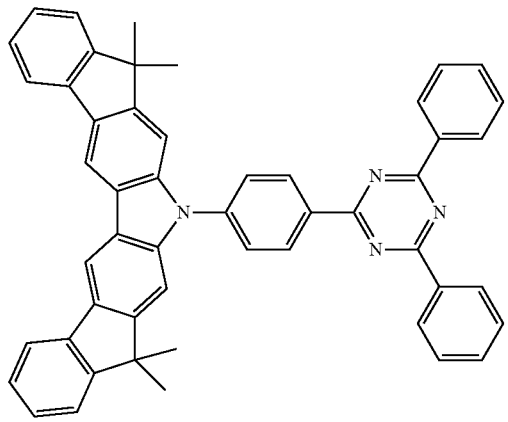
38
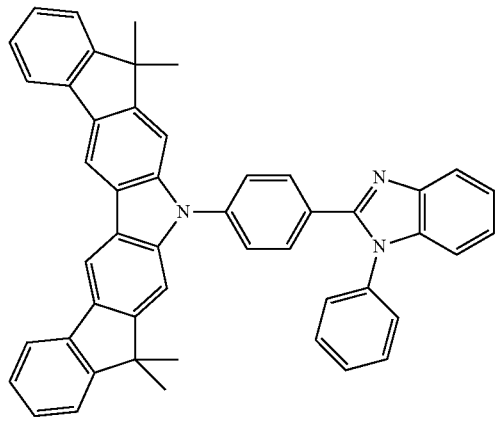
41
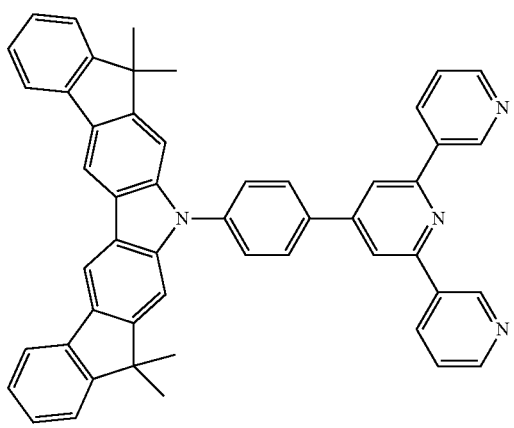
39
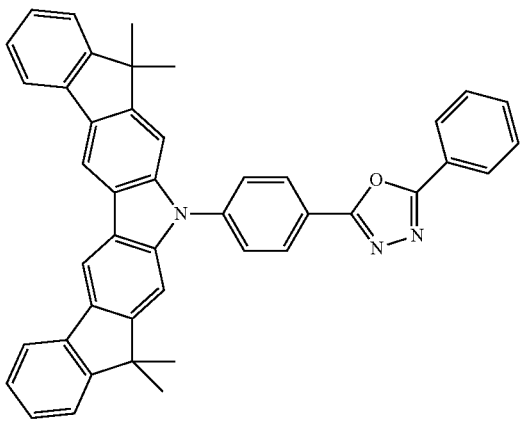
42
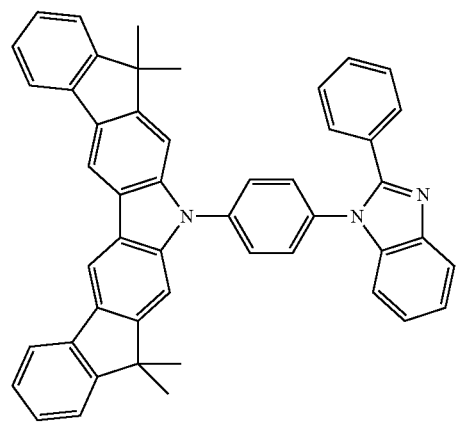
40
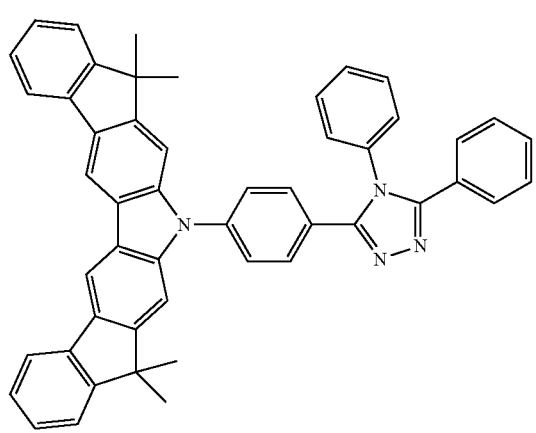
43

44
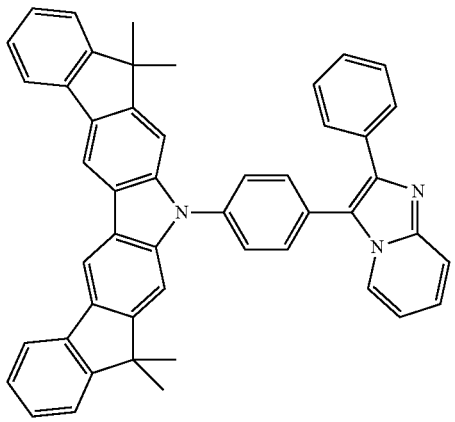
45
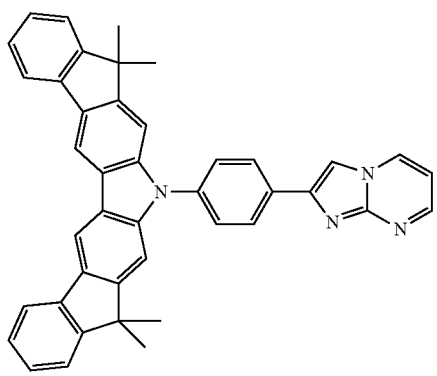
46
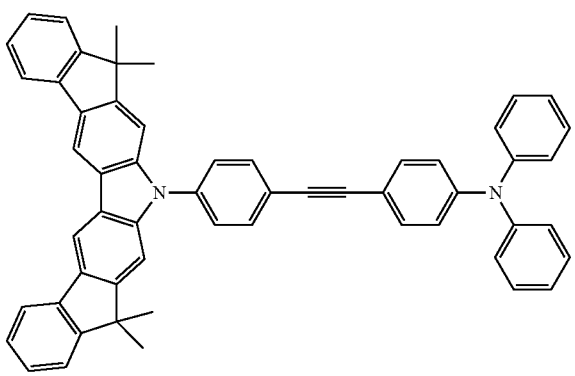
47
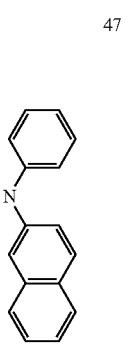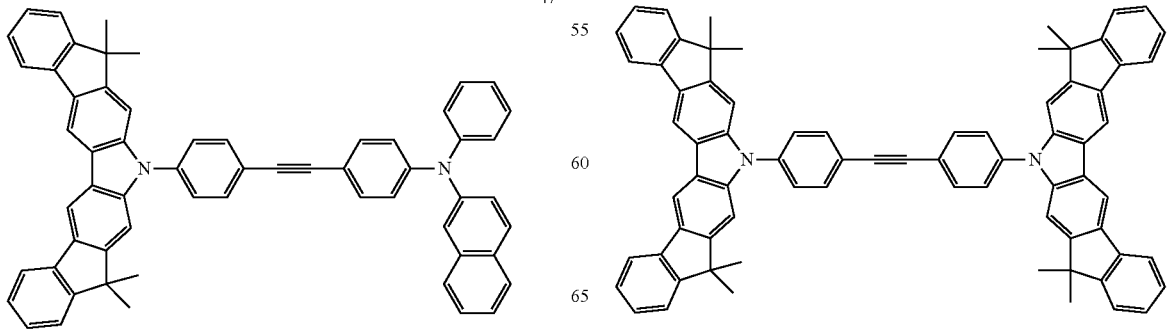
48
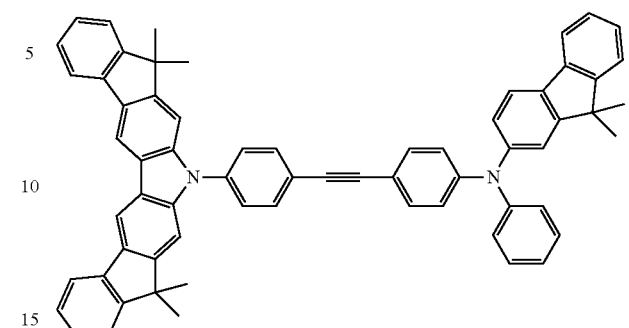
49
50
51
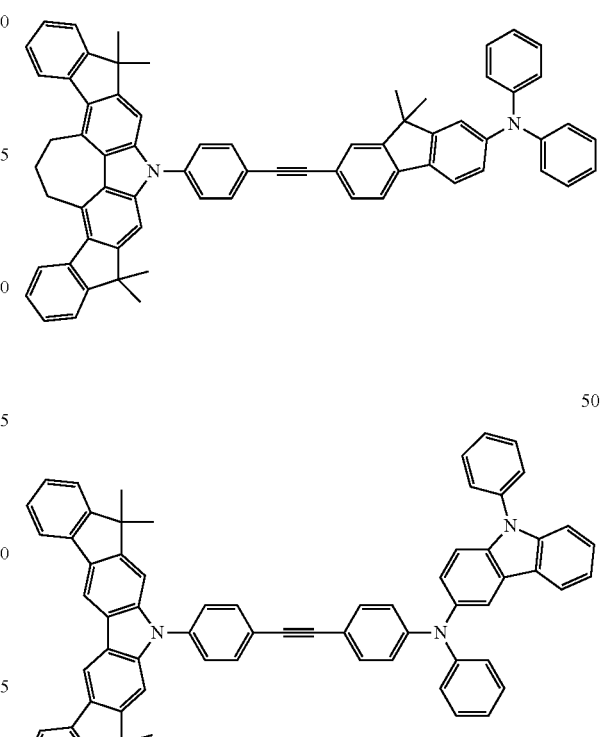

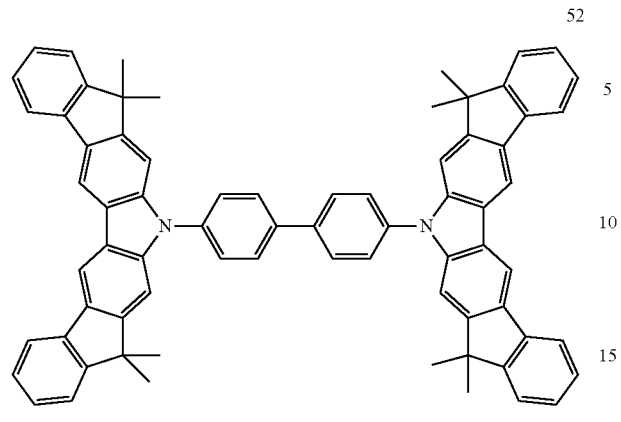
52
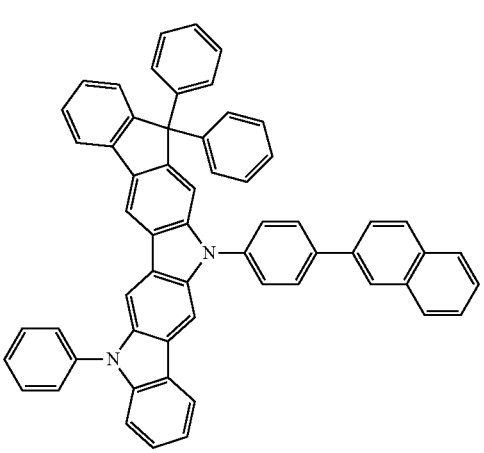
56
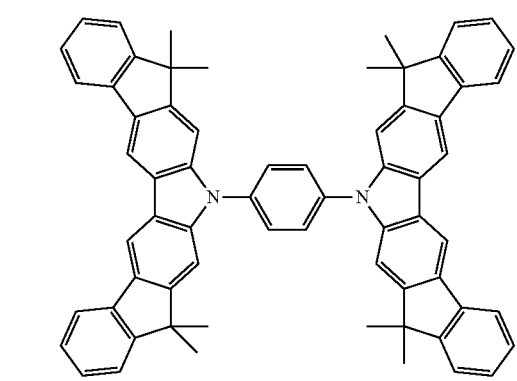
53
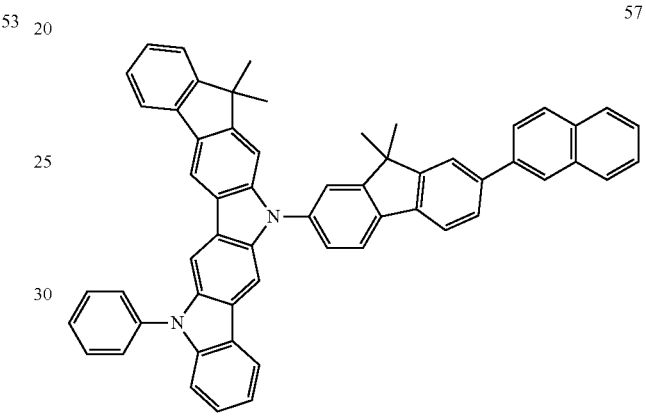
57
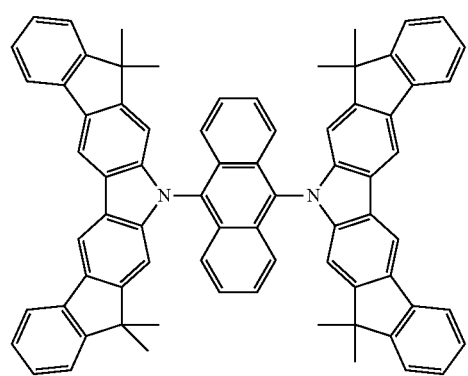
54
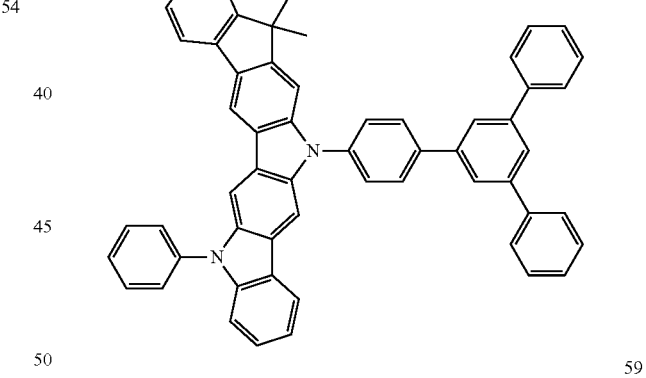
58
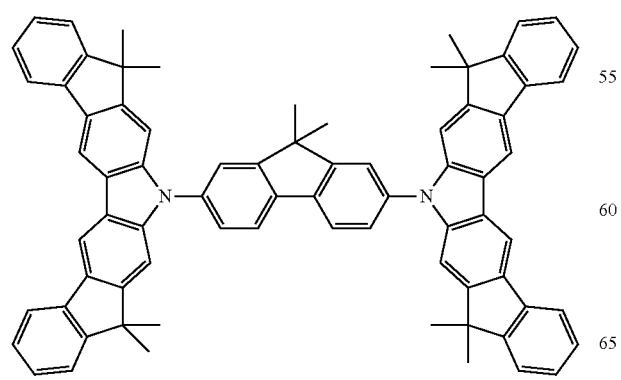
55
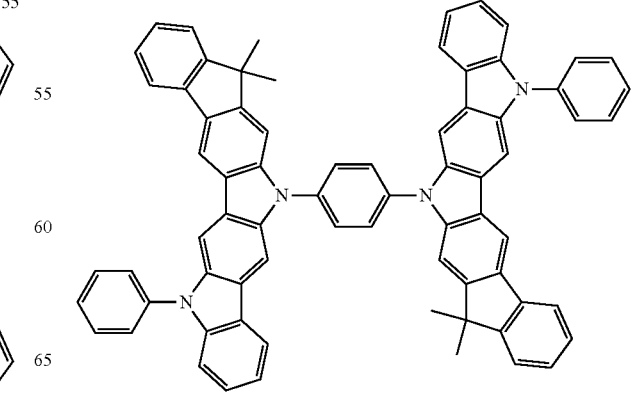
59

60
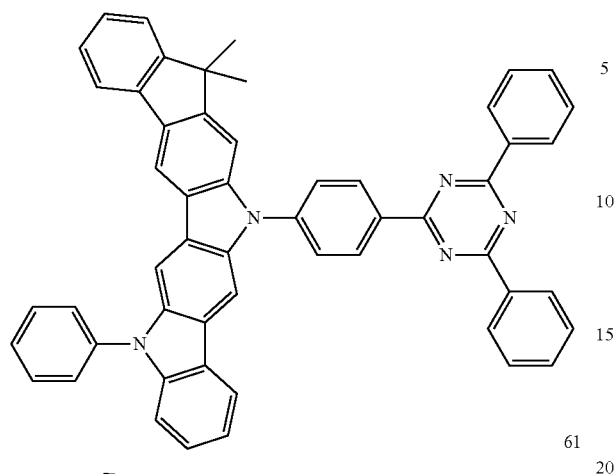
61
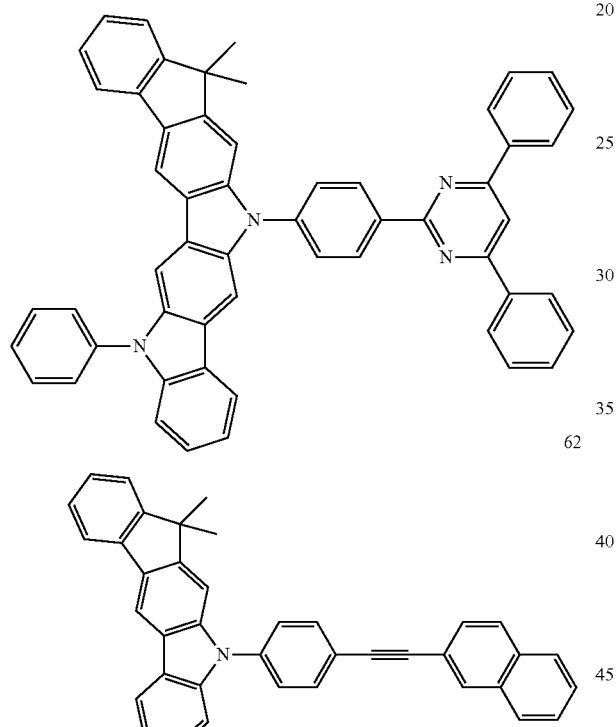
62
64
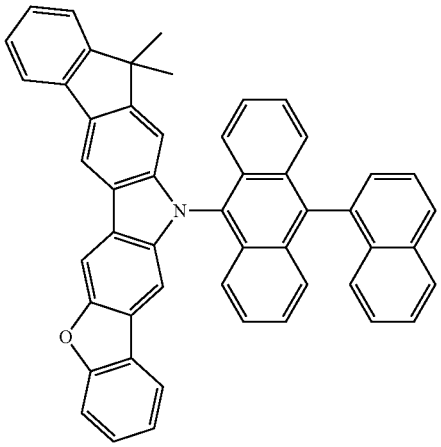
65
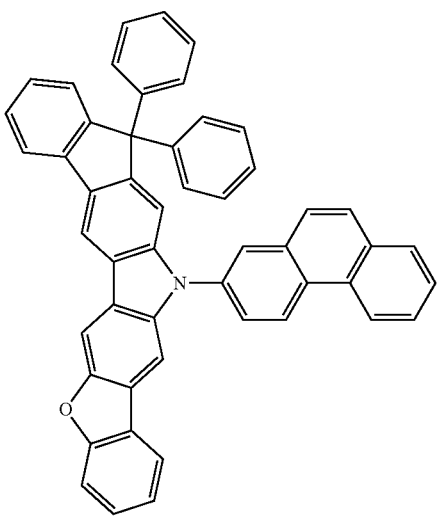
63
66

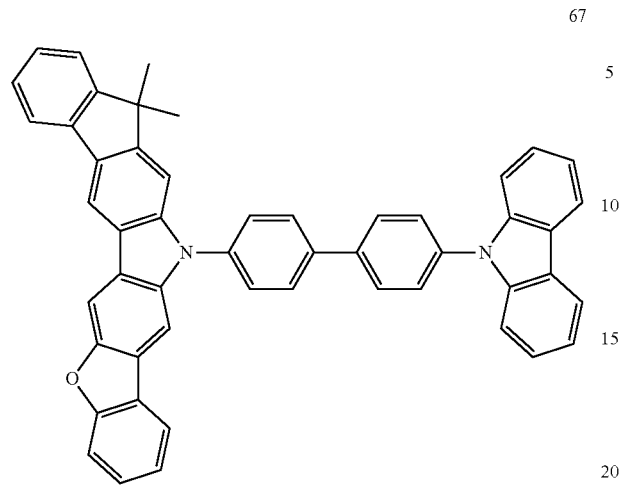
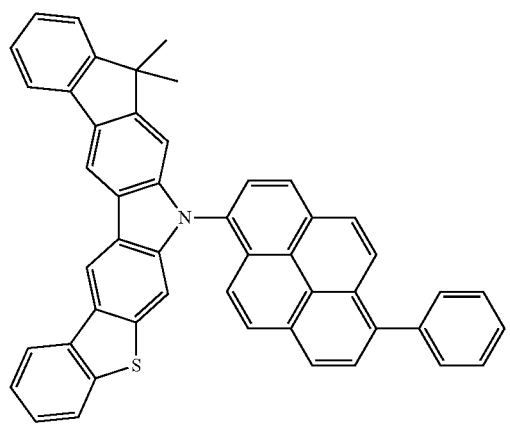
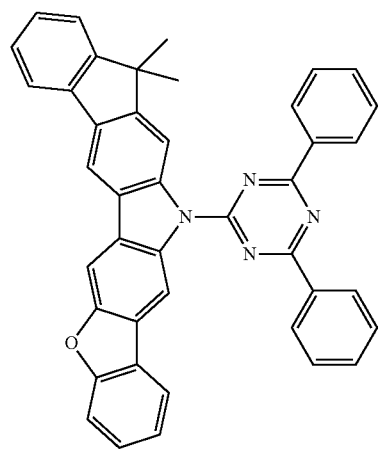
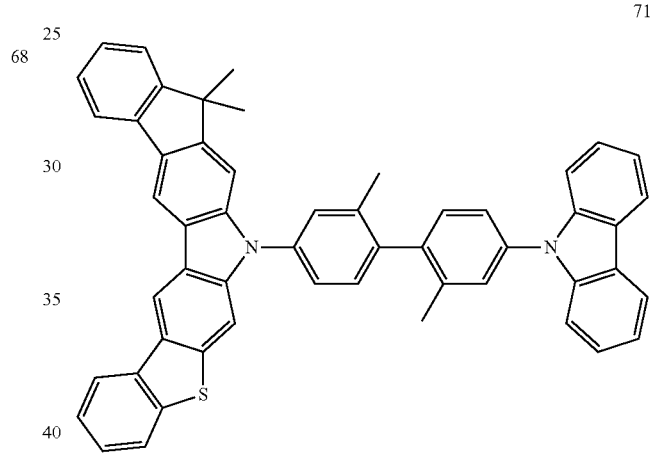
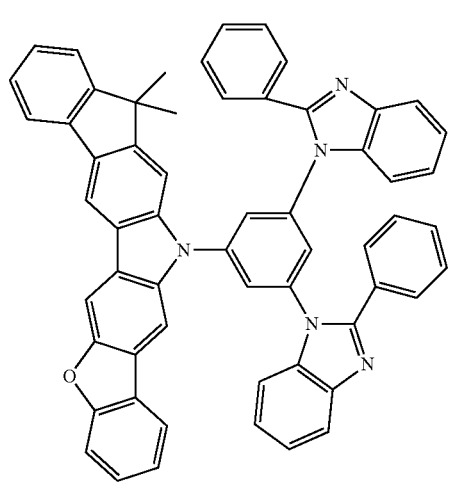
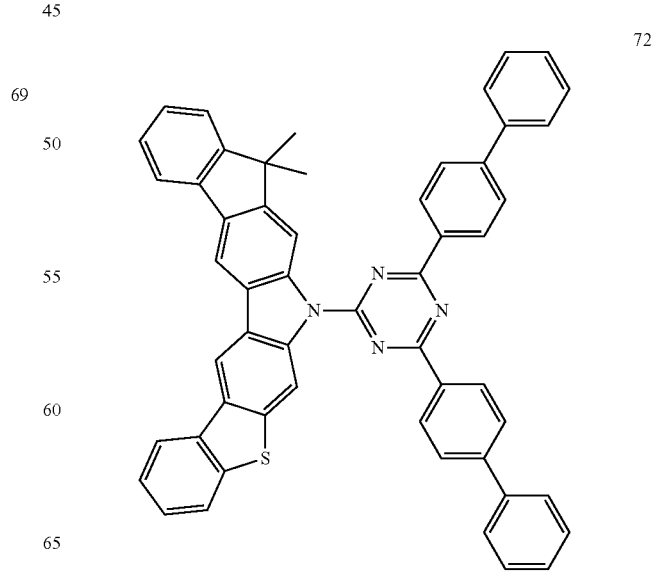

73
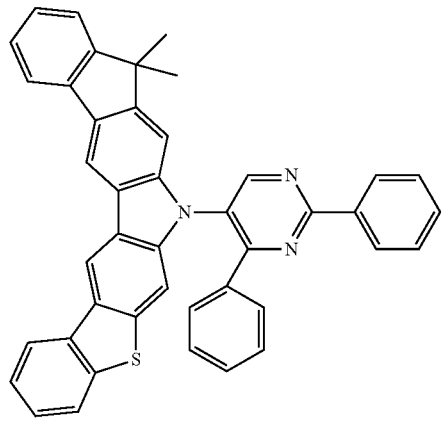
74
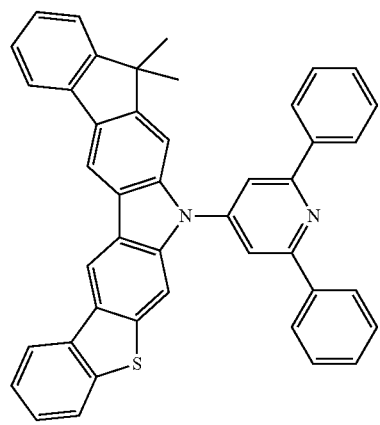
75
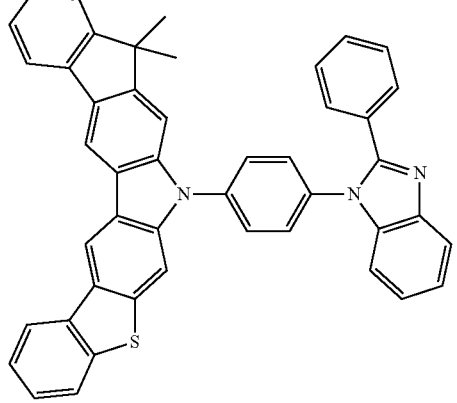
76
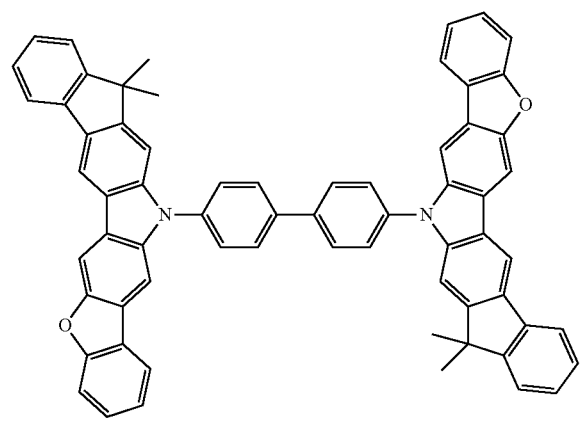
77
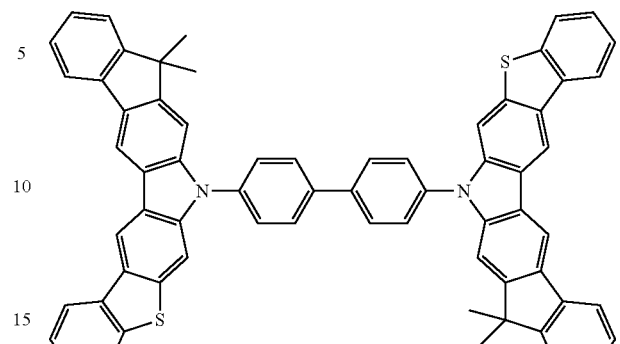
78
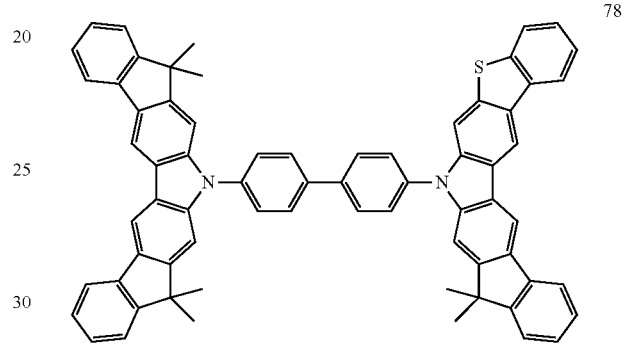
79
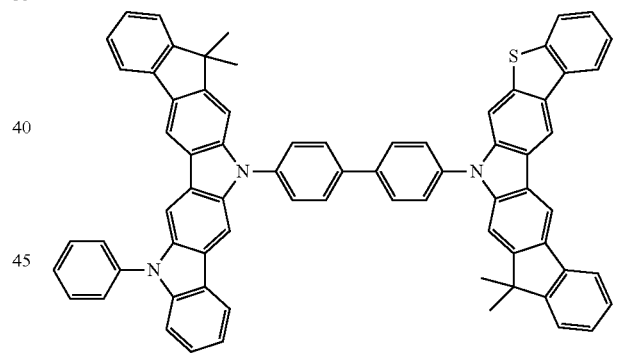
80
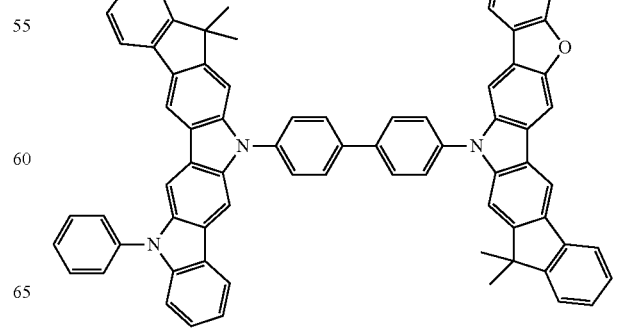

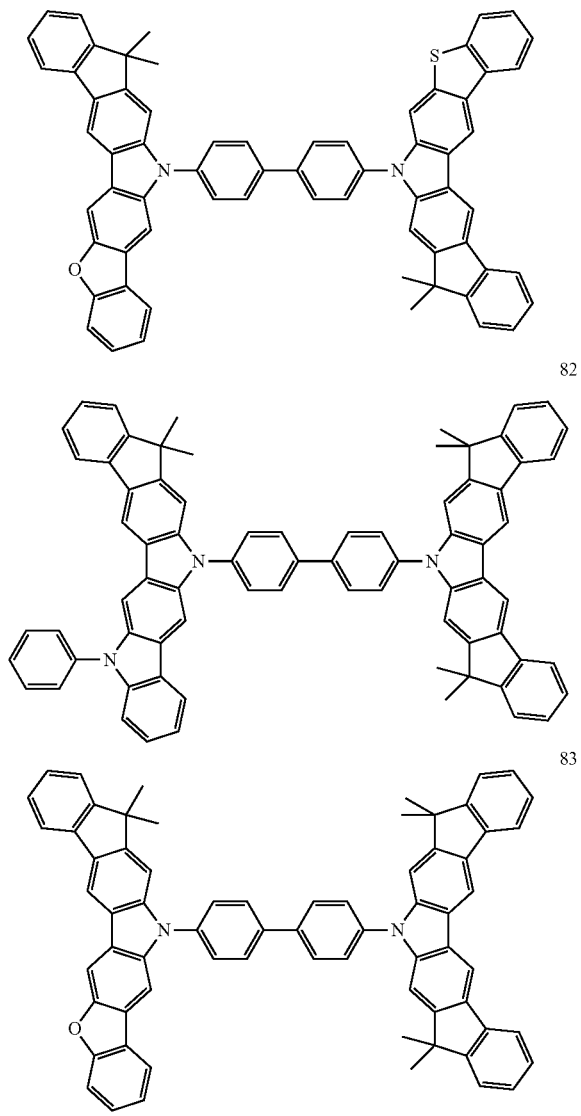

The term "substituted A" in the "a substituted or unsubstituted A (A is any substituent)" used herein refers to A in which at least one hydrogen atom is substituted with a deuterium, a tritium, a halogen atom, a hydroxyl group, a cyano group, a nitro group, a carboxyl group, a silyl group, or a salt derivative thereof, a sulfonic acid group or a salt derivative thereof, a phosphoric acid group or a salt derivative thereof, a $C_1$-$C_{50}$ alkyl group, a $C_2$-$C_{50}$ alkenyl group, a $C_2$-$C_{50}$ alkynyl group, a $C_1$-$C_{50}$ alkoxy group, a $C_3$-$C_{50}$ cycloalkyl group, a $C_3$-$C_{50}$ cycloalkenyl group, a $C_5$-$C_{60}$ aryl group, a $C_5$-$C_{60}$ aryloxy group, a $C_5$-$C_{60}$ arylthio group, a $C_2$-$C_{60}$ heteroaryl group, a $C_2$-$C_{60}$ polycyclic condensed group, $N(Q_{101})(Q_{102})$, or $Si(Q_{103})(Q_{104})(Q_{105})$. In this regard, $Q_{101}$ to $Q_{105}$ may be each independently a hydrogen atom, a deuterium, a tritium, a halogen atom, a hydroxyl group, a cyano group, an amino group, a nitro group, a carboxyl group, a silyl group, a $C_1$-$C_{50}$ alkyl group, a $C_2$-$C_{50}$ alkenyl group, a $C_2$-$C_{50}$ alkynyl group, a $C_1$-$C_{50}$ alkoxy group, a $C_3$-$C_{50}$ cycloalkyl group, a $C_3$-$C_{50}$ cycloalkenyl group, a $C_5$-$C_{60}$ aryl group, a $C_5$-$C_{60}$ aryloxy group, a $C_5$-$C_{60}$ arylthio group, a $C_5$-$C_{60}$ heteroaryl group, or a $C_2$-$C_{60}$ polycyclic condensed group.

For example, the term "substituted A" refers to A in which at least one hydrogen atom is substituted with a deuterium, a tritium, a halogen atom, a hydroxyl group, a cyano group, a nitro group, a carboxyl group, a silyl group, a methyl group, an ethyl group, a propyl group, a butyl group, a pentyl group, a phenyl group, a biphenyl group, a pentarenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthryl group, a fluoranthenyl group, a triphenylenyl group, a pyrenyl group, a chrysenyl group, a naphtnacenyl group, a picenyl group, a perylenyl group, a pentaphenyl group, a hexacenyl group, a pyrrolyl group, a imidazolyl group, a benzoimidazolyl group, a phenylbenzoimidazolyl group, a pyrazolyl group, a pyridinyl group, a phenylpyridinyl group, a phenylimidazopyridinyl group, a pyrazinyl group, a pyrimidinyl group, a phenylimidazopyrimidinyl group, a pyridazinyl group, an indolyl group, an isoindolyl group, an indazolyl group, a purinyl group, a quinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, a acridinyl group, a phenanthrolinyl group, a phenazinyl group, a furanyl group, a benzofuranyl group, a dibenzofuranyl group, a thiophenyl group, a benzo[b]thiophenyl group, a dibenzothiophenyl, a thiazolyl group, a isothiazolyl group, a benzothiazolyl group, a oxazolyl group, a isoxazolyl group, a benzooxazolyl group, a triazolyl group, a phenyltriazolyl group, a tetrazolyl group, a oxadiazolyl group, a phenyloxadiazolyl group, a triazinyl group, a phenyltriazinyl group, a diphenylethynyl group, a phenylethynylfluorenyl group, a phenylethynylnaphthyl group, $N(Q_{101})(Q_{102})$, or $Si(Q_{103})(Q_{104})(Q_{105})$.

The unsubstituted $C_1$-$C_{50}$ alkyl group used herein refers to a linear or branched saturated hydrocarbon group lacking one hydrogen atom therefrom. Examples of the unsubstituted. $C_1$-$C_{50}$ alkyl group include methyl, ethyl, propyl, isobutyl, sec-butyl, pentyl, iso-amyl, and hexyl. The substituents of the substituted $C_1$-$C_{30}$ alkyl group are defined as described above with reference to the "substituted A".

The unsubstituted $C_2$-$C_{50}$ alkenyl group used herein refers to a hydrocarbon chain having at least one carbon-carbon double bond within or at a terminal of the unsubstituted $C_2$-$C_{50}$ alkyl group. Examples of the unsubstituted $C_2$-$C_{50}$ alkenyl group include ethenyl, propenyl, butenyl, pentenyl, hexenyl, heptenyl, octenyl, propadienyl, isoprenyl, and allyl. The substituents of the substituted $C_2$-$C_{50}$ alkenyl group are defined as described above with reference to the "substituted A".

The unsubstituted $C_2$-$C_{50}$ alkynyl group used herein refers to a hydrocarbon chain having at least one carbon-carbon triple bond within or at a terminal of the unsubstituted $C_2$-$C_{50}$ alkyl group. Examples of the unsubstituted $C_2$-$C_{50}$ alkynyl group include acetylenyl. The substituents of the substituted $C_2$-$C_{50}$ alkynyl group are defined as described above with reference to the "substituted A".

The unsubstituted $C_1$-$C_{50}$ alkoxy group used herein may be represented by —OY, wherein Y is a unsubstituted $C_1$-$C_{50}$ alkyl group as described above, and may be methoxy, ethoxy, isopropyloxy, butoxy, or pentoxy. The substituents of the substituted $C_1$-$C_{50}$ alkoxy group are defined as described above with reference to the "substituted A".

The unsubstituted $C_3$-$C_{50}$ cycloalkyl group used herein refers to a cyclic saturated hydrocarbon chain, and may be cyclopropyl, cyclobutyl, cyclopentyl, cyclohexyl, or cyclooctyl. The substituents of the substituted $C_3$-$C_{50}$ cycloalkyl group are defined as described above with reference to the "substituted A".

The unsubstituted $C_3$-$C_{50}$ cycloalkenyl group refers to a cyclic unsaturated hydrocarbon chain that has at least one carbon-carbon double bond and is not an aromatic ring. Examples of the unsubstituted $C_3$-$C_{60}$ cycloalkenyl group include cyclopropenyl, cyclobutenyl, cyclopentenyl, cyclohexenyl, cycloheptenyl, 1,3-cyclohexadienyl, 1,4-cyclohexadienyl, 2,4-cycloheptadienyl, and 1,5-cyclooctadienyl. The substituents of the substituted $C_3$-$C_{50}$ cycloalkenyl group are defined as described above with reference to the "substituted A".

The unsubstituted $C_5$-$C_{60}$ aryl group used herein refers to a monocyclic or polycyclic monovalent group including a $C_5$-$C_{60}$ carbocyclic aromatic system. If the unsubstituted $C_5$-$C_{60}$ aryl group is a polycyclic group, at least two rings thereof may be fused to each other. Examples of the unsubstituted $C_5$-$C_{60}$ aryl group include a phenyl group, a pentalenyl group, an indenyl group, a naphthyl group, an azulenyl group, a heptalenyl group, an indacenyl group, an acenaphtyl group, a fluorenyl group, a spiro-fluorenyl group, a phenalenyl group, a phenanthrenyl group, an anthryl group, a fluoranthenyl group, a triphenylenyl group, a pyrenyl group, a chrysenyl group, a naphthacenyl group, a picenyl group, a perylenyl group, a pentaphenyl group, and a hexacenyl group. The substituents of the substituted $C_5$-$C_{30}$ aryl group are defined as described above with reference to the "substituted A".

The unsubstituted $C_5$-$C_{60}$ aryloxy group refers to a monovalent group in which carbon atoms of the $C_5$-$C_{60}$ aryl group are connected to each other by an oxygen linking group (—O—). The substituents of the substituted $C_5$-$C_{60}$ aryloxy group are defined as described above with reference to the "substituted A".

The unsubstituted $C_5$-$C_{60}$ arylthio group refers to a monovalent group in which carbon atoms of the $C_5$-$C_{60}$ aryl group are connected to each other by a sulfur linking group (—S—). Examples of the unsubstituted $C_5$-$C_{60}$ arylthio group include a phenylthio group, a naphthylthio group, an indanylthio group, and an indenylthio group. The substituents of the substituted $C_5$-$C_{60}$ arylthio group are defined as described above with reference to the "substituted A".

The unsubstituted $C_2$-$C_{60}$ heteroaryl group used herein refers to a monocyclic or polycyclic monavalent group including at least one ring having at least one hetero atom selected from the group consisting of N, O, P, and S. If the unsubstituted $C_2$-$C_{60}$ heteroaryl group is a polycyclic group, at least two rings thereof may be fused to each other. Examples of the unsubstituted $C_2$-$C_{60}$ heteroaryl group include a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzooxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, and a benzooxazolyl group. The substituents of the substituted $C_2$-$C_{60}$ heteroaryl group are defined as described above with reference to the "substituted A".

The unsubstituted $C_2$-$C_{60}$ polycyclic condensed group refers to a polycyclic monavalent group including at least two fused rings. The substituents of the substituted $C_2$-$C_{60}$ polycyclic condensed group are defined as described above with reference to the "substituted A".

The unsubstituted $C_1$-$C_{50}$ alkylene group used herein refers to a linear or branched divalent hydrocarbon group lacking two hydrogen atoms therefrom. Examples of the unsubstituted alkylene group may be understood with reference to the unsubstituted $C_1$-$C_{50}$ alkyl group. The substituents of the substituted $C_1$-$C_{50}$ alkylene group are defined as described above with reference to the "substituted A".

The unsubstituted $C_5$-$C_{60}$ arylene group used herein refers to a monocyclic or polycyclic divalent group including a $C_6$-$C_{60}$ carbocyclic aromatic system. Examples of the unsubstituted $C_5$-$C_{60}$ arylene group may be understood with reference to the unsubstituted $C_5$-$C_{60}$ aryl group. The substituents of the substituted $C_5$-$C_{60}$ arylene group are defined as described above with reference to the "substituted A".

The unsubstituted $C_5$-$C_{60}$ aryleneoxy group refers to a divalent group in which carbon atoms of the $C_5$-$C_{60}$ arylene group are connected to each other by an oxygen linking group (—O—). The substituents of the substituted $C_5$-$C_{60}$ aryleneoxy group are defined as described above with reference to the "substituted A".

The unsubstituted $C_5$-$C_{60}$ arylenethio group refers to a divalent group in which carbon atoms of the $C_5$-$C_{60}$ arylene group are connected to each other by a sulfur linking group (—S—). The substituents of the substituted $C_5$-$C_{60}$ arylenethio group are defined as described above with reference to the "substituted A".

The unsubstituted $C_2$-$C_{60}$ heteroarylene group used herein refers to a monocyclic or polycyclic divalent group including at least one ring having at least one hetero atom selected from the group consisting of N, O, P, and S. Examples of the unsubstituted $C_2$-$C_{60}$ heteroarylene group may be understood with reference to the unsubstituted $C_2$-$C_{60}$ heteroaryl group. The substituents of the substituted $C_2$-$C_{60}$ heteroarylene group are defined as described above with reference to the "substituted A".

The unsubstituted divalent $C_2$-$C_{60}$ polycyclic condensed group refers to a polycyclic divalent group having 2 to 60 carbon atoms and including at least two fused rings. The substituents of the substituted $C_2$-$C_{60}$ polycyclic condensed group are defined as described above with reference to the "substituted A".

The heterocyclic compound represented by Formula 1 may be synthesized using known organic synthesis methods. The method of synthesizing the heterocyclic compound will be obvious to one or ordinary skill in the art with reference examples that will be described later.

The heterocyclic compound represented by Formula 1 may be used in an organic layer interposed between a pair of electrodes of an organic light-emitting diode.

The heterocyclic compound of Formula 1 has excellent light-emitting characteristics and excellent electron transporting characteristics, and thus may be used as electron injecting materials or electron transporting materials suitable for all-color fluorescent and phosphorescent devices, such as red, green, blue, and white fluorescent and phosphorescent devices. In particular, the heterocyclic compound is efficiently used as light-emitting materials of green, blue, and white fluorescent devices. By using the heterocyclic compound represented by Formula 1, organic light-emitting devices having high efficiency, low driving voltage, high brightness, and long lifespan may be prepared.

An organic light-emitting diode according to an embodiment of the present invention includes: a first electrode; a second electrode disposed opposite to the first electrode; and an organic layer interposed between the first electrode and the second electrode, wherein the organic layer includes a heterocyclic compound represented by Formula 1 as a single material or a combination of different materials.

The term "organic layer" used herein refers to a single layer or a multi layers interposed between the first electrode and the second electrode.

The organic layer may include at least one layer selected from the group consisting of a (HIL), a hole transport layer (HTL), a functional layer having both hole injecting and hole transporting capabilities, an electron blocking layer (EBL), an emission layer (EML), a hole blocking layer (HBL), an electron transport layer (ETL), an electron injection layer (EIL) and a functional layer having both electron transporting and electron injecting capabilities. At lease one of the HIL, the HTL, the functional layer having both hole injecting and hole transporting capabilities, the EBL, the EML, the HBL, the ETL, the EIL, and the functional layer having both electron transporting and electron injecting capabilities may include the heterocyclic compound represented by Formula 1.

The heterocyclic compound represented by Formula 1 may be used in the organic layer as a single material or a combination of different materials. For example, Compound 3 may only be contained in the organic layer as a single material, or a combination of Compounds 3 and 52 may be contained in the organic layer. If the organic layer includes both of Compounds 3 and 52, Compounds 3 and 52 may be contained in the same layer, e.g., the EML. Alternatively, Compounds 3 and 52 may be contained in different layers, e.g., Compound 3 may be contained in the EML and Compound 52 may be contained in an ETL.

The organic layer may include the HIL, the HTL, the EML, the ETL, and the EIL, and the heterocyclic compound represented by Formula 1 may be contained in the EML.

The organic layer may include the EML, wherein the EML includes the heterocyclic compound represented by Formula 1.

The organic layer may include the EML, wherein the EML includes a fluorescent or phosphorescent host and the fluorescent or phosphorescent host includes the heterocyclic compound represented by Formula 1. The phosphorescent dopant may be an organic metal complex including Ir, Pt, Os, Re, Ti, Zr, Hf, or any combination of at least two thereof, but is not limited thereto.

The organic layer may include the EML, wherein the EML includes a fluorescent dopant, and the fluorescent dopant includes the heterocyclic compound represented by Formula 1.

The organic layer may include at least one of the ETL, the EIL and the functional layer having both electron transporting and electron injecting capabilities, and at least one of the ETL, the EIL and the functional layer having both electron transporting and electron injecting capabilities may include the heterocyclic compound represented by Formula 1.

The organic layer may include at least one of the ETL, the EIL and the functional layer having both electron transporting and electron injecting capabilities, and at least one of the ETL, the EIL and the functional layer having both electron transporting and electron injecting capabilities may include the heterocyclic compound represented by Formula 1 and a metal-containing material.

The organic layer may include at least one of the ETL, the EIL, the functional layer having both electron transporting and electron injecting capabilities, and an EML having at least one of a red EML, a green EML, a blue EML, and a white EML; wherein at least one of the ETL, the EIL and the functional layer having both electron transporting and electron injecting capabilities includes the heterocyclic compound represented by Formula 1, and the EML includes a phosphorescent compound.

The organic light-emitting diode may have the following structures between the EML and the second electrode, but is not limited thereto.

1) EML(heterocyclic compound represented by Formula 1)/ETL/EIL/second electrode;

2) EML(heterocyclic compound represented by Formula 1 as a fluorescent or phosphorescent host)/ETL/EIL/second electrode;

3) EML(heterocyclic compound represented by Formula 1 as a fluorescent dopant)/ETL/EIL/second electrode;

4) EML(heterocyclic compound represented by Formula 1+anthracene-based compound)/ETL/EIL/second electrode;

5) EML(heterocyclic compound represented by Formula 1+styryl-based compound)/ETL/EIL/second electrode;

6) EML(heterocyclic compound represented by Formula 1+arylamino-based compound)/ETL/EIL/second electrode;

In the organic light-emitting diodes having the structures 1) to 6), the EML may include the heterocyclic compound represented by Formula 1 as a single material or may further include another emitting material.

In the organic light-emitting diodes having the structures 4) to 6), the EML may further include at least one of an anthracene-based compound, a styryl-based compound, and an arylamino-based compound in addition to the heterocyclic compound represented by Formula 1 (as a single material or as a mixture further including another light-emitting material). For example, the EML may further include any combination of Compound 3, the anthracene-based compound (e.g., 9,10-di(naphthalene-2-yl)anthracene (and)) and the styryl-based compound (e.g., distyrylarylene (DSA)).

In the organic light-emitting diodes having the structures 1) to 6), the EML may include at least one of a red EML, a green EML, a blue EML, and a white EML.

The organic light-emitting diode may have the following structures between the EML and the second electrode, but is not limited thereto.

7) EML/ETL(heterocyclic compound represented by Formula 1)/EIL/second electrode;

8) EML/ETL/EIL(heterocyclic compound represented by Formula 1)/second electrode;

9) EML/ETL(heterocyclic compound represented by Formula 1)/EIL(heterocyclic compound represented by Formula 1)/second electrode;

10) EML/functional layer having both electron transporting and electron injecting capabilities(heterocyclic compound represented by Formula 1)/second electrode;

11) EML/ETL(heterocyclic compound represented by Formula 1+metal-containing material)/EIL/second electrode;

12) EML/ETL(heterocyclic compound represented by Formula 1)/EIL(metal-containing material)/second electrode;

13) EML/ETL(metal-containing material)/EIL(heterocyclic compound represented by Formula 1)/second electrode;

14) EML/ETL/EIL(heterocyclic compound represented by Formula metal-containing material)/second electrode;

15) EML/functional layer having both electron transporting and electron injecting capabilities(heterocyclic compound represented by Formula 1+metal-containing material)/second electrode;

In the organic light-emitting diodes having the structures 7) to 15), at least one of the ETL, the EIL and the functional layer having both electron transporting and electron injecting capabilities may include the heterocyclic compound represented by Formula 1 as a single material or may further include another emitting material.

In the organic light-emitting diodes having the structures 11) to 15), at least one of the ETL, the EIL and the functional layer having both electron transporting and electron injecting capabilities may include the heterocyclic compound represented by Formula 1 as a single material or may further include another emitting material. The metal-containing material may include a Li complex. Examples of the Li complex include lithium quinolate (LiQ) or Compound 101 below, but are not limited thereto.

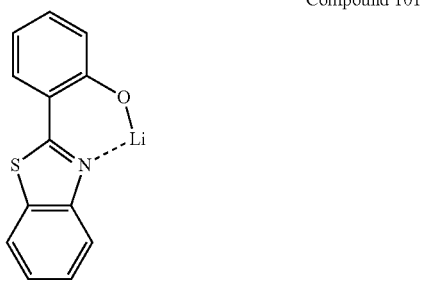

Compound 101

In the organic light-emitting diode having the structures 7) to 15), the EML may include at least one of a red EML, a green EML, a blue EML, and a white EML.

The organic light-emitting diode may have the following structures between the EML and the second electrode, but is not limited thereto.

16) EML(heterocyclic compound represented by Formula 1)/ETL(heterocyclic compound represented by Formula 1)/EIL/second electrode;

17) EML(heterocyclic compound represented by Formula 1)/ETL/EIL(heterocyclic compound represented by Formula 1)/second electrode;

18) EML(heterocyclic compound represented by Formula 1)/ETL(heterocyclic compound represented by Formula 1)/EIL(heterocyclic compound represented by Formula 1)/second electrode;

19) EML(heterocyclic compound represented by Formula 1)/functional layer having both electron transporting and electron injecting capabilities(heterocyclic compound represented by Formula 1)/second electrode;

20) EML(heterocyclic compound represented by Formula 1)/ETL(heterocyclic compound represented by Formula 1+metal-containing material)/EIL/second electrode;

21) EML(heterocyclic compound represented by Formula 1)/ETL(heterocyclic compound represented by Formula 1)/EIL(metal-containing material)/second electrode;

22) EML(heterocyclic compound represented by Formula 1)/ETL(metal-containing material)/EIL(heterocyclic compound represented by Formula 1)/second electrode;

23) EML(heterocyclic compound represented by Formula 1)/ETL/EIL(heterocyclic compound represented by Formula 1+metal-containing material)/second electrode;

24) EML(heterocyclic compound represented by Formula 1)/functional layer having both electron transporting and electron injecting capabilities(heterocyclic compound represented by Formula 1+metal-containing material)/second electrode;

25) EML(heterocyclic compound represented by Formula 1 as a fluorescent or phosphorescent host)/ETL(heterocyclic compound represented by Formula 1)/EIL/second electrode;

26) EML(heterocyclic compound represented by Formula 1 as a fluorescent or phosphorescent host)/ETL/EIL(heterocyclic compound represented by Formula 1)/second electrode;

27) EML(heterocyclic compound represented by Formula 1 as a fluorescent or phosphorescent host)/ETL(heterocyclic compound represented by Formula 1)/EIL(heterocyclic compound represented by Formula 1)/second electrode;

28) EML(heterocyclic compound represented by Formula 1 as a fluorescent or phosphorescent host)/functional layer having both electron transporting and electron injecting capabilities(heterocyclic compound represented by Formula 1)/second electrode;

29) EML(heterocyclic compound represented by Formula 1 as a fluorescent or phosphorescent host)/ETL(heterocyclic compound represented by Formula 1+metal-containing material)/EIL/second electrode;

30) EML(heterocyclic compound represented by Formula 1 as a fluorescent or phosphorescent host)/ETL(heterocyclic compound represented by Formula 1)/EIL(metal-containing material)/second electrode;

31) EML(heterocyclic compound represented by Formula 1 as a fluorescent or phosphorescent host)/ETL(metal-containing material)/EIL(heterocyclic compound represented by Formula 1)/second electrode;

32) EML(heterocyclic compound represented by Formula 1 as a fluorescent or phosphorescent host)/ETL/EIL(heterocyclic compound represented by Formula 1+metal-containing material)/second electrode;

33) EML(heterocyclic compound represented by Formula 1 as a fluorescent or phosphorescent host)/functional layer having both electron transporting and electron injecting capabilities(heterocyclic compound represented by Formula 1+metal-containing material)/second electrode;

34) EML(heterocyclic compound represented by Formula 1 as a fluorescent dopant)/ETL(heterocyclic compound represented by Formula 1)/EIL/second electrode;

35) EML(heterocyclic compound represented by Formula 1 as a fluorescent dopant)/ETL/EIL(heterocyclic compound represented by Formula 1)/second electrode;

36) EML(heterocyclic compound represented by Formula 1 as a fluorescent dopant)/ETL(heterocyclic compound represented by Formula 1)/EIL(heterocyclic compound represented by Formula 1)/second electrode;

37) EML(heterocyclic compound represented by Formula 1 as a fluorescent dopant)/functional layer having both electron transporting and electron injecting capabilities(heterocyclic compound represented by Formula 1)/second electrode;

38) EML(heterocyclic compound represented by Formula 1 as a fluorescent dopant)/ETL(heterocyclic compound represented by Formula 1+metal-containing material)/EIL/second electrode;

39) EML(heterocyclic compound represented by Formula 1 as a fluorescent dopant)/ETL(heterocyclic compound represented by Formula 1)/EIL(metal-containing material)/second electrode;

40) EML(heterocyclic compound represented by Formula 1 as a fluorescent dopant)/ETL(metal-containing material)/EIL(heterocyclic compound represented by Formula 1)/second electrode;

41) EML(heterocyclic compound represented by Formula 1 as a fluorescent dopant)/ETL/EIL(heterocyclic compound represented by Formula 1+metal-containing material)/second electrode;

42) EML(heterocyclic compound represented by Formula 1 as a fluorescent dopant)/functional layer having both electron transporting and electron injecting capabilities(heterocyclic compound represented by Formula 1+metal-containing material)/second electrode;

43) EML(heterocyclic compound represented by Formula 1+anthracene-based compound)/ETL(heterocyclic compound represented by Formula 1)/EIL/second electrode;

44) EML(heterocyclic compound represented by Formula 1+anthracene-based compound)/ETL/EIL(heterocyclic compound represented by Formula 1)/second electrode;

45) EML(heterocyclic compound represented by Formula 1+anthracene-based compound)/ETL(heterocyclic compound represented by Formula 1)/EIL(heterocyclic compound represented by Formula 1)/second electrode;

46) EML(heterocyclic compound represented by Formula 1+anthracene-based compound)/functional layer having both electron transporting and electron injecting capabilities(heterocyclic compound represented by Formula 1)/second electrode;

47) EML(heterocyclic compound represented by Formula 1+anthracene-based compound)/ETL(heterocyclic compound represented by Formula 1+metal-containing material)/EIL/second electrode;

48) EML(heterocyclic compound represented by Formula 1+anthracene-based compound)/ETL(heterocyclic compound represented by Formula 1)/EIL(metal-containing material)/second electrode;

49) EML(heterocyclic compound represented by Formula 1+anthracene-based compound)/ETL(metal-containing material)/EIL(heterocyclic compound represented by Formula 1)/second electrode;

50) EML(heterocyclic compound represented by Formula 1+anthracene-based compound)/ETL/EIL(heterocyclic compound represented by Formula 1+metal-containing material)/second electrode;

51) EML(heterocyclic compound represented by Formula 1+anthracene-based compound)/functional layer having both electron transporting and electron injecting capabilities(heterocyclic compound represented by Formula 1+metal-containing material)/second electrode;

52) EML(heterocyclic compound represented by Formula 1+styryl-based compound)/ETL(heterocyclic compound represented by Formula 1)/EIL/second electrode;

53) EML(heterocyclic compound represented by Formula 1+styryl-based compound)/ETL/EIL(heterocyclic compound represented by Formula 1)/second electrode;

54) EML(heterocyclic compound represented by Formula 1+styryl-based compound)/ETL(heterocyclic compound represented by Formula 1)/EIL(heterocyclic compound represented by Formula 1)/second electrode;

55) EML(heterocyclic compound represented by Formula 1+styryl-based compound)/functional layer having both electron transporting and electron injecting capabilities(heterocyclic compound represented by Formula 1)/second electrode;

56) EML(heterocyclic compound represented by Formula 1+styryl-based compound)/ETL(heterocyclic compound represented by Formula 1+metal-containing material)/EIL/second electrode;

57) EML(heterocyclic compound represented by Formula 1+styryl-based compound)/ETL(heterocyclic compound represented by Formula 1)/EIL(metal-containing material)/second electrode;

58) EML(heterocyclic compound represented by Formula 1+styryl-based compound)/ETL(metal-containing material)/EIL(heterocyclic compound represented by Formula 1)/second electrode;

59) EML(heterocyclic compound represented by Formula 1+styryl-based compound)/ETL/EIL(heterocyclic compound represented by Formula 1+metal-containing material)/second electrode;

60) EML(heterocyclic compound represented by Formula 1+styryl-based compound)/functional layer having both electron transporting and electron injecting capabilities(heterocyclic compound represented by Formula 1+metal-containing material)/second electrode;

61) EML(heterocyclic compound represented by Formula 1+arylamino-based compound)/ETL(heterocyclic compound represented by Formula 1)/EIL/second electrode;

62) EML(heterocyclic compound represented by Formula 1+arylamino-based compound)/ETL/EIL(heterocyclic compound represented by Formula 1)/second electrode;

63) EML(heterocyclic compound represented by Formula 1+arylamino-based compound)/ETL(heterocyclic compound represented by Formula 1)/EIL(heterocyclic compound represented by Formula 1)/second electrode;

64) EML(heterocyclic compound represented by Formula 1+arylamino-based compound)/functional layer having both electron transporting and electron injecting capabilities(heterocyclic compound represented by Formula 1)/second electrode;

65) EML(heterocyclic compound represented by Formula 1+arylamino-based compound)/ETL(heterocyclic compound represented by Formula 1+metal-containing material)/EIL/second electrode;

66) EML(heterocyclic compound represented by Formula 1+arylamino-based compound)/ETL(heterocyclic compound represented by Formula 1)/EIL(metal-containing material)/second electrode;

67) EML(heterocyclic compound represented by Formula 1+arylamino-based compound)/ETL(metal-containing material)/EIL(heterocyclic compound represented by Formula 1)/second electrode;

68) EML(heterocyclic compound represented by Formula 1+arylamino-based compound)/ETL/EIL(heterocyclic compound represented by Formula 1+metal-containing material)/second electrode;

69) EML(heterocyclic compound represented by Formula 1+arylamino-based compound)/functional layer having both electron transporting and electron injecting capabilities(heterocyclic compound represented by Formula 1+metal-containing material)/second electrode;

In the organic light-emitting diodes having the structures of 16) to 69), the EML may include the heterocyclic compound represented by Formula 1 as a single material or may further include another emitting material. At least one of the ETL, the EIL, and the functional layer having both electron transporting and electron injecting capabilities may include the heterocyclic compound represented by Formula 1 as a single material or may further include another emitting material.

In the organic layer, at least one layer of the HIL, the HTL, the functional layer having both hole injecting and hole transporting capabilities, the EBL, the EML, the HIBL, the ETL, the EIL, and the functional layer having both electron transporting and electron injecting capabilities may be formed using deposition or a wet process.

The "wet process" is a process by which a solution containing a material and a solvent is provided to a substrate, and at least one portion of the solvent is removed by drying and/or heat-treatment to form a layer including the material on the substrate.

For example, the organic layer may be formed by using a known deposition method. Alternatively, a mixture including the heterocyclic compound and a solvent is provided to a region where the first layer will be formed (e.g., on the HTL) by spin coating, spraying, inkjet printing, dipping, casting, gravure coating, bar coating, roll coating, wire-bar coating, screen coating, flexo coating, offset coating, laser induced thermal imaging, or the like, and the mixture is dried and/or heat-treated to remove at least one portion of the solvent to form the organic layer.

Meanwhile, the laser induced thermal imaging including forming the organic layer using a wet process as described above on a base film and transferring the organic layer to a region where the organic layer will be formed (e.g., on the HTL) using a laser beam may also be used.

The organic layer may include optionally at least one of the HIL, the HTL, and the functional layer having both hole injecting and hole transporting capabilities, and at least one of the HIL, the HTL, and the functional layer having both hole injecting and hole transporting capabilities may further include a charge-generating material. The charge-generating material improves conductivity of the layers. The charge-generating material may be a p-dopant. Examples of the p-dopant include a quinine derivative such as tetracyano-quinonedimethane (TCNQ) and 2,3,5,6-tetrafluoro-tetracyano-1,4-benzoquinonedimethane (F4TCNQ); a metal oxide such as tungsten oxide and molybdenum oxide; and a cyano group-containing compound such as Compound 201 below, but are not limited thereto.

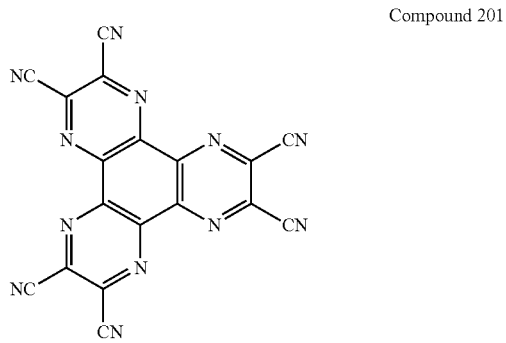 [SMILES: N#Cc1nc2c3nc(C#N)c(C#N)nc3c3nc(C#N)c(C#N)nc3c2nc1C#N]

Compound 201

If the HIL, the HTL, or the functional layer having both hole injecting and hole transporting capabilities further includes the charge-generating material, the charge-generating material may be homogeneously or non-homogeneously dispersed between the layers, or a variety of modifications may be possible.

FIG. 1 is a schematic cross-sectional view of an organic light-emitting diode 10 according to an embodiment of the present invention. Hereinafter, the organic light-emitting diode 10 and a method of fabricating the organic light-emitting diode 10 will be described with reference to FIG. 1.

The organic light-emitting diode 10 according to the current embodiment includes a substrate 11, a first electrode 12, a HIL 13, a HTL 14, an EML 15, an ETL 16, an EIL 17, and a second electrode 18 which are sequentially stacked.

The substrate 11, which may be any substrate that is commonly used in organic light-emitting diodes, may be a glass substrate or a transparent plastic substrate with excellent mechanical strength, thermal stability, transparency, surface smoothness, ease of handling, and waterproofness.

The first electrode 12 may be formed on the substrate 11 by depositing or sputtering a material that is used to form the first electrode 12. When the first electrode 12 constitutes an anode, the material used to form the first electrode 12 may be a high work-function material so as to facilitate hole injection. The first electrode 12 may be a reflective electrode or a transmissive electrode. Transparent and conductive materials such as indium tin oxide (ITO), indium zinc oxide (IZO), tin oxide ($SnO_2$), and zinc oxide (ZnO) may be used to form the first electrode 12. The first electrode 12 may be formed as a reflective electrode using magnesium (Mg), aluminum (Al), aluminum-lithium (Al—Li), calcium (Ca), magnesium-indium (MgIn), magnesium-silver (Mg—Ag), or the like. The first electrode 12 may include two different materials. For example, the first electrode 12 may have a double layered structure with two different materials.

The HIL 13 is disposed on the first electrode 12.

The HIL 13 may be formed on the first electrode 12 by vacuum deposition, a wet process, laser induced thermal imaging, or the like.

When the HIL 13 is formed using vacuum deposition, the deposition conditions may vary according to a compound that is used to form the HIL 13, and the structure and thermal characteristics of the HIL 13 to be formed. For example, the deposition conditions may include a deposition temperature of 100 to 500° C., a vacuum pressure of $10^{-8}$ to $10^{-3}$ torr, and a deposition rate of 0.01 to 100 Å/sec, but are not limited thereto.

When the HIL 13 is formed using spin coating, coating conditions may vary according to a compound that is used to form the HIL 13, and the structure and thermal properties of the HIL 13 to be formed. For example, the coating conditions may include a coating speed of about 2,000 rpm to about 5,000 rpm, and a thermal treatment temperature of about 80° C. to about 200° C., wherein the thermal treatment is for removing a solvent after coating. However, the coating conditions are not limited thereto.

Alternatively, well known hole injecting materials may also be used. Examples of such hole injecting materials include, but are not limited to, a phthalocyanine compound such as copper phthalocyanine, m-MTDATA (refer to the following formula), TDATA (refer to the following formula), 2-TNATA (refer to the following formula), polyaniline/dodecylbenzenesulfonic acid (Pan i/DBSA), poly(3,4-ethylenedioxythiophene)/poly(4-styrenesulfonate) (PEDOT/PSS), polyaniline/camphor sulfonicacid (Pani/CSA), and (polyaniline)/poly(4-styrenesulfonate) (PANI/PSS).

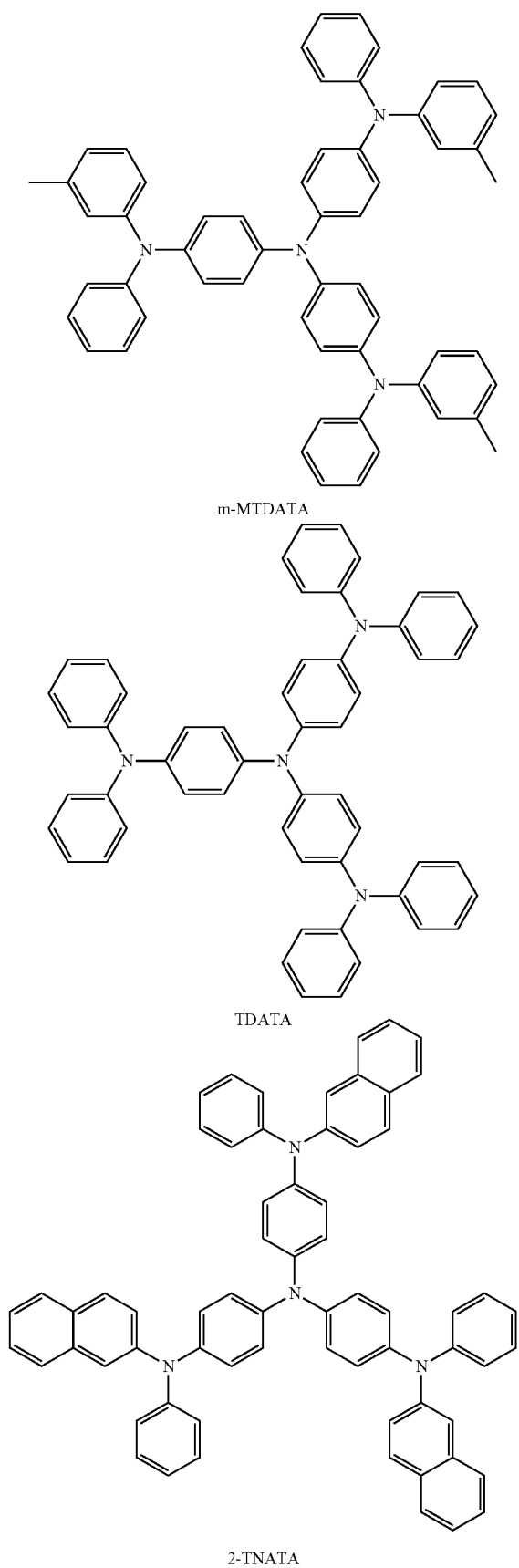

m-MTDATA

TDATA

2-TNATA

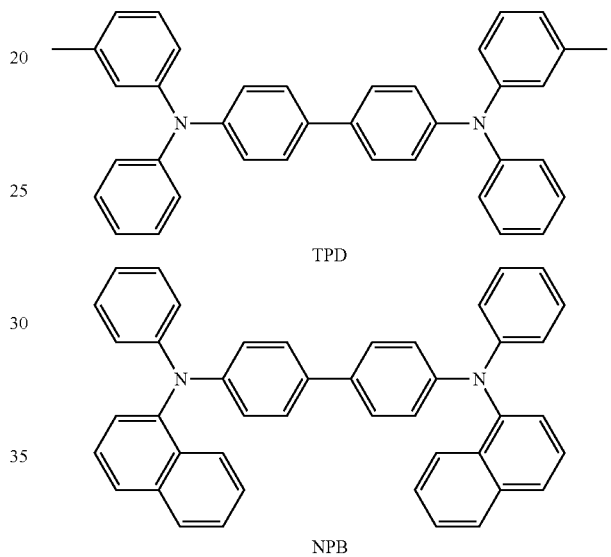

TPD

NPB

The thickness of the HIL 13 may be about 100 to about 10,000 Å, and for example, about 100 to about 1,000 Å. When the thickness of the HIL 13 is within this range, the HIL 13 may have excellent hole injecting ability without a substantial increase in driving voltage Then, a HTL 14 may be formed on the HIL 13 by vacuum deposition, a wet process, laser induced thermal imaging, or the like. When the HTL 14 is formed by vacuum deposition or spin coating, the conditions for deposition and coating may be similar to those for the formation of the HIL 13, although the conditions for the deposition and coating may vary according to the material that is used to form the HTL 14.

Alternatively, the HTL 14 may be formed of known hole transporting materials, for example, TPD (refer to the following formula), and NPB (refer to the following formula).

The thickness of the ETL 14 may be in the range of about 50 to about 1,000 Å, for example, about 100 to about 800 Å. When the thickness of the HTL 14 is within this range, the HTL 14 may have excellent hole transporting ability without a substantial increase in driving voltage.

Then, an EML 15 may be formed on the HTL 14 by vacuum deposition, a wet process, laser induced thermal imaging, or the like. When the EML 15 is formed using vacuum deposition or spin coating, the deposition and coating conditions may be similar to those for formation of the HIL 13, although the deposition and coating conditions may vary according to a compound that is used to form the EML 15.

The EML 15 may include the heterocyclic compound represented by Formula 1 as described above. The EML 15 may further include a known phosphorescent host, fluorescent host, phosphorescent dopant, or fluorescent dopant in addition to the heterocyclic compound represented by Formula 1. The heterocyclic compound represented by Formula 1 may function as the phosphorescent host, the fluorescent host, or the fluorescent dopant.

For example, examples of known hosts include 4,4'-N,N'-dicarbazole-biphenyl (CBP), 9,10-di-(naphthalene-2-yl)anthracene (AND, refer to the following formula), TPBI (refer to the following formula), TBADN (refer to the following formula), and E3 (refer to the following formula), but are not limited thereto.

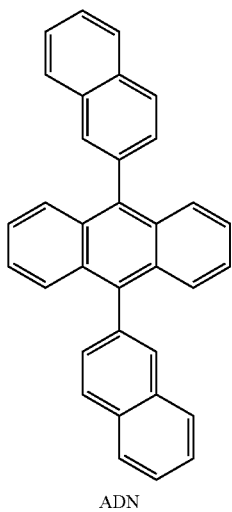

ADN

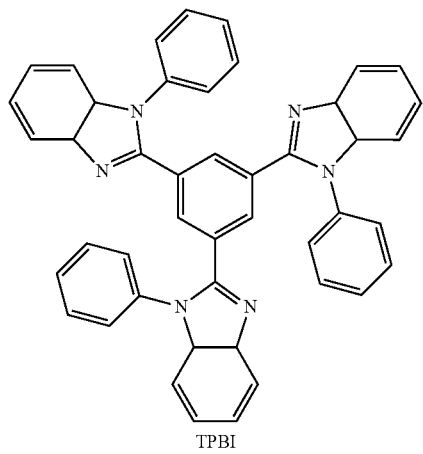

TPBI

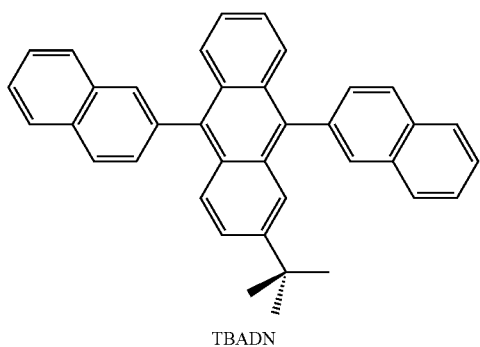

TBADN

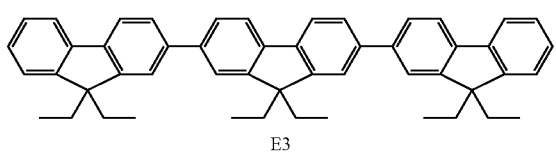

E3

Meanwhile, examples of known red dopants include PtOEP (refer to the following formula), Ir(piq)$_3$ (refer to the following formula), and Btp$_2$Ir(acac) (refer to the following formula), but are not limited thereto.

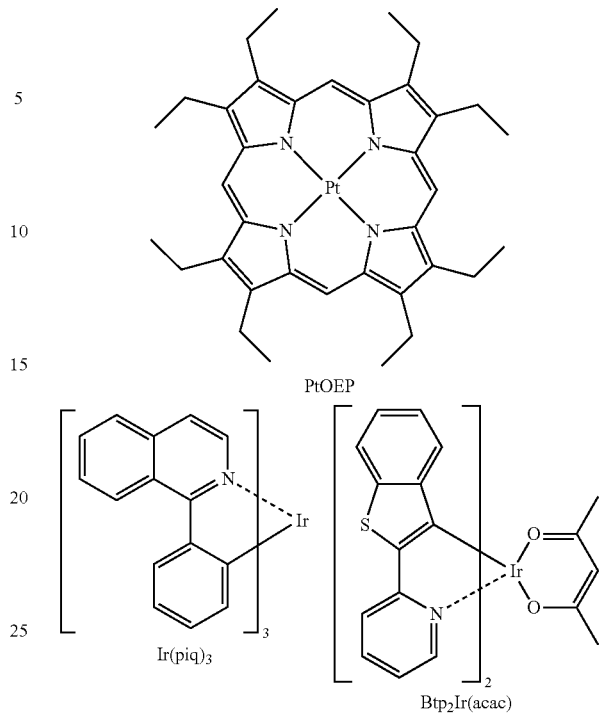

Also, examples of known green dopants include Ir(ppy)$_3$ (ppy=phenylpyridine, refer to the following formula), Ir(ppy)$_2$(acac) (refer to the following formula), and Ir(mpyp)$_3$ (refer to the following formula), but are not limited thereto.

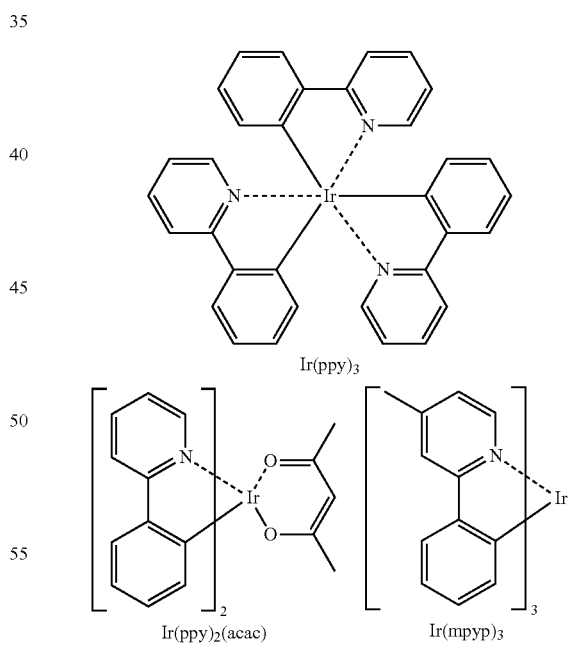

Examples of known blue dopants include F$_2$Irpic (refer to the following formula), (F$_2$ppy)$_2$Ir(tmd) (refer to the following formula), Ir(dfppz)$_3$ (refer to the following formula), DPVBi (refer to the following formula), 4,4'-bis(4-diphenylaminostyryl)biphenyl (DPAVBi, refer to the following formula), and 2,5,8,11-tetra-t-butyl pherylene (TBPe, refer to the following formula), but are not limited thereto.

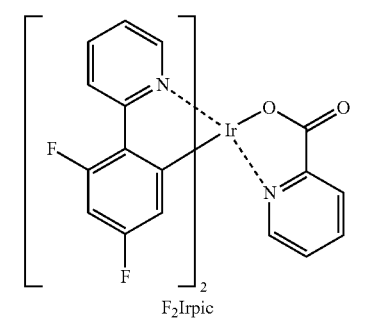

F₂Irpic

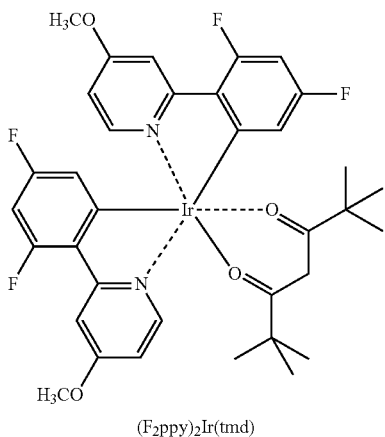

(F₂ppy)₂Ir(tmd)

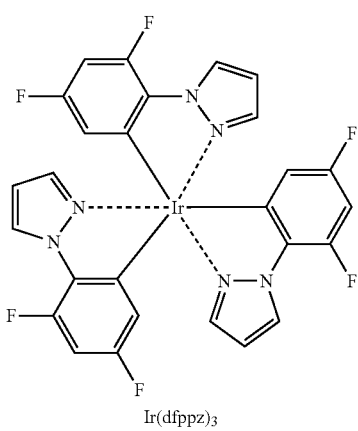

Ir(dfppz)₃

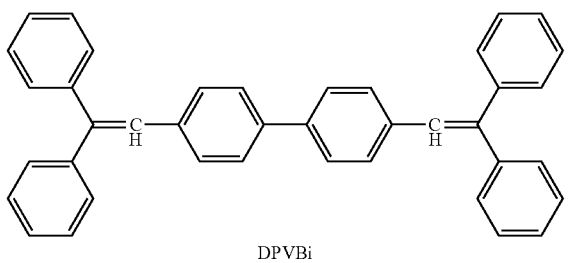

DPVBi

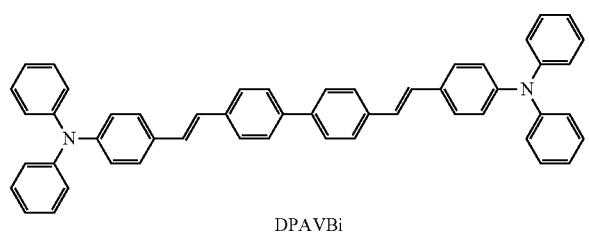

DPAVBi

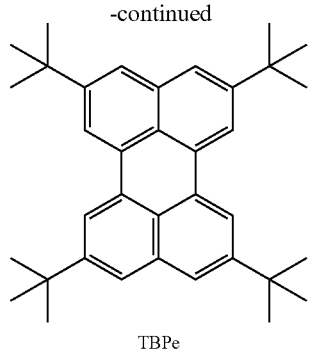

TBPe

If the EML 15 includes the host and the dopant, the amount of the dopant may be in the range of about 0.01 to about 15 parts by weight based on 100 parts by weight of the host, but is not limited thereto.

The thickness of the EML 15 may be in the range of about 100 Å to about 1,000 Å, for example, about 200 Å to about 600 Å. When the thickness of the EML 15 is within this range, the EML 15 may have excellent light emitting ability without a substantial increase in driving voltage.

When a phosphorescent dopant is also used to form the EML 15, a HBL (not shown in FIG. 1) may be formed between the HTL 14 and the EML 15 by using vacuum deposition, a wet process, a laser induced thermal imaging, or the like, in order to prevent diffusion of triplet excitons or holes into an ETL 16. When the HBL is formed using vacuum deposition or spin coating, the conditions for deposition and coating may be similar to those for the formation of the HIL 13, although the conditions for deposition and coating may vary according to the material that is used to form the HBL. Any known hole blocking material that is commonly used in the art may be used. Examples of hole blocking materials include an oxadiazole derivative, a triazole derivative, and a phenanthroline derivative.

The thickness of the HBL may be in a range of about 50 to about 1,000 Å, for example, about 100 to about 300 Å. When the thickness of the HBL is within this range, the HBL may have excellent hole blocking ability without a substantial increase in driving voltage.

Then, an ETL 16 is formed on the EML 15 (or HBL) using various methods, for example, by vacuum deposition, a wet process, laser induced thermal imaging, or the like. The ETL 16 may include the heterocyclic compound represented by Formula 1 as described above. The ETL 16 may be formed of a known electron-transporting material. Examples of the electron-transporting material include, but are not limited to, quinoline derivatives, such as tris(8-quinolinolate)aluminum (Alq₃), TAZ (refer to the following formula), Balq (refer to the following formula), and beryllium bis(benzoquinolin-10-olate) (Balq₂).

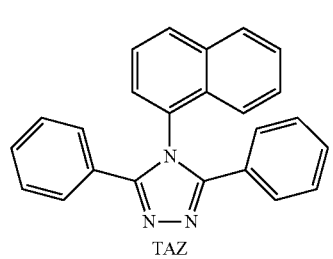

TAZ

-continued

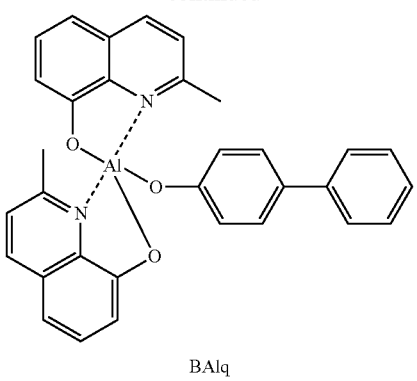

BAlq

The ETL 160 may include an electron-transporting organic compound and a metal-containing material. Examples of the electron-transporting organic compound include anthracene-based compounds such as 9,10-di(naphthalene-2-yl)anthracene (ADN), and Compounds 301 and 302 below, but are not limited thereto.

Compound 301

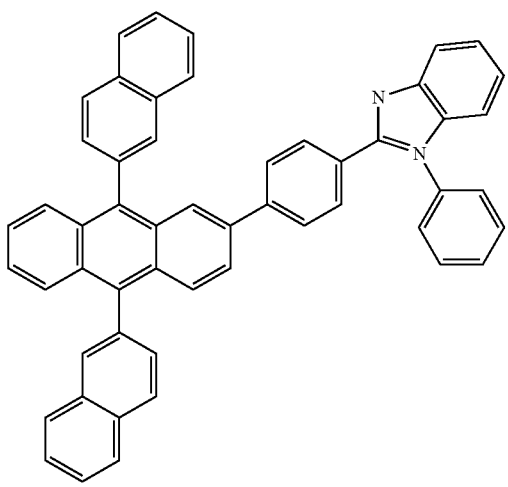

Compound 302

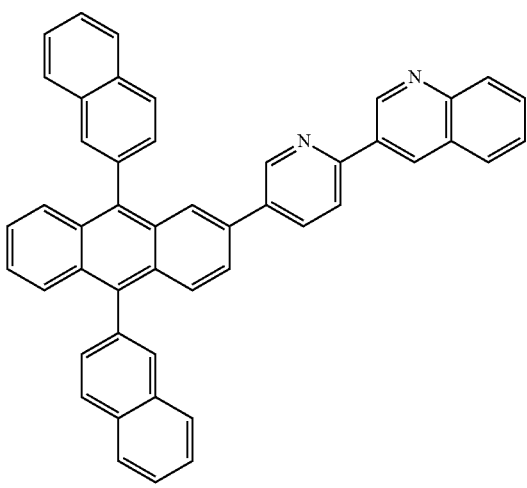

The metal-containing material may include a Li complex. Examples of the Li complex include lithium quinolate (LiQ) or Compound 101 below, but are not limited thereto.

Compound 101

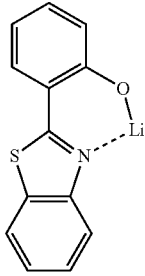

The thickness of the ETL 16 may be in the range of about 100 Å to about 1,000 Å, for example, about 150 Å to about 500 Å. When the thickness of the ETL 16 is within this range, the ETL 16 may have excellent electron transporting ability without a substantial increase in driving voltage. When the ETL 16 is formed using vacuum deposition or spin coating, the deposition and coating conditions may be similar to those for formation of the HIL 13, although the deposition and coating conditions may vary according to a compound that is used to form the ETL 16.

In addition, an EIL 17, which facilitates injection of electrons from the cathode, may be formed on the ETL 16. Examples of materials for forming the EIL 17 include the heterocyclic compound of Formula 1, LiF, NaCl, CsF, $Li_2O$, and BaO, which are known in the art. The conditions for deposition of the EIL 17 are similar to those for formation of the HIL 13, although the deposition conditions may vary according to a material that is used to form the EIL 17.

The thickness of the EIL 17 may be in the range of about 1 to about 100 Å, for example, in the range of about 3 to about 90 Å. When the thickness of the EIL 17 is within the range described above, the EIL 160 may have satisfactory electron injecting properties without an increase in driving voltage.

The second electrode 18 is disposed on the EIL 17. The second electrode 18 may be a cathode, which is an electron injecting electrode. A metal for forming the second electrode 19 may be a metal, an alloy, an electrically conductive compound, which have a low-work function, or a mixture thereof. In this regard, the second electrode 17 may be a transmissive electrode formed of lithium (Li), magnesium (Mg), aluminum (Al), aluminum (Al)-lithium (Li), calcium (Ca), magnesium (Mg)-indium (In), magnesium (Mg)-silver (Ag), or the like. Meanwhile, in order to manufacture a top-emission type organic light-emitting diode, a transmissive electrode formed of ITO or IZO may be used.

The organic light-emitting diode may be used in a flat panel display device including a transistor. There is provided a flat panel display device including a transistor that includes a source, a drain, a gate, and an active layer and an organic light-emitting diode including an organic layer having the heterocyclic compound of Formula 1, wherein one of the source and the drain is electrically connected to the first electrode of the organic light-emitting diode.

The active layer of the transistor may be an amorphous silicon layer, a crystalline silicon layer, an organic semiconductor layer, an oxide semiconductor layer, or the like.

Hereinafter, one or more embodiments will be described in detail with reference to the following examples. These examples are not intended to limit the purpose and scope of the one or more embodiments of the present invention.

An exemplary method of synthesizing a heterocyclic compound of Formula 1 wherein X is *—Ar$_1$ is as follows:

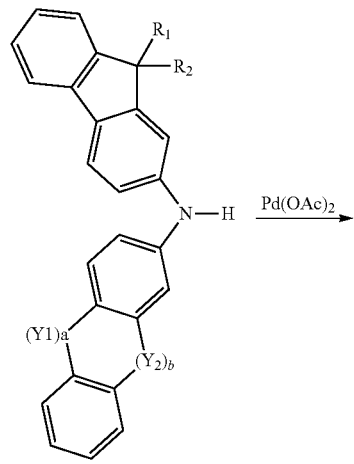

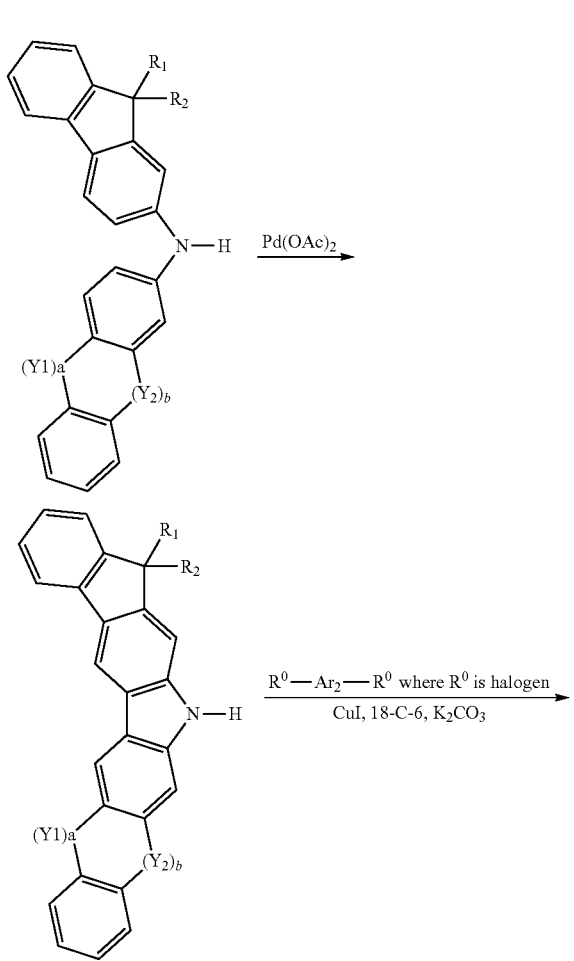

An exemplary method of synthesizing a heterocylic compound of Formula 1 wherein X is

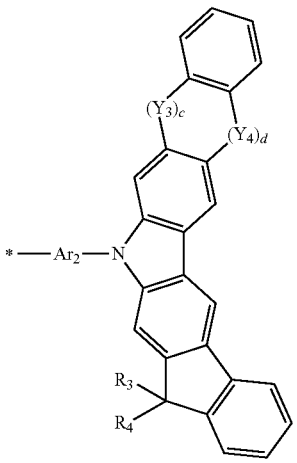

is as follows:

-continued

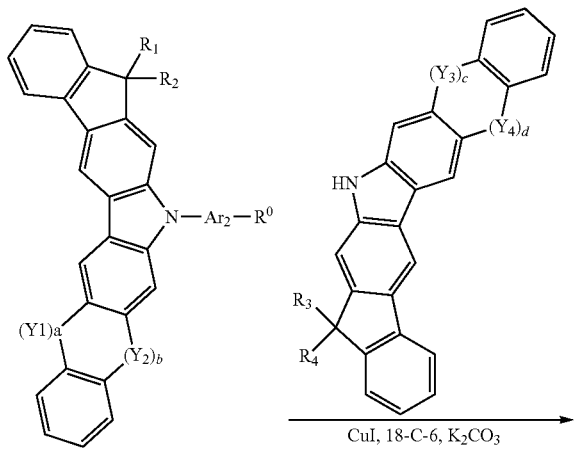

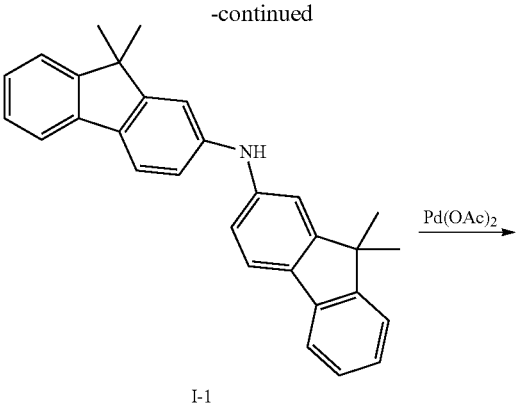

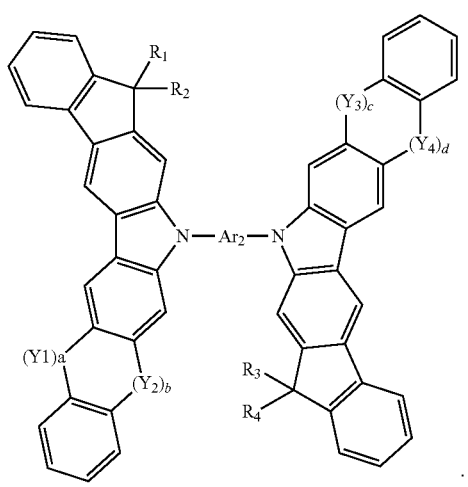

Synthesis Example 1

Synthesis of Compound 3

Compound 3 was synthesized through Reaction Scheme 1 below:

Reaction Scheme 1

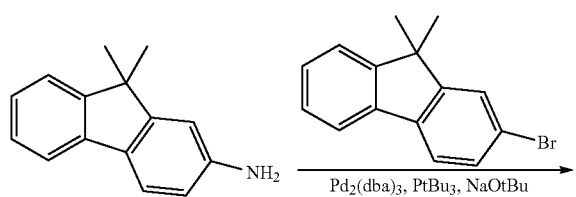

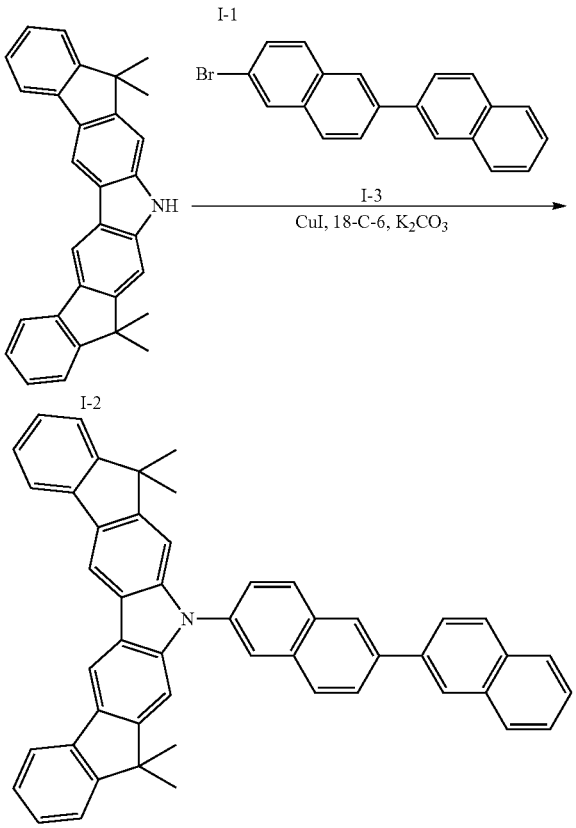

Synthesis of Intermediate I-1

6.27 g (30 mmol) of 2-amino-9,9'-dimethylfluorene, 5.46 g (20.0 mmol) of 2-bromo-9,9'-dimethylfluorene, 366 mg (0.4 mmol) of $Pd_2(bda)_3$ where dba is dibenzylideneacetone, 80 mg (0.4 mmol) of $PtBu_3$, and 2.88 g (30 mmol) of NaOtBu were dissolved in 60 mL of toluene, and the mixture was refluxed at 85° C. for 3 hours. The mixture was cooled to room temperature and subjected to extraction three times with 50 mL of water and 50 mL of diethyl ether. An organic layer was collected and dried using magnesium sulfate to evaporate the solvent. The residue was separately purified using silica gel column chromatography to obtain 6.50 g of Intermediate I-1 (Yield: 81%) The produced compound was identified using $^1$H NMR and MS/FAB. $C_{30}H_{27}N$:calc. 401.21. found 402.23.

$^1$H NMR (400 MHz, $CDCl_3$). δ7.78 (dd, 2H), 7.56 (d, 2H), 7.36-7.30 (m, 2H), 7.14-7.09 (m, 2H), 7.02 (d, 2H), 6.94 (d, 2H), 5.85 (s, 1H), 1.65 (s, 12H)

Synthesis of Intermediate I-2

4.01 g (10.0 mmol) of Intermediate I-1, 1.12 g (0.5 mmol) of palladium (II) acetate (Pd(OAc)$_2$), and 1.38 g (10.0 mmol) of K$_2$CO$_3$ were dissolved in 20 mL of acetic acid, and the mixture was refluxed at 110° C. for 24 hours. The mixture was cooled to room temperature and subjected to extraction three times with 40 mL of water and 50 mL of diethyl ether. An organic layer was collected and dried using magnesium sulfate to evaporate the solvent. The residue was separately purified using silica gel column chromatography to obtain 68 g of Intermediate I-2 (Yield: 67%) The produced compound was identified using $^1$H NMR and MS/FAB. C$_{30}$H$_{25}$N:calc. 399.20. found 400.19.

$^1$H NMR (400 MHz, CDCl$_3$) δ 8.58 (d, 2H), 8.12 (s, 1H), 7.96 (dd, 2H), 7.42 (s, 2H), 7.34-7.21 (m, 6H), 1.68 (s, 12H)

Synthesis of Compound 3

2 g (5.0 mmol) of Intermediate I-2, 1.83 g (5.5 mmol) of Intermediate I-3 synthesized from 2,6-dibromonaphthalene, 95.0 mg (0.5 mmol) of CuI, 66.1 mg (0.25 mmol) of 18-Crown-6, and 2.07 g (15.0 mmol) of K$_2$CO$_3$ were dissolved in 20 mL of 1,3-dimethyl-3,4,5,6-tetrahydro-2(1H)-pyrimidinone (DMPU), and the mixture was refluxed at 170° C. for 12 hours. The mixture was cooled to room temperature and subjected to extraction three times with 30 mL of water and 40 mL of diethyl ether. An organic layer was collected and dried using magnesium sulfate to evaporate the solvent. The residue was separately purified using silica gel column chromatography to obtain 2.54 g of Compound 3 (Yield: 78%). The produced compound was identified using $^1$H NMR and MS/FAB. C$_{50}$H$_{37}$N:calc. 651.29. found 652.31.

$^1$H NMR (400 MHz, CDCl$_3$) δ 8.41 (s, 2H), 8.21 (s, 1H), 8.18 (s, 1H), 7.98-7.84 (9H), 7.72 (d, 1H), 7.65-7.57 (m, 2H), 7.53-7.49 (m, 3H), 7.34-7.20 (m, 6H), 1.69 (s, 12H).

Synthesis Example 2

Synthesis of Compound 20

Reaction Scheme 2

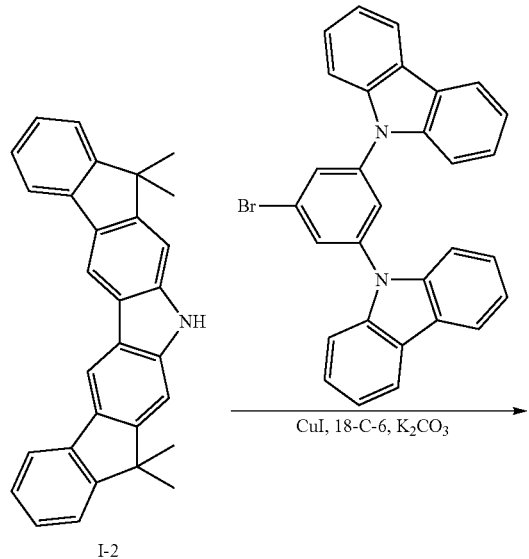

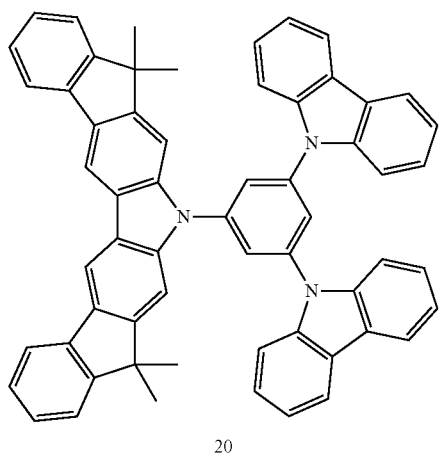

3.02 g of Compound 20 was synthesized with a yield of 75% in the same manner as in Synthesis Example 1 by a reaction between Intermediate I-2 and

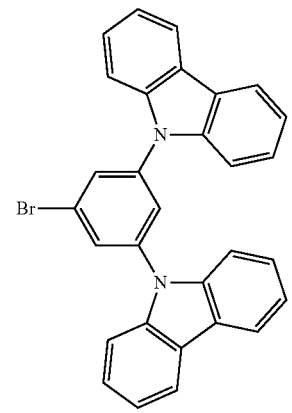 [SMILES: Brc1cc(-n2c3ccccc3c3ccccc32)cc(-n2c3ccccc3c3ccccc32)c1]

synthesized from carbazole. The produced compound was identified using $^1$H NMR and MS/FAB. C$_{60}$H$_{43}$N$_3$:calc. 805.35. found 806.34.

$^1$H NMR (400 MHz, CDCl$_3$) δ 8.46 (s, 2H), 8.11 (d, 4H), 7.92 (dd, 2H), 7.58 (s, 2H), 7.39-7.34 (m, 8H), 7.33-7.21 (m, 13H), 1.68 (s, 12H)

Synthesis Example 3

Synthesis of Compound 52

Reaction Scheme 3

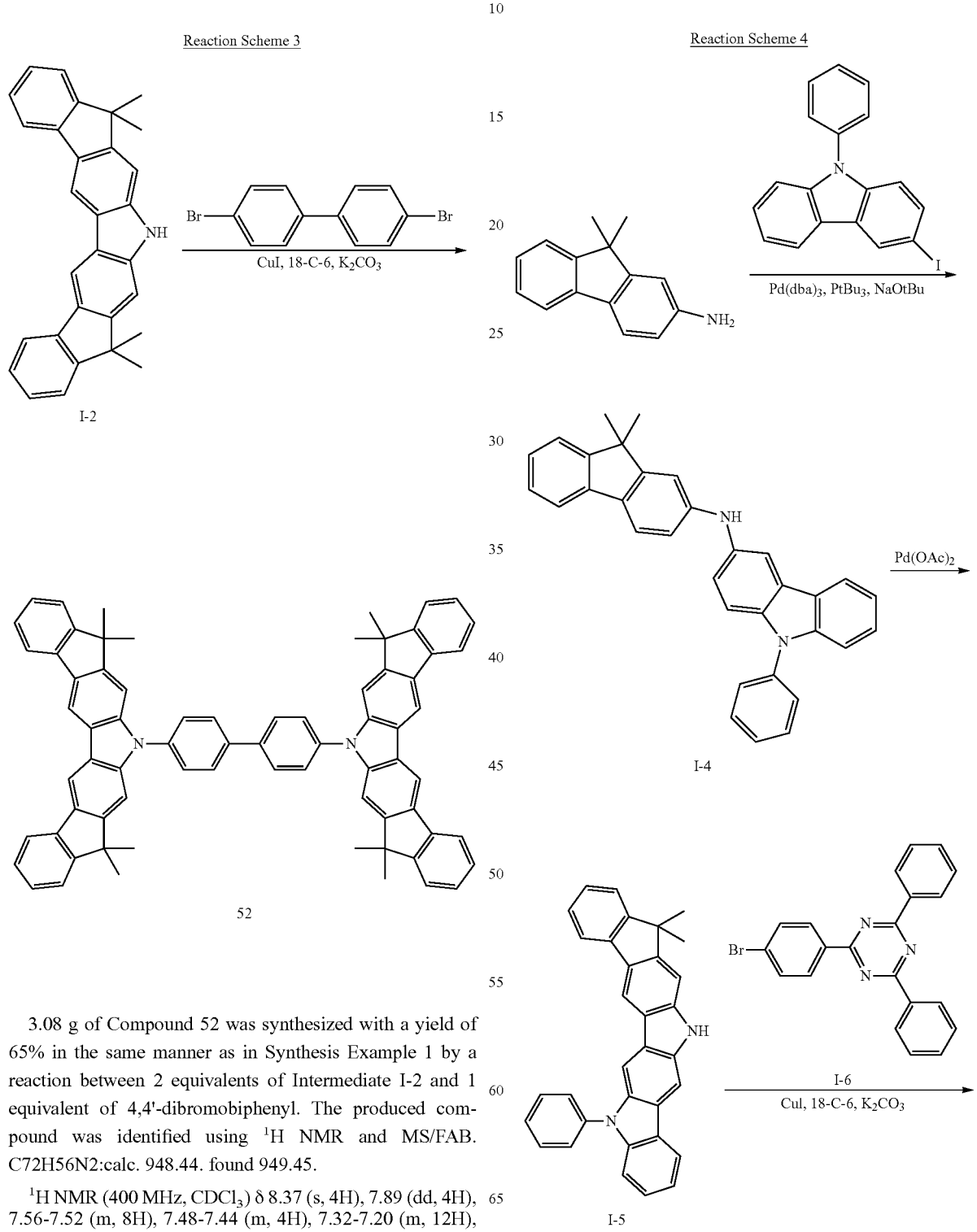

3.08 g of Compound 52 was synthesized with a yield of 65% in the same manner as in Synthesis Example 1 by a reaction between 2 equivalents of Intermediate I-2 and 1 equivalent of 4,4'-dibromobiphenyl. The produced compound was identified using $^1$H NMR and MS/FAB. C72H56N2:calc. 948.44. found 949.45.

$^1$H NMR (400 MHz, CDCl$_3$) δ 8.37 (s, 4H), 7.89 (dd, 4H), 7.56-7.52 (m, 8H), 7.48-7.44 (m, 4H), 7.32-7.20 (m, 12H), 1.69 (s, 24H)

Synthesis Example 4

Synthesis of Compound 60

Reaction Scheme 4

-continued

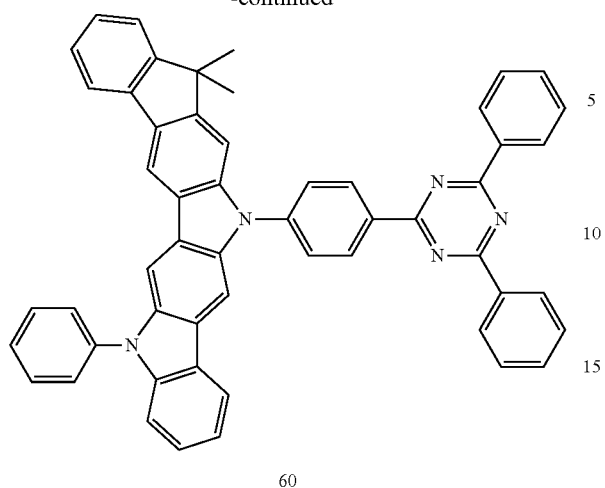

60

Synthesis of Intermediate I-4

48 g of Intermediate I-4 was synthesized with a yield of 83% in the same manner as in the synthesis of Intermediate I-1, using 2-amino-9,9-dimethyl fluorene and 3-iodo-9-phenylcarbazole instead of 2-bromo-9,9'-dimethylfluorene. The produced compound was identified using MS/FAB. $C_{33}H_{26}N_2$: calc. 450.21. found 451.22.

Synthesis of Intermediate I-5

2.51 g of Intermediate I-5 was synthesized with a yield of 56% in the same manner as the synthesis of Intermediate I-2, using Intermediate I-4 instead of Intermediate I-1. The produced compound was identified using $^1$H NMR and MS/FAB. $C_{33}H_{24}N_2$: calc. 448.19. found 449.22.

$^1$H NMR (400 MHz, CDCl$_3$) δ 8.24 (s, 1H), 8.16 (s, 1H), 8.15 (s, 1H), 8.13-8.10 (m, 2H), 7.95 (dd, 1H), 7.54-7.51 (m, 5H), 7.47 (s, 1H), 7.41-7.38 (2H), 7.32-7.20 (m, 4H), 1.66 (s, 6H)

Synthesis of Compound 60

2.72 g of Compound 60 was synthesized with a yield of 72% in the same manner as in the synthesis of Compound 3, using Intermediate I-5 and Intermediate I-6 that was synthesized from 2-chloro-4,6-diphenyltriazine, instead of using Intermediate I-2 and Intermediate I-3. The produced compound was identified using $^1$H NMR and MS/FAB. $C_{54}H_{37}N_5$: calc. 755.30. found 756.32.

$^1$H NMR (400 MHz, CDCl$_3$) δ 8.79 (d, 4H), 8.64 (d, 2H), 8.42 (s, 1H), 8.27 (s, 1H), 8.17 (d, 1H), 8.05 s, 1H), 7.88 (dd, 1H), 7.64-7.59 (m, 5H), 7.52-7.49 (m, 5H), 7.42-7.37 (m, 4H), 7.35-7.23 (m, 6H), 1.67 (s, 6H)

Synthesis Example 5

Synthesis of Compound 68

Reaction Scheme 5

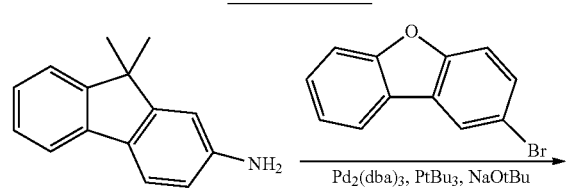

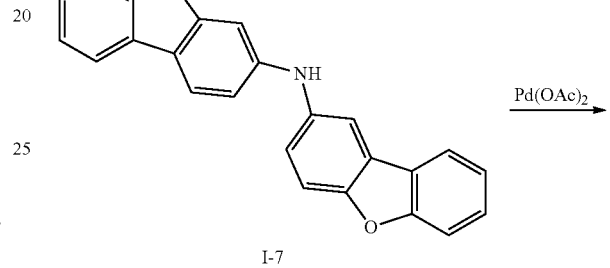

I-7

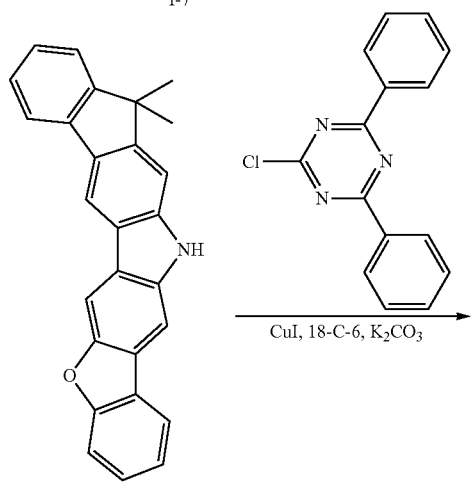

I-8

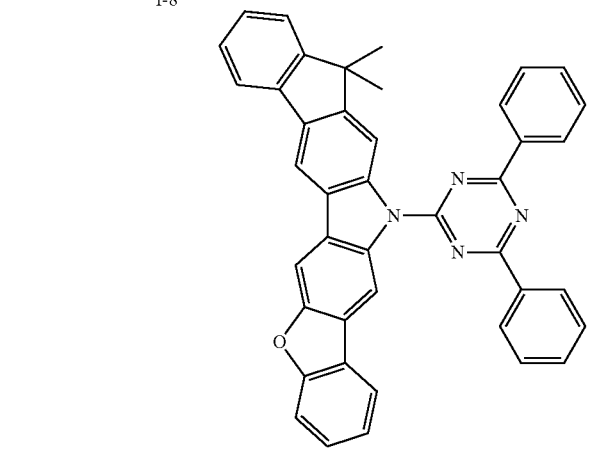

68

Synthesis of Intermediate I-7

6.53 g of Intermediate I-7 was synthesized with a yield of 87% in the same manner as in the synthesis of Intermediate I-1, using 2-amino-9,9-dimethyl fluorene and 2-bromodibenzofuran instead of 2-bromo-9,9'-dimethylfluorene. The produced compound was identified using MS/FAB. $C_{27}H_{21}NO$: calc. 375.16. found 376.16.

Synthesis of Intermediate I-8

2.28 g of Intermediate I-8 was synthesized with a yield of 61% in the same manner as in the synthesis of Intermediate I-2, using Intermediate I-7 instead of Intermediate I-1. The produced compound was identified using $^1$H NMR and MS/FAB. $C_{27}H_{19}NO$:calc. 373.15. found 374.16.

$^1$H NMR (400 MHz, CDCl$_3$) δ 8.58 (s, 1H), 8.14 (s, 1H), 8.10 (s, 1H), 7.96 (dd, 1H), 7.91 (s, 1H), 7.89 (dd, 1H), 7.76 (dd, 1H), 7.56 (t, 1H), 7.37 (t, 2H), 7.33-7.20 (m, 3H), 1.65 (s, 61-1)

Synthesis of Compound 68

1.57 g of Compound 68 was synthesized with a yield of 52% in the same manner as in the synthesis of Compound 3, using Intermediate I-8 and 2-chloro-4,6-diphenyltriazine instead of using Intermediate I-2 and Intermediate I-3. The produced compound was identified using $^1$H NMR and MS/FAB. $C_{42}H_{28}N_4O$:calc. 604.23. found 605.25.

$^1$H NMR (400 MHz, CDCl$_3$) δ 8.76 (d, 4H), 8.44 (s, 1H), 8.37 (s, 1H), 8.34 (s, 1H), 7.89 (dd, 2H), 7.83 (dd, 1H), 7.76 (s, 1H), 7.69-7.64 (m, 4H), 7.56 (t, 1H), 7.47-7.38 (m, 3H) 7.32-7.21 (m, 3H), 1.67 (s, 6H)

Synthesis Example 6

Synthesis of Compound 72

Reaction Scheme 6

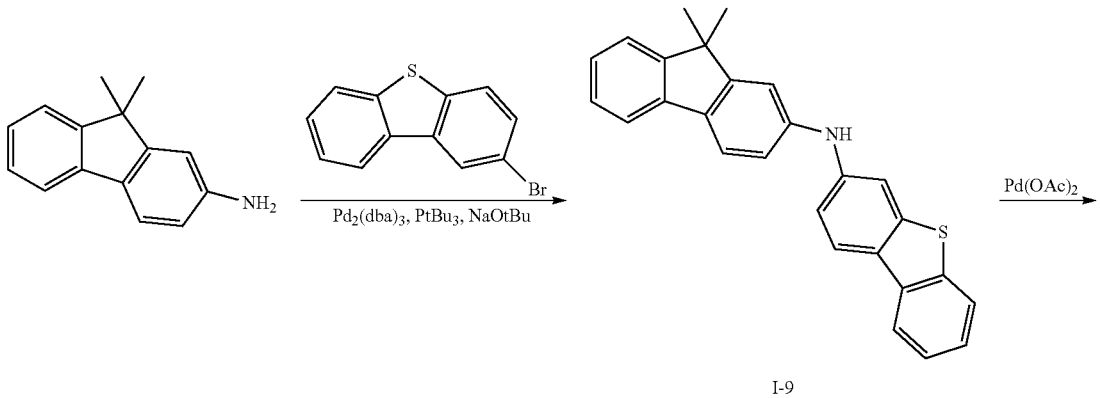

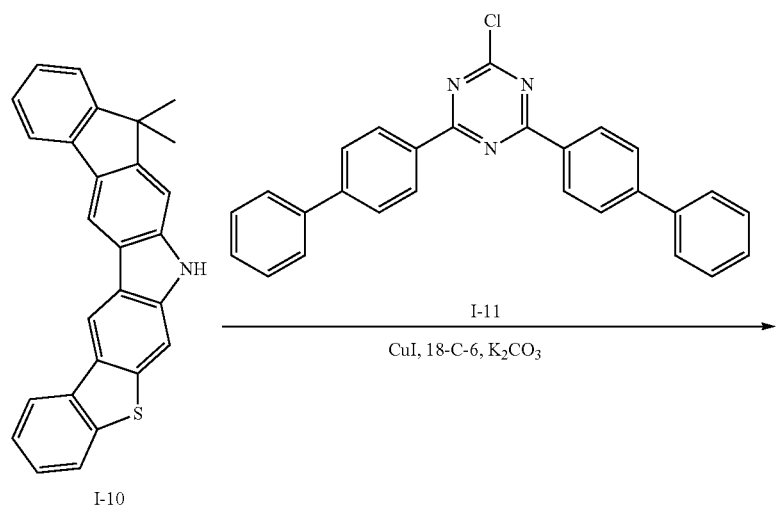

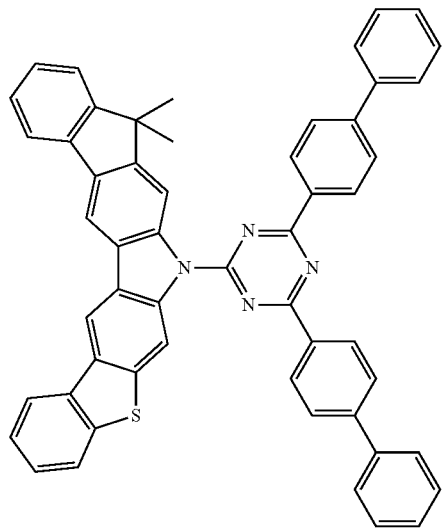

72

Synthesis of Intermediate I-9

6.49 g of Intermediate I-9 was synthesized with a yield of 83% in the same manner as in the synthesis of Intermediate I-1. using 2-amino-9,9-dimethyl fluorene and 3-bromodibenzothiophene instead of 2-bromo-9,9'-dimethylfluorene. The produced compound was identified using MS/FAB. $C_{27}H_{21}NS$:calc. 391.14. found 392.14.

Synthesis of Intermediate I-10

2.57 g of Intermediate I-10 was synthesized with a yield of 66% in the same manner as the synthesis of Intermediate I-2, using Intermediate I-9 instead of Intermediate I-1. The produced compound was identified using $^1$H NMR and MS/FAB. $C_{27}H_{19}NS$:calc. 389.12. found 390.13.
$^1$H NMR (400 MHz, CDCl$_3$) δ 9.04 (s, 1H), 8.21 (s, 1H), 8.15 (s, 1H), 8.10 (d, 1H), 7.95 (dd, 1H) 7.88 (s, 1H), 7.76 (dd, 1H), 7.61-7.51 (m, 2H), 7.37 (s, 1H), 7.36-7.24 (m, 3H), 1.64 (s, 6H)

Synthesis of Compound 72

2.09 g of Compound 72 was synthesized with a yield of 54% in the same manner as in the synthesis of Compound 3 using Intermediate I-10 and Intermediate I-11 instead of using Intermediate I-2 and Intermediate I-3. The produced compound was identified using $^1$H NMR and MS/FAB. $C_{54}H_{36}N_4S$:calc. 772.27. found 773.36.
$^1$H NMR (400 MHz, CDCl$_3$) δ 9.15 (s, 1H), 8.57 (s, 1H), 8.45 (d, 4H), 8.38 (s, 1H), 8.12 (dd, 1H), 8.01-7.97 (m, 4H), 7.92 (d, 1H), 7.77-7.74 (m, 2H), 7.62-7.49 (m, 10H), 7.42-7.38 (m, 2H), 7.33-7.21 (m, 3H), 1.64 (s, 6H)

Synthesis Example 7

Synthesis of Compound 1

Compound 1 was synthesized in the same manner as in Synthesis Example 1, except that Intermediate I-12 was used instead of Intermediate I-3. The produced compound was identified using $^1$H NMR and MS/FAB. $C_{42}H_{33}N$:calc. 551.26. found 552.27.

$^1$H NMR (400 MHz, CDCl$_3$) δ 8.37 (s, 2H), 7.93 (dd, 2H), 7.66-7.60 (m, 2H), 7.55 (s, 2H), 7.52-7.38 (m, 7H), 7.34-7.22 (m, 6H), 1.67 (s, 12H)

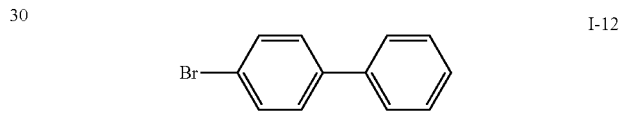

I-12

Synthesis Example 8

Synthesis of Compound 8

Compound 8 was synthesized in the same manner as in Synthesis Example 1, except that Intermediate I-13 was used instead of Intermediate I-3. The produced compound was identified using $^1$H NMR and MS/FAB. $C_{54}H_{39}N$:calc. 701.31. found 702.32.
$^1$H NMR (400 MHz, CDCl$_3$) δ 8.43 (s, 2H), 8.16 (dd, 2H), 7.92 (dd, 2H), 7.84 (d, 1H), 7.72-7.69 (m, 2H), 7.64 (dd, 1H), 7.60-7.50 (m, 4H), 7.46-7.44 (m, 1H), 7.41 (s, 2H), 7.38-7.19 (m, 9H), 6.98 (dt (1H), 1.68 (s, 12H)

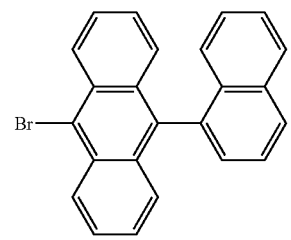

I-13

Synthesis Example 9

Synthesis of Compound 13

Compound 13 was synthesized in the same manner as in Synthesis Example 1, except that Intermediate I-14 was used instead of Intermediate I-3. The produced compound was identified using $^1$H NMR and MS/FAB. $C_{66}H_{53}N$:calc. 859.42. found 860.40.

$^1$H NMR (400 MHz, CDCl$_3$) δ 8.45 (s, 2H), 7.94 (dd, 2H), 7.80 (dd, 2H), 7.74-7.72 (m, 3H), 7.57-7.50 (m, 6H), 7.35-7.20 (m, 10H), 7.15-7.09 (m, 4H), 1.67 (s, 12H), 1.59 (s, 12H)

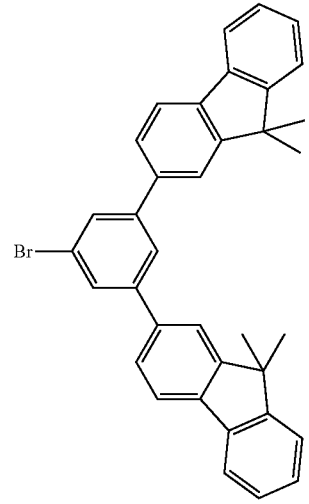

I-14

Synthesis Example 10

Synthesis of Compound 15

Compound 15 was synthesized in the same manner as in Synthesis Example 1, except that Intermediate I-15 was used instead of Intermediate I-3. The produced compound was identified using $^1$H NMR and MS/FAB. $C_{51}H_{41}N$:calc. 667.32. found 668.33.

$^1$H NMR (400 MHz, CDCl$_3$) δ 8.37 (s, 2H), 7.93 (dd, 2H), 7.81 (dd, 1H), 7.72 (d, 1H), 7.56 (dd, 1H), 7.55 (s, 2H), 7.47-7.42 (m, 4H), 7.35-7.19 (m, 8H), 7.14-7.09 (m, 2H), 1.68 (s, 12H), 1.58 (s, 6H)

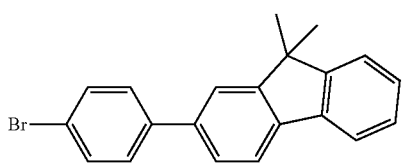

I-15

Synthesis Example 11

Synthesis of Compound 18

Compound 18 was synthesized in the same manner as in Synthesis Example 1, except that Intermediate I-16 was used instead of Intermediate I-3. The produced compound was identified using $^1$H NMR and MS/FAB. $C_{48}H_{36}N_2$:calc. 640.29. found 641.30.

$^1$H NMR (400 MHz, CDCl$_3$) δ 8.35 (s, 2H), 8.12 (dd, 2H), 7.93 (dd, 2H), 7.64-7.60 (m, 2H), 7.57 (s, 2H), 7.36-7.21 (m, 14H), 1.67 (s, 12H)

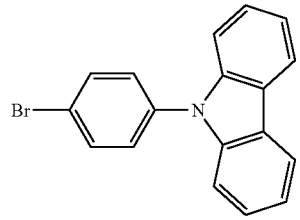

I-16

Synthesis Example 12

Synthesis of Compound 19

Compound 19 was synthesized in the same manner as in Synthesis Example 1, except that Intermediate I-17 was used instead of Intermediate I-3. The produced compound was identified using $^1$H NMR and MS/FAB. $C_{54}H_{40}N_2$:calc. 716.32. found 717.33.

$^1$H NMR (400 MHz, CDCl$_3$) δ 8.35 (s, 2H), 8.13 (dd, 2H), 7.92 (dd, 2H), 7.56-7.51 (m, 6H), 7.48-7.38 (m, 4H), 7.35-7.19 (m, 12H), 1.67 (s, 12H)

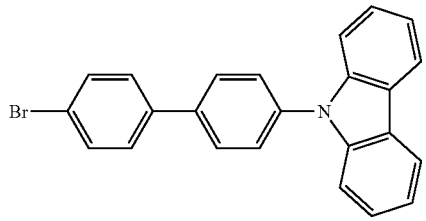

I-17

Synthesis Example 13

Synthesis of Compound 25

Compound 25 was synthesized in the same manner as in Synthesis Example 1, except that Intermediate I-18 was used instead of Intermediate I-3. The produced compound was identified using $^1$H NMR and MS/FAB. $C_{48}H_{35}NS$:calc. 657.25. found 658.27.

$^1$H NMR (400 MHz, CDCl$_3$) δ 8.36 (s, 2H), 8.14 (dd, 1H), 8.10 (dd, 1H), 8.05 (s, 1H), 7.93 (dd, 2H), 7.84 (dd, 1H), 7.80 (d, 1H), 7.53 (s, 2H), 7.50-7.42 (m, 5H), 7.38 (dt, 1H), 7.33-7.18 (m, 6H), 1.66 (s, 12H)

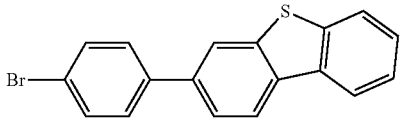

I-18

Synthesis Example 14

Synthesis of Compound 28

Compound 28 was synthesized in the same manner as in Synthesis Example 1, except that Intermediate I-19 was used instead of Intermediate I-3. The produced compound was identified using $^1$H NMR and MS/FAB. $C_{58}H_{44}N_2$:calc. 768.35. found 769.35.

$^1$H NMR (400 MHz, CDCl$_3$) δ 8.37 (s, 2H), 7.93 (dd, 2H), 7.78 (dd, 1H), 7.66 (d, 1H), 7.57-7.37 (m, 12H), 7.34-7.22 (m, 6H), 7.13-7.04 (m, 3H), 6.97-6.93 (m, 2H), 6.86 (dt, 1H), 6.74-6.72 (m, 2H), 1.66 (s, 12H)

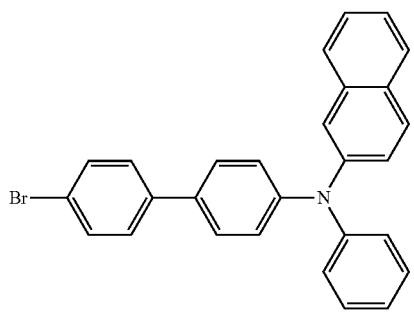

I-19

Synthesis Example 15

Synthesis of Compound 30

Compound 30 was synthesized in the same manner as in Synthesis Example 1, except that Intermediate I-20 was used instead of Intermediate I-3. The produced compound was identified using $^1$H NMR and MS/FAB. $C_{61}H_{48}N_2$:calc. 808.38. found 809.36.

$^1$H NMR (400 MHz, CDCl$_3$) δ 8.41 (s, 2H), 8.13 (d, 1H), 7.92 (dd, 2H), 7.87 (d, 1H), 7.68 (d, 1H), 7.54 (s, 2H), 7.49-7.39 (m, 4H), 7.32-7.19 (m, 8H), 7.11-7.06 (m, 2H), 6.98 (s, 1H), 6.92 (d, 1H), 6.85-6.78 (m, 2H), 6.73 (d, 1H), 6.62-6.60 (m, 2H), 1.67 (s, 12H), 1.58 (s, 6H)

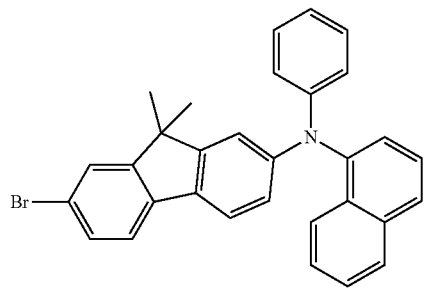

I-20

Synthesis Example 16

Synthesis of Compound 32

Compound 32 was synthesized in the same manner as in Synthesis Example 1, except that Intermediate I-21 was used instead of Intermediate I-3. The produced compound was identified using $^1$H NMR and MS/FAB. $C_{54}H_{40}N_2O$:calc. 732.31. found 733.33.

$^1$H NMR (400 MHz, CDCl$_3$) δ 8.41 (s, 2H), 7.97 (s, 1H), 7.92 (dd, 2H), 7.55-7.53 (m, 5H), 7.44 (dd, 1H), 7.33 (dt, 2H), 7.25-7.20 (m, 4H), 7.09-7.04 (m, 4H), 6.97 (dd, 1H), 6.86 (dt, 2H), 6.74-6.72 (m, 4H), 1.68 (s, 12H)

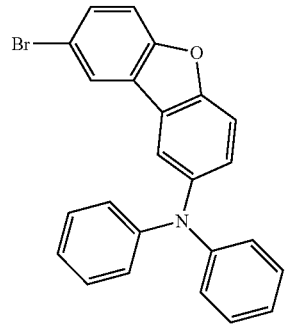

I-21

Synthesis Example 17

Synthesis of Compound 35

Compound 35 was synthesized in the same manner as in Synthesis Example 1, except that Intermediate I-22 was used instead of Intermediate I-3. The produced compound was identified using $^1$H NMR and MS/FAB. $C_{60}H_{47}$NSi:calc. 809.35. found 810.36.

$^1$H NMR (400 MHz, CDCl$_3$) δ 8.37 (s, 2H), 7.92 (dd, 2H), 7.60-7.57 (m, 6H), 7.55 (s, 2H), 7.49-7.42 (m, 8H), 7.34-7.19 (m, 15H), 1.67 (s, 12H)

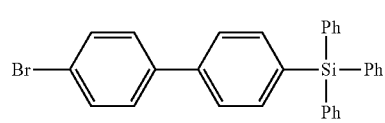

I-22

Synthesis Example 18

Synthesis of Compound 39

Compound 39 was synthesized in the same manner as in Synthesis Example 1, except that Intermediate I-23 was used instead of Intermediate I-3. The produced compound was identified using $^1$H NMR and MS/FAB. $C_{51}H_{38}N_4$:calc. 706.31. found 707.34.

$^1$H NMR (400 MHz, CDCl$_3$) δ 9.07 (s, 2H), 8.66-8.64 (m, 2H), 8.38 (s, 2H), 8.23-8.20 (m, 2H), 7.92 (dd, 2H), 7.65-7.61 (m, 4H), 7.56 (s, 2H), 7.49-7.45 (m, 2H), 7.42-7.38 (m, 2H), 7.32-7.28 (m, 2H), 7.25-7.19 (m, 4H), 1.68 (s, 12H)

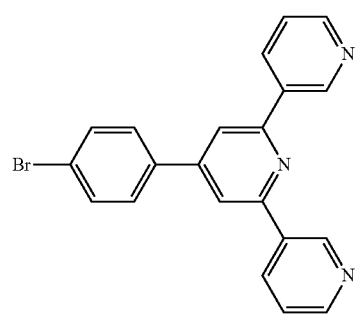

I-23

Synthesis Example 19

Synthesis of Compound 41

Compound 41 was synthesized in the same manner as in Synthesis Example 1, except that Intermediate I-24 was used instead of Intermediate I-3. The produced compound was identified using $^1$H NMR and MS/FAB. $C_{49}H_{37}N_3$:calc. 667.30. found 668.30.

$^1$H NMR (400 MHz, CDCl$_3$) δ 8.37 (s, 2H), 7.94-7.90 (m, 4H), 7.79 (dd, 1H), 7.66 (dd, 1H), 7.58-7.54 (m, 4H), 7.44-7.35 (m, 5H), 7.32-7.19 (m, 8H), 1.68 (s, 12H)

I-24

Synthesis Example 20

Synthesis of Compound 45

Compound 45 was synthesized in the same manner as in Synthesis Example 1, except that Intermediate I-25 was used instead of Intermediate I-3. The produced compound was identified using $^1$H NMR and MS/FAB. $C_{42}H_{32}N_4$:calc. 592.26. found 593.27.

$^1$H NMR (400 MHz, CDCl$_3$) δ 8.49 (d, 1H), 8.42 (d, 1H), 8.37 (s, 2H), 7.95 (s, 1H), 7.91 (dd, 2H), 7.71-7.67 (m, 2H), 7.57-7.53 (m, 4H), 7.32-7.19 (m, 6H), 6.82 (dd, 1H), 1.67 (s, 12H)

I-25

Synthesis Example 21

Synthesis of Compound 48

Compound 48 was synthesized in the same manner as in Synthesis Example 1, except that Intermediate I-26 was used instead of Intermediate I-3. The produced compound was identified using $^1$H NMR and MS/FAB. $C_{65}H_{50}N_2$:calc. 858.40. found 859.42.

$^1$H NMR (400 MHz, CDCl$_3$) δ 8.37 (s, 2H), 7.92 (dd, 2H), 7.78 (dd, 1H), 7.56-7.45 (m, 7H), 7.41-7.19 (m, 9H), 7.14-7.04 (m, 6H), 6.89-6.83 (m, 2H), 6.78 (d, 1H), 6.72-6.69 (m, 2H), 1.68 (s, 12H) 1.61 (s, 6H)

I-26

Synthesis Example 22

Synthesis of Compound 51

Compound 51 was synthesized in the same manner as in Synthesis Example 3, except that 1,2-bis(4-bromophenyl)ethyne was used instead of 4,4'-dibromobiphenyl. The produced compound was identified using $^1$H NMR and MS/FAB. $C_{74}H_{56}N_2$: calc. 972.44. found 973.43.

$^1$H NMR (400 MHz, CDCl$_3$) δ 8.38 (s, 4H), 7.92 (dd, 4H), 7.55 (s, 4H), 7.49-7.45 (m, 4H), 7.41-7.38 (m, 4H), 7.32-7.19 (m, 12H), 1.68 (s, 24H)

Synthesis Example 23

Synthesis of Compound 55

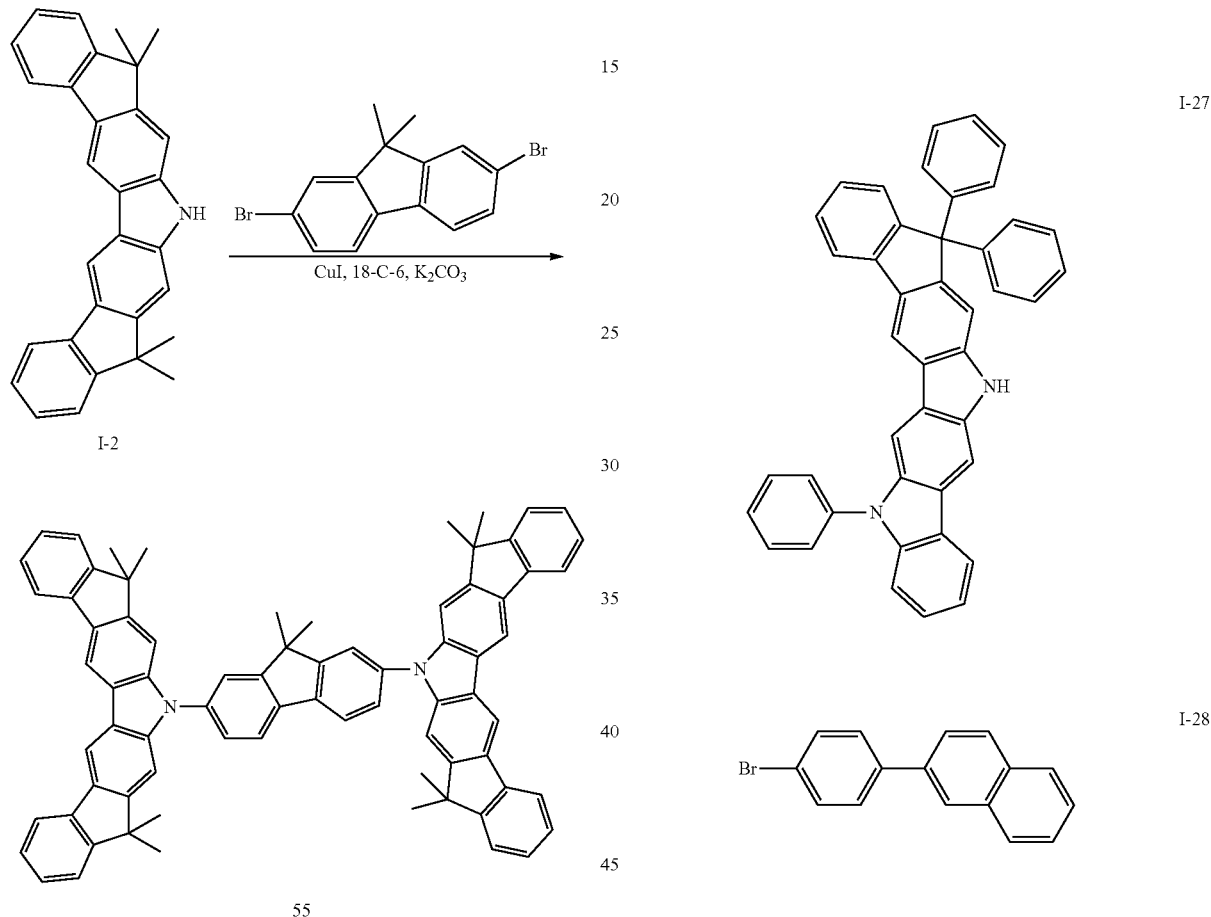

Compound 55 was synthesized in the same manner as in Synthesis Example 3, except that 2.7-dibromo-9,9'-dimethylfluorene was used instead of 4,4'-dibromobiphenyl. The produced compound was identified using $^1$H NMR and MS/FAB. C$_{75}$H$_{60}$N$_2$:calc. 988.48. found 989.46.

$^1$H NMR (400 MHz, CDCl$_3$) δ 8.41 (s, 4H), 7.92 (dd, 4H), 7.58 (d, 2H), 7.54 (s, 4H), 7.32-7.19 (m, 14H), 7.00 (dd, 2H), 1.68 (s, 24H), 1.60 (s, 6H)

Synthesis Example 24

Synthesis of Compound 56

Compound 56 was synthesized in the same manner as in Synthesis Example 4, except that 2-amino-9,9'-diphenylfluorene was used instead of 2-amino-9,9'-dimethylfluorene and Intermediates I-27 and I-28 were respectively used instead of Intermediates I-5 and I-6. The produced compound was identified using $^1$H NMR and MS/FAB. C$_{59}$H$_{38}$N$_2$:calc. 774.30. found 775.31.

$^1$H NMR (400 MHz, CDCl$_3$) δ 8.17-8.15 (m, 3H), 8.07-8.05 (m, 2H), 8.00 (dd, 1H), 7.90-7.84 (m, 3H), 7.76-7.74 (m, 1H), 7.62-7.57 (m, 1H), 7.54-7.48 (m, 8H), 7.44-7.38 (m, 5H), 7.27-7.17 (m, 7H), 7.14-7.06 (m, 6H), 6.91-6.89 (m, 1H)

Synthesis Example 25

Synthesis of Compound 62

Compound 62 was synthesized in the same manner as in Synthesis Example 4, except that Intermediate I-29 was used instead of Intermediate I-6. The produced compound was identified using $^1$H NMR and MS/FAB. C$_{51}$H$_{34}$N$_2$:calc. 674.27. found 675.28.

$^1$H NMR (400 MHz, CDCl$_3$) δ 8.42 (s, 1H), 8.27 (s, 1H), 8.16 (dd, 1H), 8.06-8.04 (m, 2H), 8.00 (dd, 1H), 7.92-7.87 (m, 2H), 7.80 (dd, 1H), 7.74-7.65 (m, 2H), 7.60 (s, 1H), 7.56-7.45 (m, 8H), 7.42-7.36 (m, 4H), 7.32-7.19 (m, 4H), 1.67 (s, 6H)

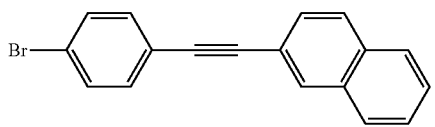

I-29

Synthesis Example 26

Synthesis of Compound 65

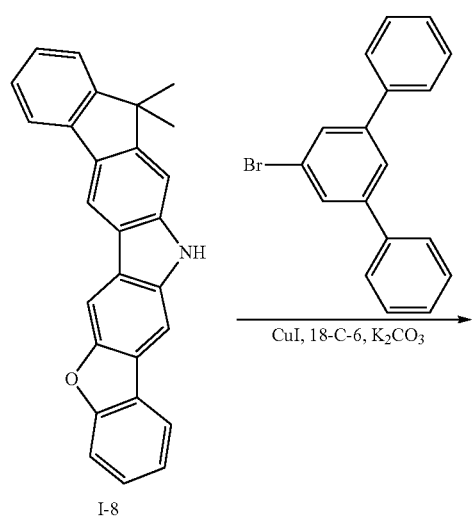

Compound 65 was synthesized in the same manner as in Synthesis Example 5, except that 1-bromo-3,5-diphenylbenzene was used instead of 2-chloro-4,6-diphenyltriazine. The produced compound was identified using $^1$H NMR and MS/FAB. $C_{45}H_{31}NO$:calc. 601.24. found 602.24.

$^1$H NMR (400 MHz, CDCl$_3$) δ 8.38 (s, 1H), 8.26 (s, 1H), 8.16 (s, 1H), 7.92-7.90 (m, 2H), 7.82 (dd, 1H), 7.80-7.77 (m, 4H), 7.57-7.40 (m, 12H), 7.32-7.19 (m, 3H), 1.66 (s, 6H)

Synthesis Example 27

Synthesis of Compound 67

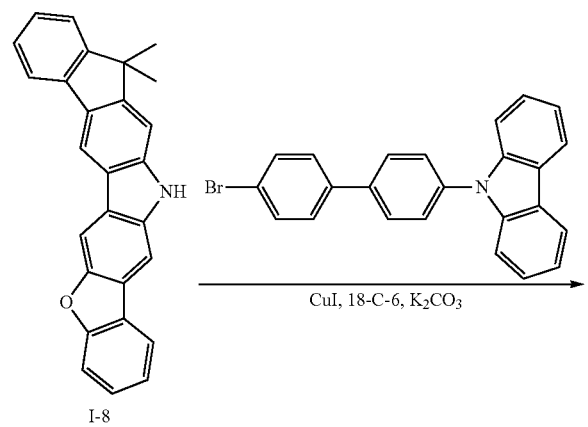

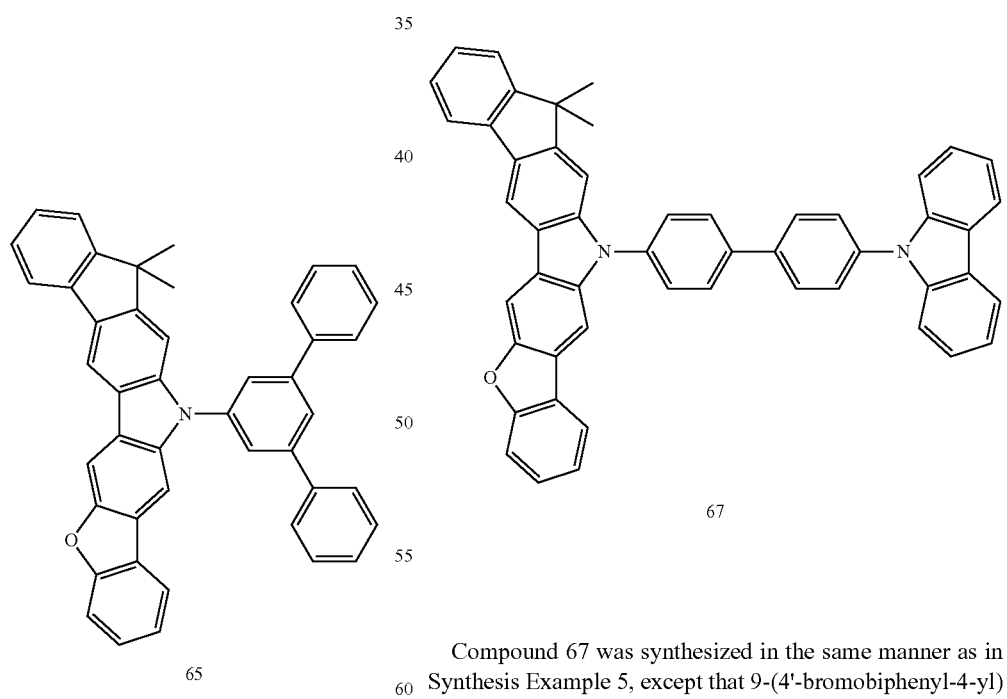

Compound 67 was synthesized in the same manner as in Synthesis Example 5, except that 9-(4'-bromobiphenyl-4-yl)carbazole was used instead of 2-chloro-4,6-diphenyltriazine. The produced compound was identified using $^1$H NMR and MS/FAB. $C_{51}H_{34}N_2O$:calc. 690.27. found 691.29.

$^1$H NMR (400 MHz, CDCl$_3$) δ 8.30 (s, 1H), 8.19 (s, 1H), 8.14-8.10 (m, 3H), 7.92-7.90 (m, 2H), 7.84-7.82 (m, 1H), 7.58-7.38 (m, 11H), 7.35-7.19 (m, 9H), 1.67 (s, 6H)

Synthesis Example 28

Synthesis of Compound 78

Compound 78 was synthesized in the same manner as in Synthesis Example 3, except that, instead of 2 equivalents of Intermediate I-2, 1 equivalent of Intermediate I-2 was first used, and then 1 equivalent of Intermediate I-10 was used. The produced compound was identified using $^1$H NMR and MS/FAB. $C_{69}H_{50}N_2S$:calc. 938.37. found 939.39.

$^1$H NMR (400 MHz, CDCl$_3$) δ 8.93 (s, 1H), 8.36 (s, 2H), 8.30 (s, 1H), 8.10 (dd, 1H), 7.92-7.90 (m, 3H), 7.81 (s, 1H), 7.76-7.74 (m, 1H), 7.61-7.42 (m, 13H), 7.32-7.19 (m, 9H), 1.68 (s, 12H), 1.67 (s, 6H)

Synthesis Example 29

Synthesis of Compound 80

Compound 80 was synthesized in the same manner as in Synthesis Example 28, except that Intermediates I-5 and I-8 were used instead of Intermediates I-2 and I-10. The produced compound was identified using $^1$H NMR and MS/FAB. $C_{72}H_{49}N_3O$:calc. 971.39. found 972.40.

1H NMR (400 MHz, CDCl$_3$) δ 8.42 (s, 1H), 8.30 (s, 1H), 8.27 (s, 1H), 8.19-8.14 (3H), 8.05 (s, 1H), 7.92-7.90 (m, 3H), 7.84-7.82 (m, 1H), 7.60-7.38 (m, 19H), 7.32-7.19 (m, 7H), 1.67 (s, 6H), 1.66 (s, 6H)

Synthesis Example 30

Synthesis of Compound 81

Compound 81 was synthesized in the same manner as in Synthesis Example 28, except that Intermediate I-8 was used instead of Intermediate I-2. The produced compound was identified using $^1$H NMR and MS/FAB. $C_{66}H_{44}N_2OS$:calc. 912.32. found 913.33.

$^1$H NMR (400 MHz, CDCl$_3$) δ 8.93 (s, 1H), 8.31-8.30 (m, 2H), 8.19 (s, 1H), 8.14 (s, 1H), 8.10 (dd, 1H), 7.92-7.90 (m, 3H), 7.84-7.74 (m, 3H), 7.61-7.43 (m, 14H), 7.32-7.19 (m, 6H), 1.68 (s, 6H), 1.67 (s, 6H)

Synthesis Example 31

Synthesis of Compound 83

Compound 83 was synthesized in the same manner as in Synthesis Example 28, except that Intermediate I-8 was used instead of Intermediate I-10. The produced compound was identified using $^1$H NMR and MS/FAB. $C_{69}H_{50}N_2O$:calc. 922.39. found 923.40.

$^1$H NMR (400 MHz, CDCl$_3$) δ 8.37 (s, 2H), 8.30 (s, 1H), 8.19 (s, 1H), 8.14 (s, 1H), 7.92-7.90 (m, 4H), 7.84-7.82 (m, 1H), 7.57-7.50 (m, 8H), 7.48-7.43 (m, 5H), 7.32-7.19 (9H), 1.69 (s, 12H), 1.68 (s, 6H)

Example 1

To manufacture an anode, a Corning 15 Ω/cm$^2$ (1200 Å) ITO glass substrate was cut to a size of 50 mm×50 mm×0.7 mm and sonicated in isopropyl alcohol and pure water each for 5 minutes, and then cleaned by irradiation of UV rays for 30 minutes and exposure to ozone. The resulting ITO glass substrate was loaded into a vacuum deposition apparatus. 2-TNATA was vacuum deposited on the ITO glass substrate to form an HIL having a thickness of 600 Å, and then 4.4'-bis[N-(1-naphthyl)-N-phenylamino]biphenyl (NPB) was vacuum deposited on the HIL to form a HTL having a thickness of 300 Å.

Compound 3 as a green fluorescent host and Ir(ppy)$_3$ as a phosphorescent dopant were simultaneously deposited on the HTL in a weight ratio of 93:7 to form an EML with a thickness of 300 Å.

Then, Alq3 was vacuum deposited on the EML to form an ETL having a thickness of 300 Å. LiF was vacuum deposited on the ETL to form an EIL with a thickness of 10 Å and Al was vacuum deposited on the EIL to form a cathode with a thickness of 3,000 Å, thereby completing the manufacture of an organic light-emitting diode.

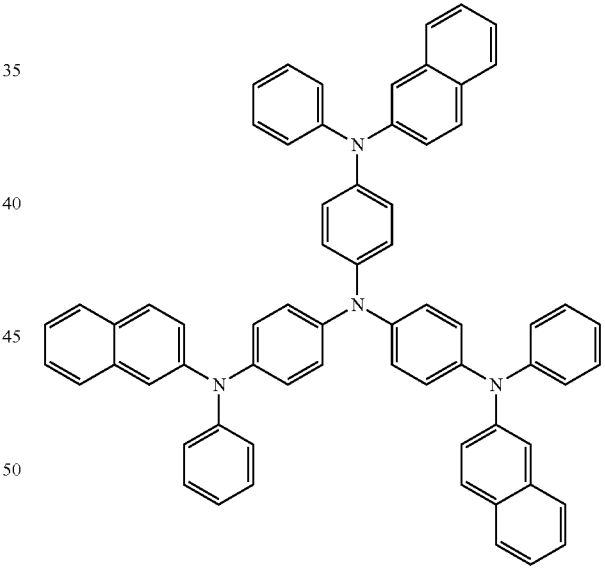

2-TNATA

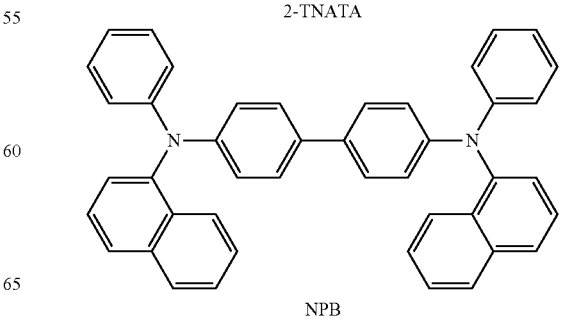

NPB

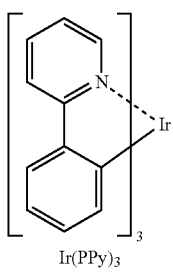

Ir(PPy)₃

Example 2

An organic light-emitting diode was manufactured in the same manner as in Example 1, except that Compound 20 was used instead of Compound 3 when the EML was formed.

Example 3

An organic light-emitting diode was manufactured in the same manner as in Example 1, except that Compound 52 was used instead of Compound 3 as the dopant when the EML was formed.

Example 4

An organic light-emitting diode was manufactured in the same manner as in Example 1, except that Compound 60 was used instead of Compound 3 when the EML was formed.

Example 5

An organic light-emitting diode was manufactured in the same manner as in Example 1, except that Compound 68 was used instead of Compound 3 when the EML was formed.

Example 6

An organic light-emitting diode was manufactured in the same manner as in Example 1, except that Compound 72 was used instead of Compound 3 when the EML was formed.

Comparative Example 1

An organic light-emitting diode was manufactured in the same manner as in Example 1, except that CBP and Ir(ppy)₃, as a green phosphorescent dopant, were simultaneously deposited at a weight ratio of 93:7 instead of Compound 3 used as a phosphorescent host.

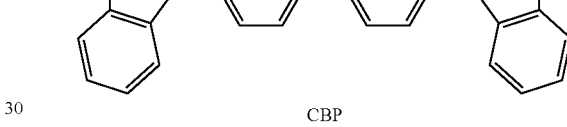

CBP

Evaluation Example

Current density, driving voltage, brightness, and light emission efficiency of the organic light emitting devices according to Examples 1 to 6 and Comparative Example 1 were evaluated using a PR650 Spectroscan Source Measurement Unit. (PhotoReaserch), and the results are shown in Table 1.

TABLE 1

| | Emitting material | Driving voltage (V) | Current density (mA/cm$^2$) | Brightness (cd/m$^2$) | Light emission efficiency (cd/A) | Color (Color coordinates) |
|---|---|---|---|---|---|---|
| Example 1 | Compound 3 | 6 | 17.63 | 3,737 | 21.2 | green (0.30, 0.60) |
| Example 2 | Compound 20 | 6 | 15.22 | 2,480 | 16.3 | green (0.31, 0.60) |
| Example 3 | Compound 52 | 6 | 13.25 | 2,610 | 19.7 | green (0.30, 0.61) |
| Example 4 | Compound 60 | 6 | 19.87 | 4,669 | 23.5 | green (0.30, 0.60) |
| Example 5 | Compound 68 | 6 | 21.56 | 4,894 | 22.7 | green (0.30, 0.60) |
| Example 6 | Compound 72 | 6 | 20.12 | 4,748 | 23.6 | green (0.30, 0.60) |
| Comparative Example 1 | CBP | 6 | 11.17 | 1,268 | 11.35 | green (0.30, 0.60) |

Referring to Table 1, the organic light-emitting diodes including the heterocyclic compound represented by Formula 1 as a host material of a green phosphorescent EML (Examples 1 to 6) had excellent I-V-L characteristics with higher current density, brightness, and efficiency, compared with the organic light-demitting diode including the known material CBP (Comparative Example 1).

In particular, the organic light-emitting diodes, prepared according to Examples 1 to 6 had current density improved by about 20 to 90%, brightness improved by about twice to four times, and efficiency of about 40 to 100%, compared to the organic light-emitting diode prepared according to Comparative Example 1.

Accordingly, the organic light-emitting diode including the heterocyclic compound represented by Formula 1 had high current density and excellent emission efficiency, resulting in having excellent electrical stability, high charge-transporting capability, and excellent emission capability.

As described above, according to the one or more of the above embodiments of the present invention, the heterocyclic compound represented by Formula 1 has high glass transition temperature Tg and prevents crystallization. Thus, an organic light-emitting diode including the heterocyclic compound has high electrical stability, high charge-transporting capability, and excellent light-emitting capability, and thereby having high current density and high light emitting efficiency.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A heterocyclic compound represented by Formula 1 below:

[Formula 1]

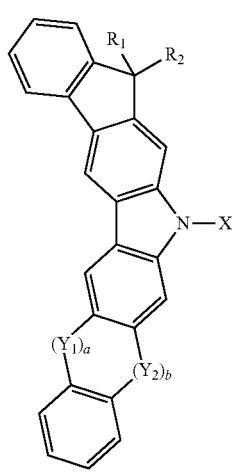

wherein X is *—Ar$_1$ or

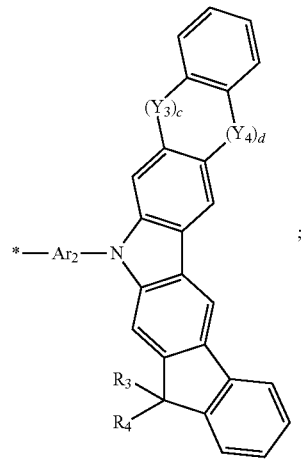

;

wherein Ar$_1$ is a substituted or unsubstituted phenyl group, a substituted or unsubstituted biphenyl group, a substituted or unsubstituted pentalenyl, a substituted or unsubstituted indenyl group, a substituted or unsubstituted naphthyl group, a substituted or unsubstituted azulenyl group, a substituted or unsubstituted heptalenyl group, a substituted or unsubstituted indacenyl group, a substituted or unsubstituted acenaphtyl group, a substituted or unsubstituted fluorenyl group, a substituted or unsubstituted spiro-fluorenyl group, a substituted or unsubstituted phenalenyl group, a substituted or unsubstituted phenanthrenyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted imidazolyl group, a substituted or unsubstituted benzoimidazolyl group, a substituted or unsubstituted phenylbenzoimidazolyl group, a substituted or unsubstituted pyrazolyl group, a substituted or unsubstituted pyridinyl group, a substituted or unsubstituted phenylpyridinyl group, a substituted or unsubstituted phenylimidazopyridinyl group, a substituted or unsubstituted pyrazinyl group, a substituted or unsubstituted pyrimidinyl group, a substituted or unsubstituted phenylimidazopyrimidinyl group, a substituted or unsubstituted pyridazinyl group, a substituted or unsubstituted indolyl group, a substituted or unsubstituted isoindolyl group, a substituted or unsubstituted indazolyl group, a substituted or unsubstituted purinyl group, a substituted or unsubstituted quinolinyl group, a substituted or unsubstituted benzoquinolinyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted cinnolinyl group, a substituted or unsubstituted carbazolyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted furanyl group, a substituted or unsubstituted benzofuranyl group, a substituted or unsubstituted dibenzofuranyl group, a substituted or unsubstituted thiophenyl group, a substituted or unsubstituted benzo[b]thiophenyl group, a substituted or unsubstituted dibenzothiophenyl, a substituted or unsubstituted thiazolyl group, a substituted or unsubstituted isothiazolyl group, a substituted or unsubstituted benzothiazolyl group, a substituted or unsubstituted oxazolyl group, a substituted or unsubstituted isoxazolyl group, a substituted or unsubstituted benzooxazolyl group, a substituted or unsubstituted triazolyl group, a substituted or unsubstituted phenyltriazolyl group, a substituted or unsubstituted tetrazolyl group, a substituted or unsubstituted oxadiazolyl group, a substituted or unsubstituted phenyloxadiazolyl group, a substituted or unsubstituted diphenylethynyl group, a substituted or unsubstituted phenylethynylfluorenyl group, or a substituted or unsubstituted phenylethynylnaphthyl group;

$Ar_2$ is a substituted or unsubstituted $C_6$-$C_{60}$ arylene group, a substituted or unsubstituted $C_6$-$C_{60}$ aryleneoxy group, a substituted or unsubstituted $C_6$-$C_{60}$ arylenethio group, a substituted or unsubstituted $C_2$-$C_{60}$ heteroarylene group, or a substituted or unsubstituted $C_2$-$C_{60}$ polycyclic condensed group;

* indicates a binding site;

$Y_1$, $Y_2$, $Y_3$ and $Y_4$ are each independently $NR_7$, O, or S;

a, b, c and d are each independently an integer of 0 or 1, wherein a+b=1 and c+d=1; and $R_1$, $R_2$, $R_3$, $R_4$, $R_5$, $R_6$ and $R_7$ are each independently a hydrogen atom, a deuterium, a tritium, a halogen atom, a hydroxyl group, a cyano group, a nitro group, a carboxyl group, a silyl group, a substituted or unsubstituted $C_1$-$C_{50}$ alkyl group, a substituted or unsubstituted $C_2$-$C_{50}$ alkenyl group, a substituted or unsubstituted $C_2$-$C_{50}$ alkynyl group, a substituted or unsubstituted $C_1$-$C_{50}$ alkoxy group, a substituted or unsubstituted $C_3$-$C_{50}$ cycloalkyl group, a substituted or unsubstituted $C_3$-$C_{50}$ cycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted $C_2$-$C_{60}$ polycyclic condensed group, or $N(Q_1)(Q_2)$, and $Q_1$ and $Q_2$ are each independently a hydrogen atom, a deuterium, a tritium, a halogen atom, a hydroxyl group, a cyano group, a nitro group, a carboxyl group, a silyl group, a substituted or unsubstituted $C_1$-$C_{50}$ alkyl group, a substituted or unsubstituted $C_2$-$C_{50}$ alkenyl group, a substituted or unsubstituted $C_2$-$C_{50}$ alkynyl group, a substituted or unsubstituted $C_1$-$C_{50}$ alkoxy group, a substituted or unsubstituted $C_3$-$C_{50}$ cycloalkyl group, a substituted or unsubstituted $C_3$-$C_{50}$ cycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, and a substituted or unsubstituted $C_2$-$C_{60}$ polycyclic condensed group, wherein at least two of $R_1$, $R_2$, $R_3$, $R_4$, $R_5$, $R_6$, and $R_7$ which are adjacent to each other bind to each other to form a saturated or unsaturated ring.

2. The heterocyclic compound of claim 1, wherein X is *—$Ar_1$.

3. The heterocyclic compound of claim 1, wherein $Ar_1$ is a substituted or unsubstituted phenyl group, a substituted or unsubstituted biphenyl group, a substituted or unsubstituted naphthyl group, a substituted or unsubstituted fluorenyl group, a substituted or unsubstituted phenanthrenyl group, a substituted or unsubstituted anthryl group, a substituted or unsubstituted triphenylrenyl group, a substituted or unsubstituted pyrenyl group, a substituted or unsubstituted imidazolyl group, a substituted or unsubstituted benzoimidazolyl group, a substituted or unsubstituted phenylbenzoimidazolyl group, a substituted or unsubstituted pyridinyl group, a substituted or unsubstituted phenylpyridinyl group, a substituted or unsubstituted phenylimidazopyridinyl group, a substituted or unsubstituted pyridinyl group, a substituted or unsubstituted phenylimidazopyrimidinyl group, a substituted or unsubstituted carbazolyl group, a substituted or unsubstituted furanyl group, a substituted or unsubstituted benzofuranyl group, a substituted or unsubstituted dibenzofuranyl group, a substituted or unsubstituted thiophenyl group, a substituted or unsubstituted benzo[b]thiophenyl group, a substituted or unsubstituted dibenzothiophenyl group, a substituted or unsubstituted triazolyl group, a substituted or unsubstituted phenyltriazolyl group, a substituted or unsubstituted oxadiazolyl group, a substituted or unsubstituted phenyloxadiazolyl group, a substituted or unsubstituted triazinyl group, a substituted or unsubstituted phenyltriazinyl group, a diphenylethynyl group, a phenylethynylfluorenyl group, or a phenylethynylnaphthyl group.

4. The heterocyclic compound of claim 2, wherein $Ar_1$ is one of the groups represented by Formulae 4A to 4X below:

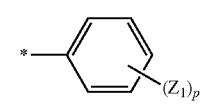

Formula 4A

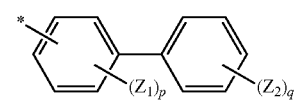

Formula 4B

Formula 4C

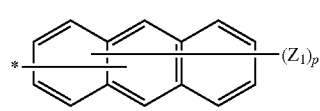

Formula 4D

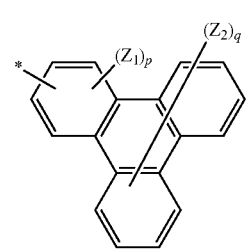

Formula 4E

-continued

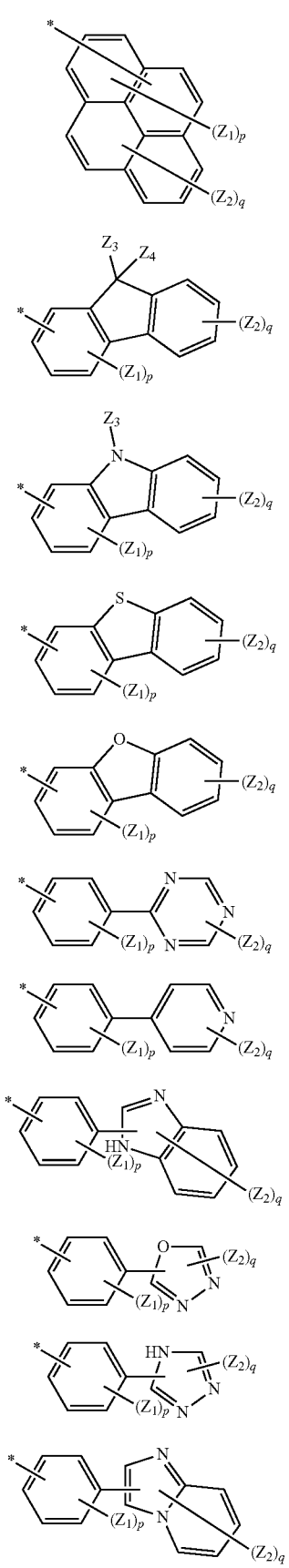

Formula 4F

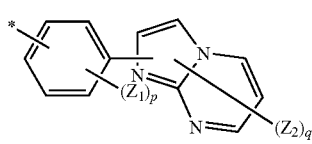

Formula 4G

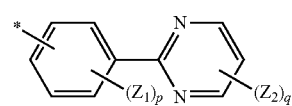

Formula 4R

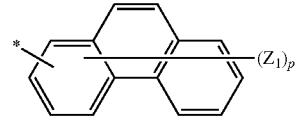

Formula 4S

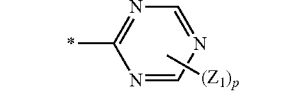

Formula 4T

Formula 4H

Formula 4I

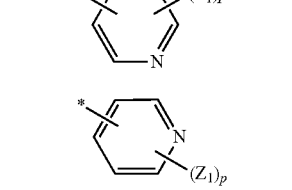

Formula 4U

Formula 4V

Formula 4J

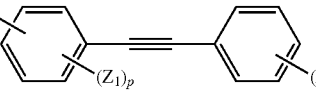

Formula 4W

Formula 4K

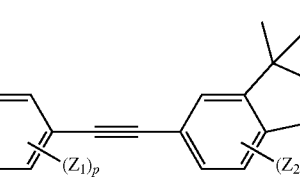

Formula 4X

Formula 4L

Formula 4M

Formula 4N

Formula 4O

Formula 4P wherein $Z_1$, $Z_2$, and $Z_3$ are each independently a hydrogen atom, a deuterium, a tritium, a halogen atom, a hydroxyl group, a cyano group, a nitro group, a carboxyl group, a silyl group, a substituted or unsubstituted $C_1$-$C_{50}$ alkyl group, a substituted or unsubstituted $C_2$-$C_{50}$ alkenyl group, a substituted or unsubstituted $C_2$-$C_{50}$ alkynyl group, a substituted or unsubstituted $C_1$-$C_{50}$ alkoxy group, a substituted or unsubstituted $C_3$-$C_{50}$ cycloalkyl group, a substituted or unsubstituted $C_3$-$C_{50}$ cycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted $C_2$-$C_{60}$ polycyclic condensed group, $N(Q_{11})(Q_{12})$, or $Si(Q_{13})(Q_{14})(Q_{15})$, and $Q_{11}$ to $Q_{15}$ are each independently a hydrogen atom, a deuterium, a tritium, a halogen atom, a hydroxyl group, a cyano group, a nitro group, a carboxyl group, a silyl group, a substituted or unsubstituted $C_1$-$C_{50}$ alkyl group, a substituted or unsubstituted $C_2$-$C_{50}$ alkenyl group, a substituted or unsubstituted $C_2$-$C_{50}$ alkynyl group, a substituted or unsubstituted $C_1$-$C_{50}$ alkoxy group, a substituted or unsubstituted $C_3$-$C_{50}$ cycloalkyl group, a substituted or unsubstituted $C_3$-$C_{50}$ cycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, or a substituted or unsubstituted $C_2$-$C_{60}$ polycyclic condensed group;

* indicates a binding site; and p, q and r are each independently an integer from 1 to 5.

5. The heterocyclic compound of claim 1, wherein X is

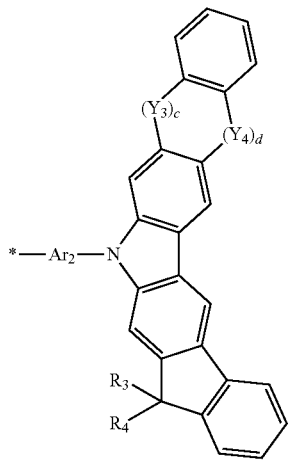

6. The heterocyclic compound of claim 5, wherein $Ar_2$ is a substituted or unsubstituted phenylene group, a substituted or unsubstituted biphenylene group, a substituted or unsubstituted pentalenylene group, a substituted or unsubstituted indenylene group, a substituted or unsubstituted naphtylene group, a substituted or unsubstituted fluorenylene group, a substituted or unsubstituted spiro-fluorenyl group, a substituted or unsubstituted phenalenylene group, a substituted or unsubstituted phenanthrenylene group, a substituted or unsubstituted anthrylene group, a substituted or unsubstituted fluoranthenylene group, a substituted or unsubstituted triphenylenylene group, a substituted or unsubstituted pyrenylene group, a substituted or unsubstituted chrysenylene group, a substituted or unsubstituted carbazolylene group, or a substituted or unsubstituted diphenylethynylene group.

7. The heterocyclic compound of claim 5, wherein $Ar_2$ is one of the groups represented by Formulae 5A to 5E below:

Formula 5A

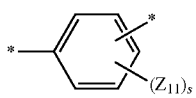

Formula 5B

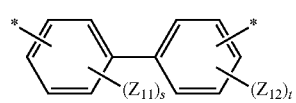

Formula 5C

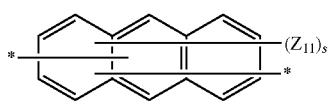

Formula 5D

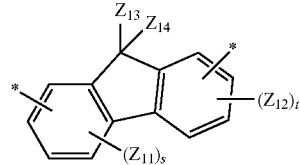

Formula 5E

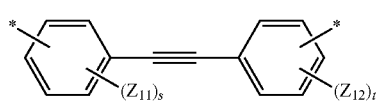

wherein $Z_{11}$, $Z_{12}$, and $Z_{13}$ are each independently a hydrogen atom, a deuterium, a tritium, a halogen atom, a hydroxyl group, a cyano group, a nitro group, a carboxyl group, a silyl group, a substituted or unsubstituted $C_1$-$C_{50}$ alkyl group, a substituted or unsubstituted $C_2$-$C_{50}$ alkenyl group, a substituted or unsubstituted $C_2$-$C_{50}$ alkynyl group, a substituted or unsubstituted $C_1$-$C_{50}$ alkoxy group, a substituted or unsubstituted $C_3$-$C_{50}$ cycloalkyl group, a substituted or unsubstituted $C_3$-$C_{50}$ cycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted $C_2$-$C_{60}$ polycyclic condensed group, $N(Q_{11})(Q_{12})$, or $Si(Q_{13})(Q_{14})(Q_{15})$, and $Q_{11}$ to $Q_{15}$ are each independently a hydrogen atom, a deuterium, a tritium, a halogen atom, a hydroxyl group, a cyano group, a nitro group, a carboxyl group, a silyl group, a substituted or unsubstituted $C_1$-$C_{50}$ alkyl group, a substituted or unsubstituted $C_2$-$C_{50}$ alkenyl group, a substituted or unsubstituted $C_2$-$C_{50}$ alkynyl group, a substituted or unsubstituted $C_1$-$C_{50}$ alkoxy group, a substituted or unsubstituted $C_3$-$C_{50}$ cycloalkyl group, a substituted or unsubstituted $C_3$-$C_{50}$ cycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, or a substituted or unsubstituted $C_2$-$C_{60}$ polycyclic condensed group;

* indicates a binding site; and s and t are each independently an integer from 1 to 4.

8. The heterocyclic compound of claim 1, wherein $R_1$, $R_2$, $R_3$, and $R_4$ are each independently a hydrogen atom, a deuterium, a tritium, a halogen atom, a hydroxyl group, a cyano group, a nitro group, a carboxyl group, a silyl group, a substituted or unsubstituted $C_1$-$C_{50}$ alkyl group, or a substituted or unsubstituted $C_6$-$C_{60}$ aryl group; and $Y_1$, $Y_2$, $Y_3$ and $Y_4$ are each independently $NR_7$, O, and S; and $R_5$, $R_6$, and $R_7$ are each independently a hydrogen atom, a deuterium, a tritium, a halogen atom, a hydroxyl group, a cyano group, a nitro group, a carboxyl group, a silyl group, a substituted or unsubstituted $C_1$-$C_{50}$ alkyl group, or a substituted or unsubstituted $C_6$-$C_{60}$ aryl group.

9. The heterocyclic compound of claim 1, wherein $R_1$, $R_2$, $R_3$, and $R_4$ are each independently a substituted or unsubstituted methyl group, a substituted or unsubstituted ethyl group, a substituted or unsubstituted propyl group, or a substituted or unsubstituted butyl group; and $Y_1$, $Y_2$, $Y_3$, and $Y_4$ are each independently $NR_7$, O, or S; and $R_5$ and $R_6$ are each independently a substituted or unsubstituted methyl group, a substituted or unsubstituted ethyl group, a substituted or unsubstituted propyl group, or a substituted or unsubstituted butyl group, and $R_7$ may be a unsubstituted phenyl group, a substituted or unsubstituted biphenyl group, a substituted or unsubstituted naphthyl group, or a substituted or unsubstituted fluorenyl group.

10. The heterocyclic compound of claim 1, wherein the heterocyclic compound is represented by Formula 6 below:

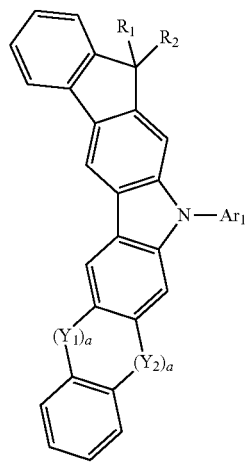

[Formula 6]

wherein $Ar_1$ is a substituted or unsubstituted phenyl group, a substituted or unsubstituted biphenyl group, a substituted or unsubstituted naphthyl group, a substituted or unsubstituted fluorenyl group, a substituted or unsubstituted phenanthrenyl group, a substituted or unsubstituted anthryl group, a substituted or unsubstituted triphenylrenyl group, a substituted or unsubstituted pyrenyl group, a substituted or unsubstituted imidazolyl group, a substituted or unsubstituted benzoimidazolyl group, a substituted or unsubstituted phenylbenzoimidazolyl group, a substituted or unsubstituted pyridinyl group, a substituted or unsubstituted phenylpyridinyl group, a substituted or unsubstituted phenylimidazopyridinyl group, a substituted or unsubstituted pyrimidinyl group, a substituted or unsubstituted phenylimidazopyrimidinyl group, a substituted or unsubstituted carbazolyl group, a substituted or unsubstituted furanyl group, a substituted or unsubstituted benzofuranyl group, a substituted or unsubstituted dibenzofuranyl group, a substituted or unsubstituted thiophenyl group, a substituted or unsubstituted benzo[b]thiophenyl group, a substituted or unsubstituted dibenzothiophenyl group, a substituted or unsubstituted triazolyl group, a substituted or unsubstituted phenyltriazolyl group, a substituted or unsubstituted oxadiazolyl group, a substituted or unsubstituted phenyloxadiazolyl group, a substituted or unsubstituted triazinyl group, a substituted or unsubstituted phenyltriazinyl group, a diphenylethynyl group, a phenylethynylfluorenyl group, or a phenylethynylnaphthyl group;

$R_1$ and $R_2$ are each independently a substituted or unsubstituted methyl group, a substituted or unsubstituted ethyl group, a substituted or unsubstituted propyl group, or a substituted or unsubstituted butyl group;

$Y_1$ and $Y_2$ are each independently $NR_7$, O, or S; $R_5$ and $R_6$ are each independently a substituted or unsubstituted methyl group, a substituted or unsubstituted ethyl group, a substituted or unsubstituted propyl group, or a substituted or unsubstituted butyl group, $R_7$ is a unsubstituted phenyl group, a substituted or unsubstituted biphenyl group, a substituted or unsubstituted naphthyl group, or a substituted or unsubstituted fluorenyl group; and a and b are each independently an integer of 0 or 1, wherein a+b=1.

11. The heterocyclic compound of claim 1, wherein the heterocyclic compound is represented by Formula 7 below:

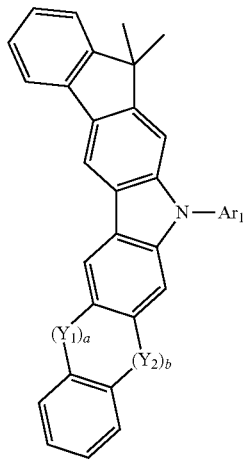

[Formula 7]

$Ar_1$ is one of the groups represented by Formulae 4A to 4X below:

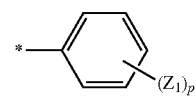

Formula 4A

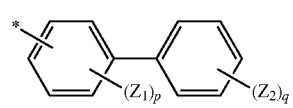

Formula 4B

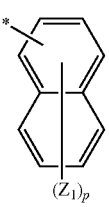

Formula 4C

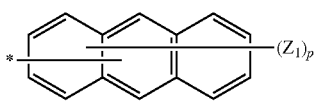

Formula 4D

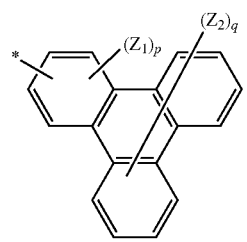

Formula 4E

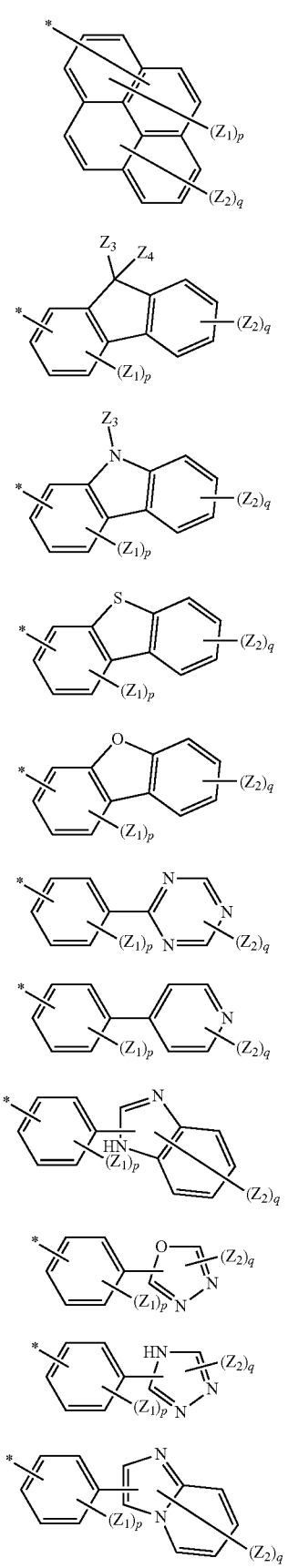

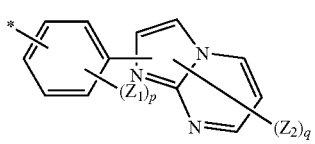
Formula 4Q

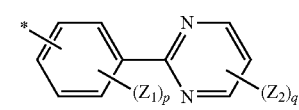
Formula 4R

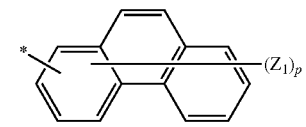
Formula 4S

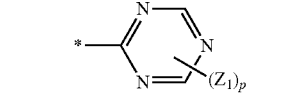
Formula 4T

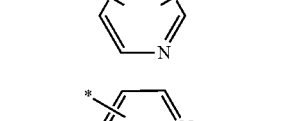
Formula 4U

Formula 4V

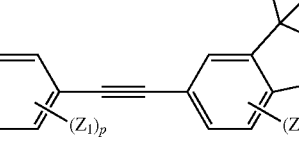
Formula 4W

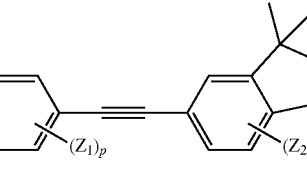
Formula 4X wherein $Z_1$, $Z_2$, and $Z_3$ are each independently a hydrogen atom, a deuterium, a tritium, a halogen atom, a hydroxyl group, a cyano group, a nitro group, a carboxyl group, a silyl group, a substituted or unsubstituted $C_1$-$C_{50}$ alkyl group, a substituted or unsubstituted $C_2$-$C_{50}$ alkenyl group, a substituted or unsubstituted $C_2$-$C_{50}$ alkynyl group, a substituted or unsubstituted $C_1$-$C_{50}$ alkoxy group, a substituted or unsubstituted $C_3$-$C_{50}$ cycloalkyl group, a substituted or unsubstituted $C_3$-$C_{50}$ cycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted $C_2$-$C_{60}$ polycyclic condensed group, $N(Q_{11})(Q_{12})$, or $Si(Q_{13})(Q_{14})(Q_{15})$, and $Q_{11}$ to $Q_{15}$ are each independently a hydrogen atom, a deuterium, a tritium, a halogen atom, a hydroxyl group, a cyano group, a nitro group, a carboxyl group, a silyl group, a substituted or unsubstituted $C_1$-$C_{50}$ alkyl group, a substituted or unsubstituted $C_2$-$C_{50}$ alkenyl group, a substituted or unsubstituted $C_2$-$C_{50}$ alkynyl group, a substituted or unsubstituted $C_1$-$C_{50}$ alkoxy group, a substituted or unsubstituted $C_3$-$C_{50}$ cycloalkyl group, a substituted or unsubstituted $C_3$-$C_{50}$ cycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, or a substituted or unsubstituted $C_2$-$C_{60}$ polycyclic condensed group, and p, q, and r are each independently an integer from 1 to 5;

\* indicates a binding site;

$Y_1$ and $Y_2$ are each independently $NR_7$, O, or S; $R_5$ and $R_6$ are each independently a substituted or unsubstituted methyl group, a substituted or unsubstituted ethyl group, a substituted or unsubstituted propyl group, or a substituted or unsubstituted butyl group, $R_7$ is a unsubstituted phenyl group, a substituted or unsubstituted biphenyl group, a substituted or unsubstituted naphthyl group, or a substituted or unsubstituted fluorenyl group; and a and b are each independently an integer of 0 or 1, wherein a+b=1.

12. The heterocyclic compound of claim 1, wherein the heterocyclic compound is represented by Formula 8 below:

[Formula 8]

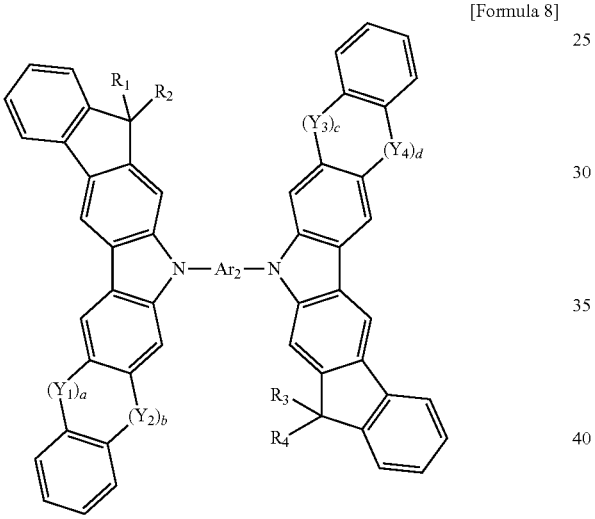

wherein $Ar_2$ is a substituted or unsubstituted phenylene group, a substituted or unsubstituted biphenylene group, a substituted or unsubstituted pentalenyl group, a substituted or unsubstituted indenylene group, a substituted or unsubstituted naphthylene group, a substituted or unsubstituted fluorenylene group, a substituted or unsubstituted spiro-fluorenyl group, a substituted or unsubstituted phenalenyl group, a substituted or unsubstituted phenanthrenyl group, a substituted or unsubstituted anthrylene group, a substituted or unsubstituted fluoranthenylene group, a substituted or unsubstituted triphenylenylene group, a substituted or unsubstituted pyrenylene group, a substituted or unsubstituted chrycenylene group, or a substituted or unsubstituted carbazolylene group, or a substituted or unsubstituted diphenylethynylene group;

$R_1$, $R_2$, $R_3$ and $R_4$ are each independently a substituted or unsubstituted methyl group, a substituted or unsubstituted ethyl group, a substituted or unsubstituted propyl group, or a substituted or unsubstituted butyl group;

$Y_1$, $Y_2$, $Y_3$, and $Y_4$ are each independently $NR_7$, O, or S; $R_5$ and $R_6$ are each independently a substituted or unsubstituted methyl group, a substituted or unsubstituted ethyl group, a substituted or unsubstituted propyl group, or a substituted or unsubstituted butyl group, $R_7$ is a unsubstituted phenyl group, a substituted or unsubstituted biphenyl group, a substituted or unsubstituted naphthyl group, or a substituted or unsubstituted fluorenyl group; and a, b, c, and d are each independently an integer of 0 or 1, wherein a+b=1 and c+d=1.

13. The heterocyclic compound of claim 1, wherein the heterocyclic compound is represented by Formula 9 below:

[Formula 9]

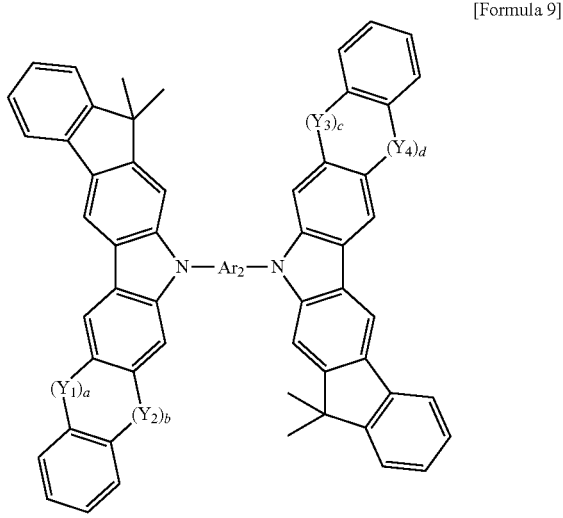

$Ar_2$ is one of the groups represented by Formulae 5A to 5E below:

Formula 5A

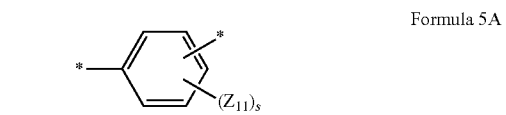

Formula 5B

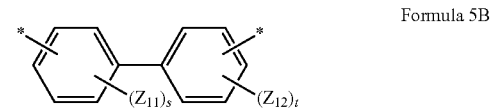

Formula 5C

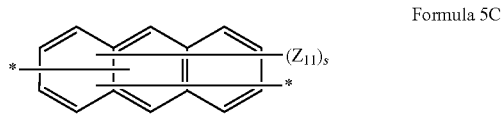

Formula 5D

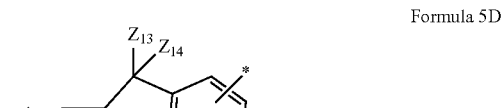

Formula 5E

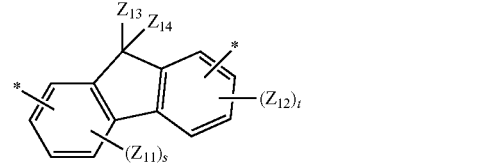

wherein $Z_{11}$, $Z_{12}$, and $Z_{13}$ are each independently a hydrogen atom, a deuterium, a tritium, a halogen atom, a hydroxyl group, a cyano group, a nitro group, a carboxyl group, a silyl group, a substituted or unsubstituted $C_1$-$C_{50}$ alkyl group, a substituted or unsubstituted $C_2$-$C_{50}$ alkenyl group, a substituted or unsubstituted $C_2$-$C_{50}$ alkynyl group, a substituted or unsubstituted $C_1$-$C_{50}$ alkoxy group, a substituted or unsubstituted $C_3$-$C_{50}$ cycloalkyl group, a substituted or unsubstituted $C_3$-$C_{50}$ cycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted $C_2$-$C_{60}$ polycyclic condensed group, $N(Q_{11})(Q_{12})$, or $Si(Q_{13})(Q_{14})(Q_{15})$, and $Q_{11}$ to $Q_{15}$ are each independently a hydrogen atom, a deuterium, a tritium, a halogen atom, a hydroxyl group, a cyano group, a nitro group, a carboxyl group, a silyl group, a substituted or unsubstituted $C_1$-$C_{50}$ alkyl group, a substituted or unsubstituted $C_2$-$C_{50}$ alkenyl group, a substituted or unsubstituted $C_2$-$C_{50}$ alkynyl group, a substituted or unsubstituted $C_1$-$C_{50}$ alkoxy group, a substituted or unsubstituted $C_3$-$C_{50}$ cycloalkyl group, a substituted or unsubstituted $C_3$-$C_{50}$ cycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, or a substituted or unsubstituted $C_2$-$C_{60}$ polycyclic condensed group, and s and t are each independently an integer from 1 to 4;

* indicates a binding site;

$Y_1$, $Y_2$, $Y_3$, and $Y_4$ are each independently $NR_7$, O, or S; $R_5$ and $R_6$ are each independently a substituted or unsubstituted methyl group, a substituted or unsubstituted ethyl group, a substituted or unsubstituted propyl group, or a substituted or unsubstituted butyl group, $R_7$ is a unsubstituted phenyl group, as substituted or unsubstituted biphenyl group, as substituted or unsubstituted naphthyl group, or as substituted or unsubstituted fluorenyl group; and a, b, c, and d are each independently an integer of 0 or 1, wherein a+b=1 and c+d=1.

14. The heterocyclic compound of claim 1, wherein the heterocyclic compound is one of Compounds 1 to 83 below:

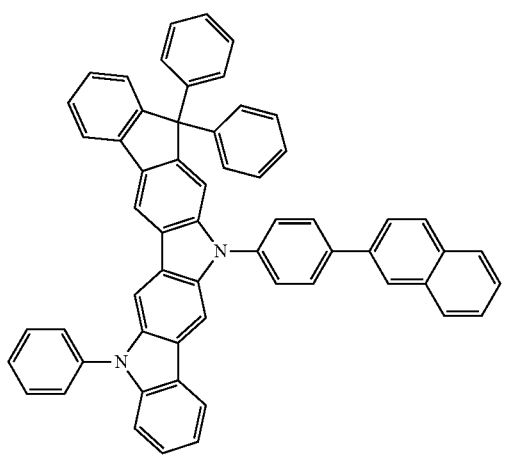

56

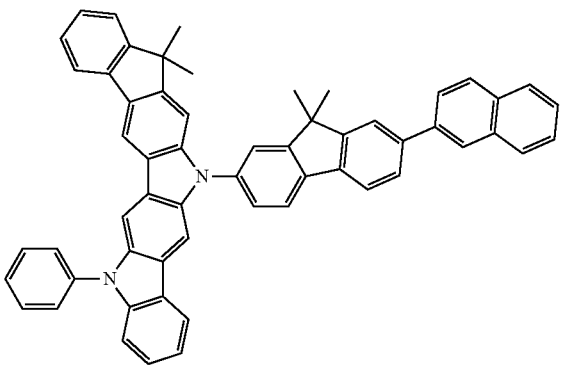

57

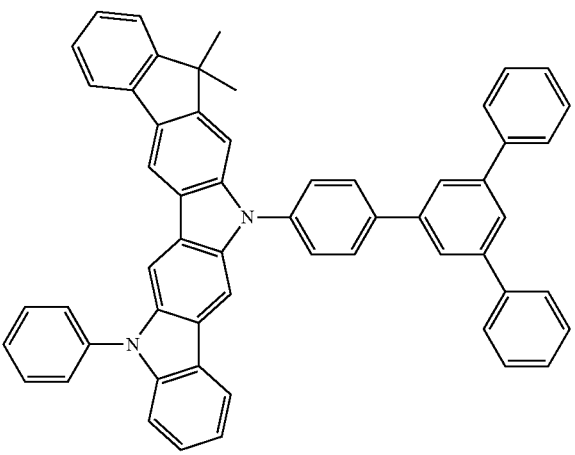

58

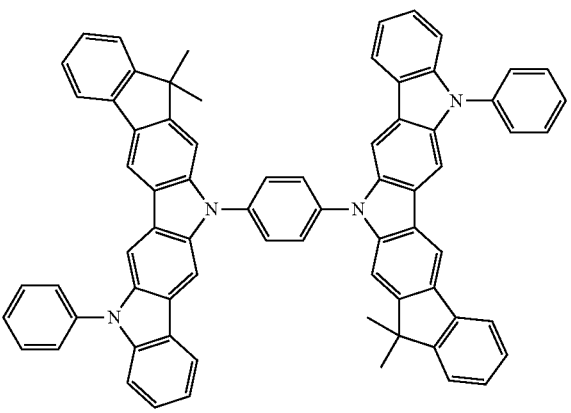

59

61
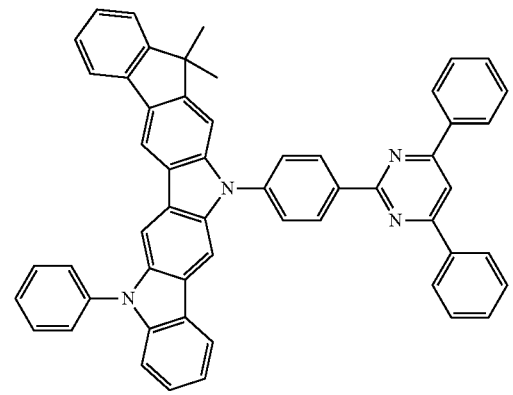
62
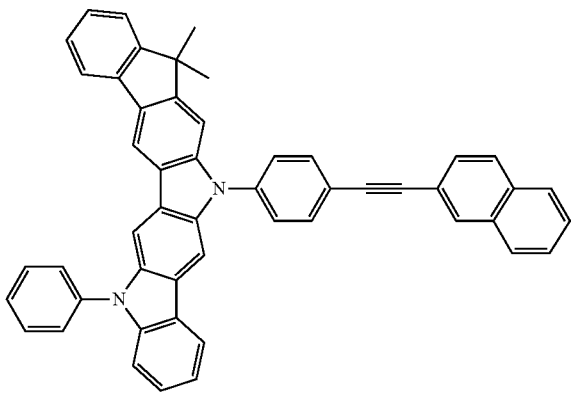
63
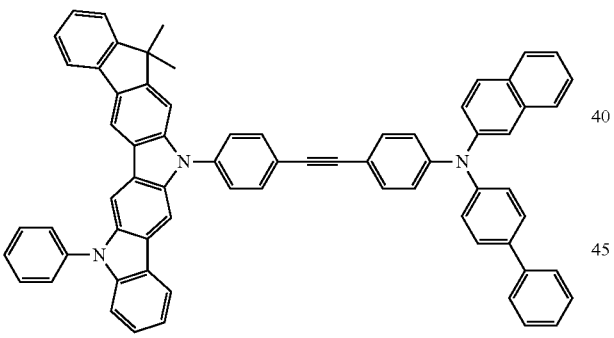
64
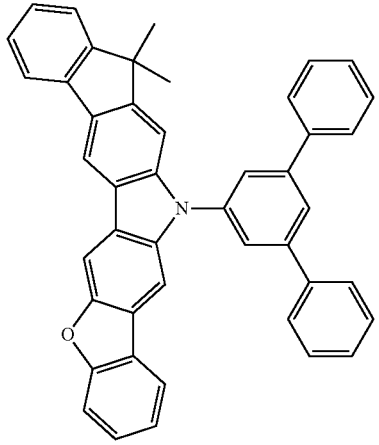
65
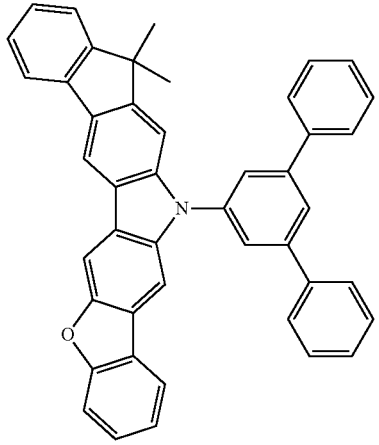
66
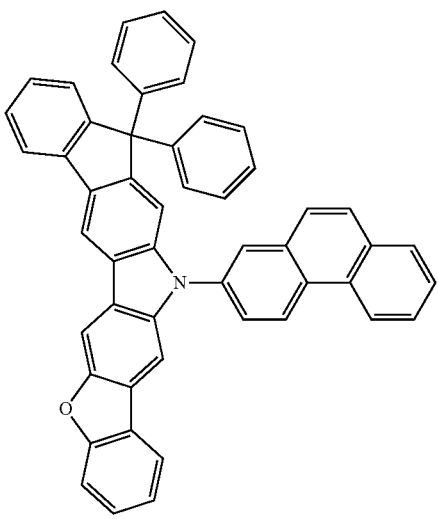
67
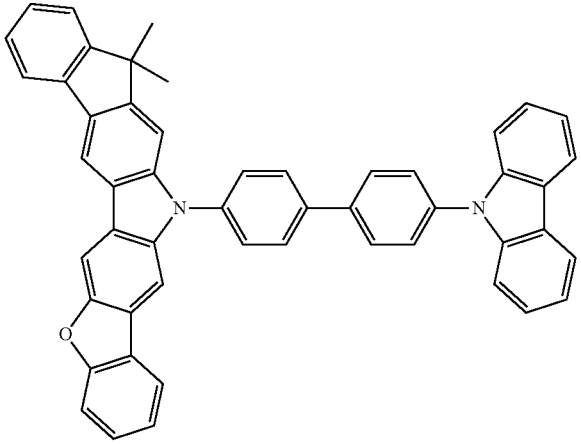

107
-continued
69
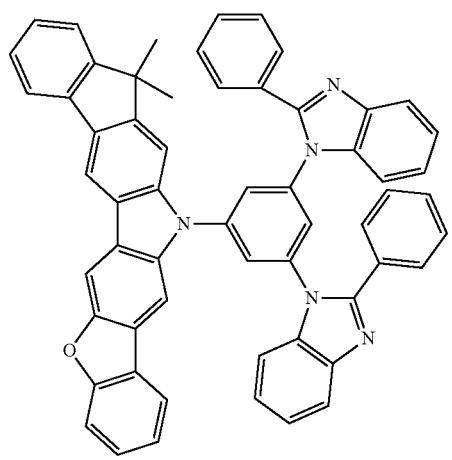
70
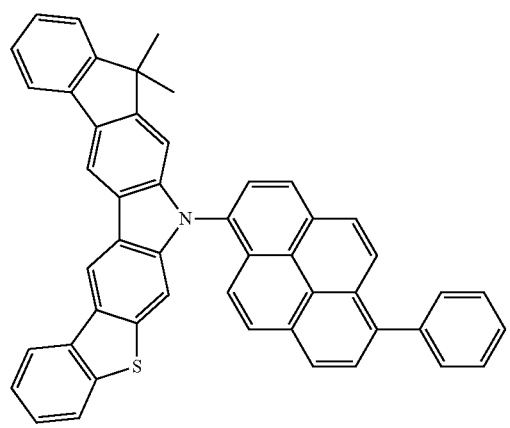
71
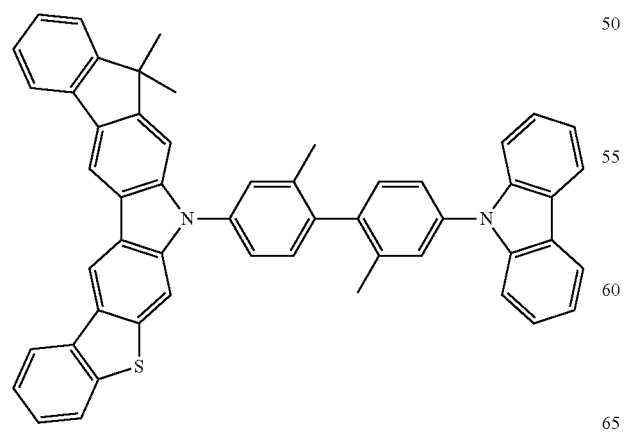
108
-continued
73
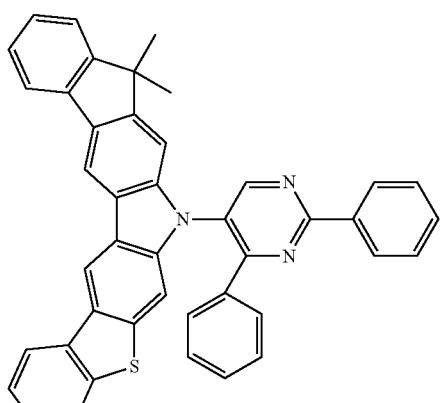
74
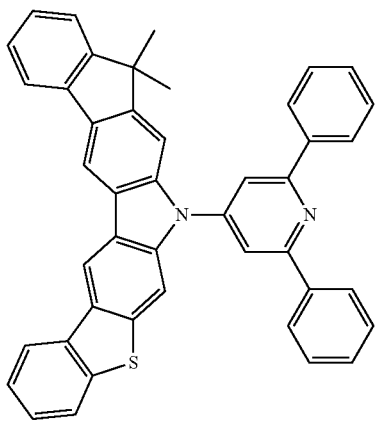
75
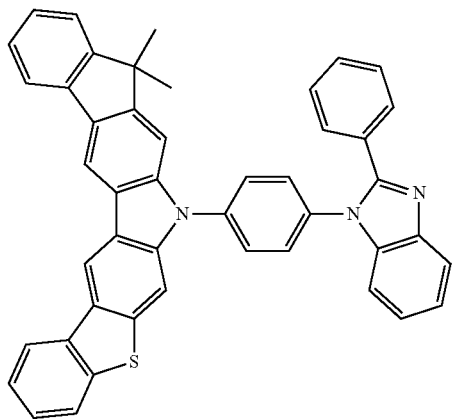

76

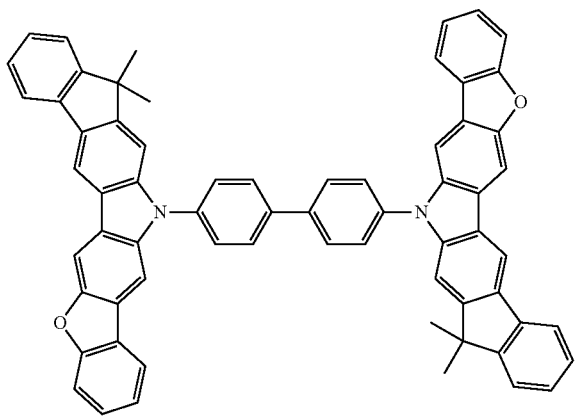

77

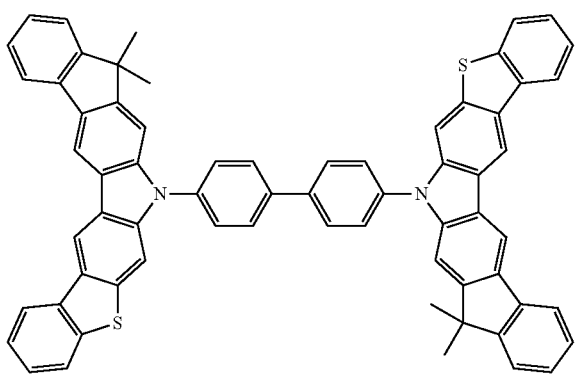

78

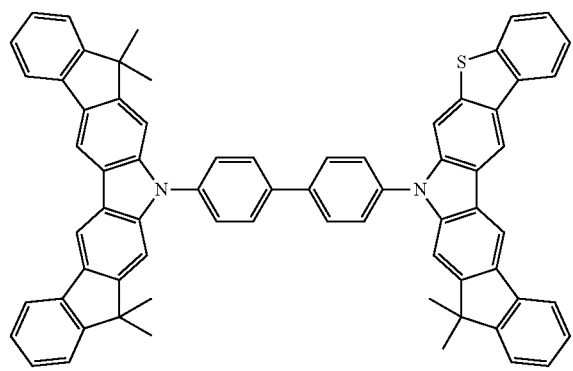

79

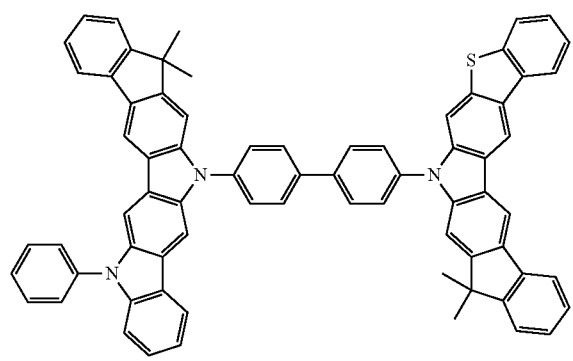

80

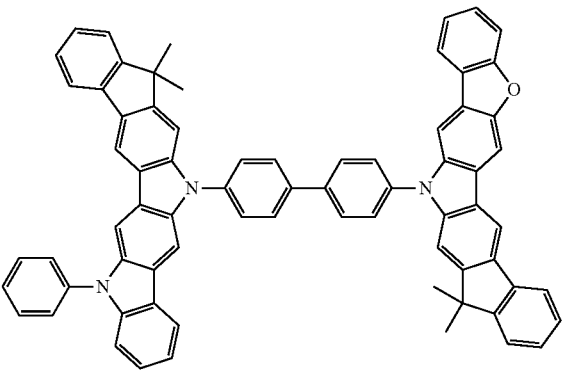

81

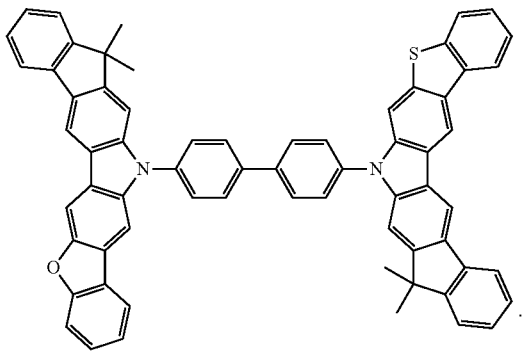

15. An organic light-emitting diode comprising:
a first electrode;
a second electrode disposed opposite to the first electrode; and
an organic layer interposed between the first electrode and the second electrode, the organic layer comprising a heterocyclic compound according to claim 1 as a single material or a mixture of different materials.

16. The organic light-emitting diode of claim 15, wherein the organic layer comprises at least one layer selected from the group consisting of a hole injection layer, a hole transport layer, a functional layer having both hole injecting and hole transporting capabilities, an electron blocking layer, an emission layer, a hole blocking layer, an electron transport layer, an electron injection layer, and a functional layer having both electron transporting and electron injecting capabilities.

17. The organic light-emitting diode of claim 15, wherein the organic layer comprises an emission layer comprising the heterocyclic compound.

18. The organic light-emitting diode of claim 15, wherein the organic layer comprises an emission layer comprising a fluorescent or phosphorescent host, wherein the fluorescent or phosphorescent host comprises the heterocyclic compound.

19. The organic light-emitting diode of claim 15, wherein the organic layer comprises an emission layer comprising a fluorescent dopant, wherein the fluorescent dopant comprises the heterocyclic compound.

20. The organic light-emitting diode of claim 15, wherein the organic layer comprises at least one of an electron transport layer, an electron injection layer, and a functional layer having both electron transporting and electron injecting capabilities, and at least one of the electron transport layer, the electron injection layer, and the functional layer having both electron transporting and electron injecting capabilities comprises the heterocyclic compound.

21. The organic light-emitting diode of claim 15, wherein the organic layer comprises at least one of an electron transport layer, an electron injection layer, and a functional layer having both electron transporting and electron injecting capabilities, and at least one of the electron transport layer, the electron injection layer, and the functional layer having both electron transporting and electron injecting capabilities comprises the heterocyclic compound and a metal-containing material.

22. The organic light-emitting diode of claim 15, wherein the organic layer comprises:
   at least one of an electron transport layer, an electron injection layer, and a functional layer having both electron transporting and electron injecting capabilities, wherein said at least one comprises the heterocyclic compound; and
   at least one emission layer of a red emission layer, a green emission layer, a blue emission layer and a white emission layer, wherein the at least one emission layer comprises a phosphorescent compound.

23. The organic light-emitting diode of claim 15, wherein the organic layer comprises at least one of the hole injection layer, a hole transport layer, a functional layer having both hole injecting and hole transporting capabilities, an electron blocking layer, an emission layer, a hole blocking layer, an electron transport layer, an electron injection layer, and a functional layer having both electron transporting and electron injecting capabilities, and at least one of the hole injection layer, the hole transport layer, and the functional layer having both hole injecting and hole transporting capabilities, the electron blocking layer, the emission layer, the hole blocking layer, the electron transport layer, the electron injection layer, and the functional layer having both electron transporting and electron injecting capabilities is formed by a wet process.

24. A flat panel display device comprising:
   a transistor comprising a source, a drain, a gate, and an active layer and an organic light-emitting diode according to claim 15, wherein one of the source and the drain is electrically connected to the first electrode of the organic light-emitting diode.

* * * * *